United States Patent
Arboleda-Velasquez

(10) Patent No.: US 12,188,950 B2
(45) Date of Patent: Jan. 7, 2025

(54) BLOOD BIOMARKERS AND DIAGNOSTIC METHODS FOR SMALL VESSEL DISEASES

(71) Applicant: The Schepens Eye Research Institute, Inc., Boston, MA (US)

(72) Inventor: Joseph F. Arboleda-Velasquez, Newton, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 55 days.

(21) Appl. No.: 17/992,529

(22) Filed: Nov. 22, 2022

(65) Prior Publication Data

US 2023/0078745 A1    Mar. 16, 2023

Related U.S. Application Data

(63) Continuation of application No. 16/499,192, filed as application No. PCT/US2018/024394 on Mar. 26, 2018, now abandoned.

(60) Provisional application No. 62/477,274, filed on Mar. 27, 2017.

(51) Int. Cl.

| C07K 16/28 | (2006.01) |
|---|---|
| G01N 33/50 | (2006.01) |
| G01N 33/53 | (2006.01) |
| G01N 33/68 | (2006.01) |
| C07K 14/71 | (2006.01) |
| C07K 14/78 | (2006.01) |
| C12N 9/64 | (2006.01) |

(52) U.S. Cl.
CPC ......... *G01N 33/6896* (2013.01); *C07K 16/28* (2013.01); *G01N 2333/65* (2013.01); *G01N 2333/705* (2013.01); *G01N 2333/78* (2013.01); *G01N 2333/96433* (2013.01); *G01N 2800/042* (2013.01); *G01N 2800/164* (2013.01); *G01N 2800/2871* (2013.01); *G01N 2800/56* (2013.01)

(58) Field of Classification Search
CPC ........ C07K 16/28; C07K 16/30; G01N 33/48; G01N 33/50; G01N 33/6896; G01N 33/53; G01N 2333/78; G01N 2333/705; G01N 2333/71; G01N 2333/964; G01N 2333/96433; G01N 2800/042; G01N 2800/164; G01N 2800/2871; G01N 2800/56; C12N 9/6424
See application file for complete search history.

(56) References Cited

U.S. PATENT DOCUMENTS

| 7,915,390 B2 | 3/2011 | Li et al. |
|---|---|---|
| 7,935,791 B2 | 5/2011 | Fung et al. |
| 8,187,839 B2 | 5/2012 | Li et al. |
| 8,226,943 B2 | 7/2012 | Gurney et al. |
| 2002/0182733 A1 | 12/2002 | Naldini et al. |
| 2003/0186290 A1 | 10/2003 | Tournier-Lasserve et al. |
| 2008/0131908 A1 | 6/2008 | Li et al. |
| 2011/0223183 A1 | 9/2011 | Kitajewski et al. |
| 2012/0100536 A1 | 4/2012 | Tsuji et al. |
| 2013/0129743 A1 | 5/2013 | Wu et al. |
| 2013/0323266 A1 | 12/2013 | Hoey et al. |
| 2013/0324468 A1 | 12/2013 | Cipolla et al. |
| 2014/0045198 A1 | 2/2014 | Montaner Villalonga et al. |
| 2014/0303013 A1* | 10/2014 | Hageman ............. A61K 31/225 506/9 |
| 2014/0323413 A1 | 10/2014 | Hageman et al. |
| 2015/0119278 A1 | 4/2015 | Goetzl |
| 2015/0268251 A1 | 9/2015 | Zaugg et al. |
| 2016/0115453 A1 | 4/2016 | Mummery et al. |
| 2016/0185852 A1 | 6/2016 | Okamura et al. |
| 2016/0305959 A1* | 10/2016 | Levy .................. G01N 33/6893 |
| 2017/0023576 A1 | 1/2017 | Cancilla |
| 2019/0350961 A1 | 11/2019 | Arboleda-Velasquez et al. |
| 2020/0102384 A1 | 4/2020 | Arboleda-Velasquez et al. |
| 2020/0375899 A1 | 12/2020 | Kim et al. |
| 2020/0377888 A1 | 12/2020 | Kim et al. |
| 2023/0190764 A1 | 6/2023 | Arboleda-Velasquez et al. |
| 2023/0190959 A1 | 6/2023 | Arboleda-Velasquez |
| 2023/0310446 A1 | 10/2023 | Kim et al. |

FOREIGN PATENT DOCUMENTS

WO    WO 2016046053    3/2016

OTHER PUBLICATIONS

Genbank Accession No. BC063833.1; Aug. 4, 2006.*
Altobelli et al., "HtrA1: Its future potential as a novel biomarker for cancer," Oncol Rep, 2015, 34(2):555-66.
Arboleda-Velasquez et al., "C455R notch3 mutation in a Colombian CADASIL kindred with early onset of stroke," Neurology, 2002, 59(2):277-279.
Arboleda-Velasquez et al., "CADASIL mutations impair Notch3 glycosylation by Fringe," Hum Mol Genet., 2005, 14(12):1631-1639.
Arboleda-Velasquez et al., "Hypomorphic Notch 3 alleles link Notch signaling to ischemic cerebral small-vessel disease, " Proc Natl Acad Sci USA, May 2011, 108(21):E128-E135.
Arboleda-Velasquez et al., "Linking Notch signaling to ischemic stroke," Proc Natl Acad Sci USA, 2008, 105(12):4856-4861.
Arboleda-Velasquez et al., "Notch Signaling Functions in Retinal Pericyte Survival," Invest Ophthalmol Vis Sci., 2014, 55(8):5191-5199.
Bae et al., "Regulation of IGFBP-1 in metabolic diseases," J Lifestyle Med., 2013, 3(2):73-79.
Baudrimont et al., "Autosomal Dominant Leukoencephalopathy and Subcortical Ischemic Stroke. A Clinicopathological study," Stroke, 1993, 24:122-125.
Beaufort et al., "Cerebral small vessel disease-related protease HtrA1 processes latent TGF-β binding protein 1 and facilitates TGF-β signaling," Proc Natl Acad Sci USA, 2014, 111(46):16496-16501.

(Continued)

*Primary Examiner* — Bridget E Bunner
(74) *Attorney, Agent, or Firm* — Fish & Richardson P.C.

(57) ABSTRACT

The present subject matter provides, inter alia, compositions, systems, kits, and methods for diagnosing and treating small vessel diseases (SVDs).

20 Claims, 12 Drawing Sheets

Specification includes a Sequence Listing.

(56) References Cited

OTHER PUBLICATIONS

Brass et al., "Case Dec. 2009: A 46-Year-Old Man with Migraine, Aphasia, and Hemiparesis and Similarly Affected Family Members," N Engl J Med, 2009, 360(16):1656-1665.
Cade, "Diabetes-Related Microvascular and Macrovascular Diseases in the Physical therapy setting," Phys Ther, 2008, 88(11):1322-1335.
Chabriat et al., "CADASIL," Lancet Neurol., 2009, 8:643-653.
Charidimou, "Book review: 'Cerebral small vessel disease'. What's the big deal about small vessels?," Front Neurol., 2015, 6:175, 2 pages.
Damico et al., "Serum endostatin is a genetically determined predictor of survival in pulmonary arterial hypertension," Am J Respir Crit Care Med, 2015, 191(2):208-218.
Di Donato et al., "Cerebral autosomal dominant arteriopathy with subcortical infarcts and leukoencephalopathy (CADASIL) as a model of small vessel disease: update on clinical, diagnostic, and management aspects," BMC Medicine, Feb. 2017, 15:41, 12 pages.
Dichgans et al., "Small in-frame deletions and missense mutations in Cadasil: 3D models predict misfolding of Notch3 EGF-like repeat domains," European Journal of Human Genetics, 2000, 8:280-285.
Dichgans et al., "The Phenotypic Spectrum of CADASIL: Clinical Findings in 102 Cases," Annals of Neurology, 1998, 44(5):731-739.
Dotti et al., "A Novel NOTCH3 Frameshift Deletion and Mitochondrial Abnormalities in a Patient With CADASIL," Arch Neurol., 2004, 61(6):942-945.
Erro et al., "Are granular osmiophilic material deposits an epiphenomenon in CADASIL?" Folia Neuropathol., 2015, 53:168-171.
Evans et al., "Cardiovascular comorbidities, inflammation, and cerebral small vessel disease," Cardiovasc Res, Nov. 2021, 117(13):2575-2588.
Fouillade et al., "Activating NOTCH3 Mutation in a Patient with Small-vessel-disease of the Brain," Human Mutation, 2008, 29(3):452, 9 pages.
Funatsu et al., "Outcome of vitreous surgery and the balance between vascular endothelial growth factor and endostatin," Invest Ophthalmol Vis Sci, 2003, 44(3):1042-1047.
Fung et al., "Delta-like 4 induces notch signaling in macrophages: implications for inflammation," Circulation, 2007, 115(23):2948-2956.
Ghosh et al., "Pericytes are involved in the pathogenesis of cerebral autosomal dominant arteriopathy with subcortical infarcts and leukoencephalopathy," Ann Neurol., 2015, 78(6):887-900.
Giau et al., "Genetic factors of cerebral small vessel disease and their potential clinical outcome," Int J Mol Sci, Sep. 2019, 20(17):4298, 27 pages.
Gould et al., "Role of COL4A1 in Small-Vessel Disease and Hemorrhagic Stroke," N Engl J Med, 2006, 354:1489-1496.
Gouya et al., "Association of endostatin with mortality in patients with chronic heart failure," Eur J Clin Invest, 2014, 44(2):125-35.
Hakim, "Silent, but preventable, perils," Nature, 2014, 510:S12.
Haque et al., "Inhibition of Tau Aggregation by a Rosamine Derivative that Blocks Tau Intermolecular Disulfide Cross-Linking", Amyloid, 2014, 21(3):185-190.
Hara et al., "Association of HTRA1 Mutations and Familial Ischemic Cerebral Small-Vessel Disease," N Engl J Med, 2009, 360:1729-1739.
Henshall et al., "Notch3 Is Necessary for Blood Vessel Integrity in the Central Nervous System," Arterioscler Thromb Vasc Biol., 2015, 35(2):409-420.
Iadecola, "The Pathobiology of Vascular Dementia," Neuron, 2013, 80(4):844-866.
Inagaki et al., "Upregulation of HtrA4 in the placentas of patients with severe pre-eclampsia," Placenta, 2012, 33(11):919-926.
International Preliminary Report on Patentability in International Appln. No. PCT/US2018/024394, dated Oct. 1, 2019, 16 pages.
International Preliminary Report on Patentability in International Appln. No. PCT/US2018/024397, dated Oct. 10, 2019, 10 pages.
International Preliminary Report on Patentability in International Appln. No. PCT/US2018/024407, dated Oct. 10, 2019, 12 pages.
International Search Report and Written Opinion in International Appln. No. PCT/US2018/024394, dated Aug. 8, 2018, 22 pages.
International Search Report and Written Opinion in International Appln. No. PCT/US2018/024397, dated Aug. 3, 2018, 14 pages.
International Search Report and Written Opinion in International Appln. No. PCT/US2018/024407, dated Sep. 18, 2018, 17 pages.
Ishiko et al., "Notch3 ectodomain is a major component of granular osmiophilic material (GOM) in CADASIL," Acta Neuropathol, 2006, 112:333-339.
Joutel and Faraci, "Cerebral Small Vessel Disease: Insights and Opportunities From Mouse Models of Collagen IV—Related Small Vessel Disease and Cerebral Autosomal Dominant Arteriopathy With Subcortical Infarcts and Leukoencephalopathy," Stroke, 2014, 45(4):1215-1221.
Joutel et al., "Cerebrovascular dysfunction and microcirculation rarefaction precede white matter lesions in a mouse genetic model of cerebral ischemic small vessel disease," J Clin Invest., 2010, 120(2):433-445.
Joutel et al., "Notch3 mutations in CADASIL, a hereditary adult-onset condition causing stroke and dementia, " Nature, 1996, 383:707-710.
Joutel et al., "Pathogenic Mutations Associated with Cerebral Autosomal Dominant Arteriopathy with Subcortical Infarcts and Leukoencephalopathy Differently Affect Jagged1 Binding and Notch3 Activity via the RBP/JK Signaling Pathway," Am J Hum Genet., 2004, 74:338-347.
Joutel et al., "Perturbations of the cerebrovascular matrisome: A convergent mechanism in small vessel disease of the brain?," J Cereb Blood Flow Metab, 2016, 36(1):143-157.
Joutel et al., "Skin biopsy immunostaining with a Notch3 monoclonal antibody for CADASIL diagnosis," Lancet, Dec. 2001, 358(9298):2049-2051.
Joutel et al., "Strong clustering and stereotyped nature of Notch3 mutations in CADASIL patients," Lancet, 1997, 350(9090):1511-1515.
Joutel et al., "The ectodomain of the Notch3 receptor accumulates within the cerebrovasculature of CADASIL patients," J Clin Invest, Mar. 2000, 105(5):597-605.
Kalaria, "Cerebrovascular Disease and Mechanisms of Cognitive Impairment," Stroke, 2012, 43(9):2526-2534.
Klueg and Muskavitch, "Ligand-receptor interactions and trans-endocytosis of Delta, Serrate and Notch: members of the Notch signalling pathway in Drosophila," J Cell Sci., 1999, 112(Pt 19):3289-3297.
Kodadek, "Protein microarrays: prospects and problems," Chem Biol., 2001, 8:105-115.
Kofler et al., "Combined deficiency of Notch1 and Notch3 causes pericyte dysfunction, models CADASIL and results in arteriovenous malformations," Sci Rep., 2015, 5:16449, 13 pages.
Kopan, "Notch signaling," Cold Spring Harb Perspect Biol., 2012, 4(10):a011213, 5 pages.
Lafkas et al., "NOTCH3 marks clonogenic mammary luminal progenitor cells in vivo," J Cell Biol., 2013, 203(1):47-56.
Li et al., "The Human Homolog of Rat Jagged1 Expressed by Marrow Stroma Inhibits Differentiation of 32D Cells through Interaction with Notch1," Immunity, 1998, 8:43-55.
Louvi et al., "Cadasil: A Critical Look at a Notch Disease," Dev Neurosci, 2006, 28:5-12.
Louvi et al., "Notch and disease: a growing field," Semin Cell Dev Biol., 2012, 23(4):473-480.
MayoClinic.org [online], "Small vessel disease," available on or before Mar. 29, 2016, via Internet Archive: Wayback Machine URL <http://web.archive.org/web/20160329050842/http://www.mayoclinic.org/diseases-conditions/small-vessel-disease/home/ovc-20198376>, retrieved on Feb. 11, 2021, URL <http://www.mayoclinic.org/diseases-conditions/small-vessel-disease/home/ovc-20198376>, 3 pages.
Meng et al., "Biochemical Characterization and Cellular Effects of CADASIL Mutants of NOTCH3," PLoS ONE, Sep. 2012, 7(9):1-13.

(56) References Cited

OTHER PUBLICATIONS

Moccia et al., "Hypomorphic NOTCH3 mutation in an Italian family with CADASIL features," Neurobiol Aging, 2015, 36(1):547. e5-547.e11.
Monet-Lepretre et al., "Abnormal recruitment of extracellular matrix proteins by excess Notch3ECD: a new pathomechanism in CADASIL," Brain, 2013, 136(6):1830-1845.
Navarro-Sobrino et al., "A large screening of angiogenesis biomarkers and their association with neurological outcome after ischemic stroke," Atherosclerosis, 2011, 216:205-211.
Nickoloff et al., "Jagged-1 mediated activation of notch signaling induces complete maturation of human keratinocytes through NF-κB and PPARδ," Cell Death Different., 2002, 9:842-855.
O'Reilly et al., "Endostatin: An Endogenous Inhibitor of Angiogenesis and Tumor Growth," Cell, 1997, 88(2):277-285.
Pippucci et al., "Homozygous NOTCH3 null mutation and impaired NOTCH3 signaling in recessive early onset arteriopathy and cavitating leukoencephalopathy," EMBO Mol Med., 2015, 7(6):848-858.
Primo et al., "Blood Biomarkers in a Mouse Model of CADASIL," Brain Research, 2016, 1644:118-126.
Rana et al., "Neurofilament Light Chain as an Early and Sensitive Predictor of Long-Term Neurological Outcome in Patients after Cardiac Arrest", International Journal of Cardiology, 2013, 168(2):1322-1327.
Robinson et al., "Retinal Findings in Cerebral Autosomal Dominant Arteriopathy with Subcortical Infarcts and Leukoencephalopathy (CADASIL)," Surv Ophthalmol., 2001, 45:445-448.
Rosenberg et al., "Consensus statement for diagnosis of subcortical small vessel disease," J Cereb Blood Flow Metab., 2015, 36(1):6-25.
Ruchoux and Maurage, "Cerebral autosomal dominant arteriopathy with subcortical infarcts and leukoencephalopathy," Journal of Neuropathology and Experimental Neurology, 1997, 56(9):947-964.
Ruchoux et al., "Systemic vascular smooth muscle cell impairment in cerebral autosomal dominant arteriopathy with subcortical infarcts and leukoencephalopathy," Acta Neuropathol., 1995, 89:500-512.
Rufa et al., "Retinal Nerve Fiber Layer Thinning in CADASIL: An Optical Coherence Tomography and MRI Study ," Cerebrovasc Dis., 2011, 31:77-82.
Rutten et al., "Hypomorphic NOTCH3 alleles do not cause CADASIL in humans," Hum Mutat., 2013, 34(11):1486-1489.
Rutten et al., "The NOTCH3 score: a pre-clinical CADASIL biomarker in a novel human genomic NOTCH3 transgenic mouse model with early progressive vascular NOTCH3 accumulation," Acta Neuropathol Commun., Dec. 2015, 3(1):89, 10 pages.
Rutten et al., "Therapeutic NOTCH3 cysteine correction in CADASIL using exon skipping: in vitro proof of concept, " Brain, 2016, 139(4):1123-1135.
Silva et al., "Predictive value of vascular disease biomarkers for digital ulcers in systemic sclerosis patients," Clin Exp Rheumatol, 2015, 33(4 Suppl 91):S127-S130.
Snyder et al., "Vascular Contributions to Cognitive Impairment and Dementia Including Alzheimer's Disease," Alzheimers Dement., 2015, 11(6):710-717.
Tan et al., "New insights into mechanisms of small vessel disease stroke from genetics," Clin Sci, Apr. 2017, 131(7):515-531.
Teoh et al., "Serum HtrA1 is differentially regulated between early-onset and late-onset preeclampsia," Placenta, 2015, 36(9):990-995.
Thompson et al., "Living Beyond Our Physiological Means: Small Vessel Disease of the Brain Is an Expression of a Systemic Failure in Arteriolar Function: A Unifying Hypothesis," Stroke, 2009, 40:e322-e330.
Tikka et al., "Congruence between NOTCH3 mutations and GOM in 131 CADASIL patients," Brain, 2009, 132:933-939.
Tikka et al., "Mini-Symposium: Pathology & Genetics of (non-CAA) Cerebral Microvascular Disease, CADASIL and CARASIL," Brain Pathology, 2014, 24(5):525-544.
Velasquez et al., "Hypomorphic Notch 3 alleles link Notch signaling to ischemic cerebral small-vessel disease," Proc Natl Acad Sci USA, 2011, 108(21):E128-E135.
Verdura et al., "Heterozygous HTRAI Mutations are Associated with Autosomal Dominant Cerebral Small Vessel Disease", Brain, Aug. 2015, 138:2347-2358.
Vermeer et al., "Silent brain infarcts: a systematic review," Lancet Neurol., 2007, 6(7):611-619.
Wardlaw et al., "Small vessel disease: mechanisms and clinical implications," Lancet Neurol, Jul. 2019, 18(7):684-696, 13 pages.
Wollenweber et al., "Cysteine-sparing CADASIL mutations in NOTCH3 show proaggregatory properties in vitro," Stroke, 2015, 46(3):786-792.
Xu et al., "Insights into Autoregulation of Notch3 from Structural and Functional Studies of Its Negative Regulatory Region," Structure, 2015, 23:1227-1235.
Yamamura et al., "Activation of Notch signaling by short-term treatment with Jagged-1 enhances store-operated $Ca^{2+}$ entry in human pulmonary arterial smooth muscle cells," Am J Physiol Cell Physiol., 2014, 306(9):C871-878.
Yoon et al., "NOTCH3 variants in patients with subcortical vascular cognitive impairment: a comparison with typical CADASIL patients," Neurobiol Aging, 2015, 36:2443.e1-2443.e7.
Zaucker et al., "notch3 is essential for oligodendrocyte development and vascular integrity in zebrafish," Dis Models Mech, Sep. 2013, 6(5):1246-1259.
Benjamin and Hill, "Tonicity of human tear fluid sampled from the cul-de-sac," British Journal of Ophthalmology, Aug. 1989, 73(8):624-627.

\* cited by examiner

FIG. 7A

| Mutation | C455R/WT76 | | | WT76/N3KO |
|---|---|---|---|---|
| Gender | Males | Males | Males | Males |
| Age | 100 days | 200 days | | 200 days |
| Protein | Average Fold Change (n=2) | | | |
| Angiogenin | 1.276 | 0.991 | | 0.743 |
| Angiopoietin-1 | 1.890 | 0.217 | | 1.059 |
| Cyr61 | 1.061 | N/D | | 1.631 |
| DPPIV | 1.003 | 1.037 | | 0.839 |
| Endoglin | 1.373 | N/D | | 0.964 |
| Endostatin/Col18α1 | 0.800 | 1.025 | | 1.409 |
| FGF acidic | 1.446 | N/D | | 1.323 |
| FGF basic | 0.724 | N/D | | N/D |
| HGF | 2.049 | N/D | | N/D |
| IGFBP-1 | 2.029 | 4.562 | | 0.652 |
| IGFBP-2 | 0.721 | 0.801 | | 1.042 |
| IGFBP-3 | 0.665 | 0.884 | | 1.198 |
| LEPTIN | 1.341 | 0.358 | | 0.615 |
| MMP-3 (pro & mature) | 0.70 | 1.61 | | 0.905 |
| MMP-9 | 0.752 | 0.774 | | 0.927 |
| NOV | 0.866 | 0.884 | | 0.717 |
| PDGF-AA | 2.761 | N/D | | 2.307 |
| PDGF-AB/PDGF-BB | 3.140 | N/D | | 1.564 |
| Pentraxin 3 (PTX3) | 1.424 | 0.757 | | 1.139 |
| Platelet Factor 4 (PF4) | 0.606 | 1.082 | | 0.991 |
| SDF-1 | 1.752 | 0.344 | | 1.175 |
| Serpin E1 | 1.01 | 2.43 | | 1.235 |
| Serpin F1 | 2.895 | 0.402 | | 0.959 |
| Thrombospondin-2 | 3.234 | N/D | | N/D |
| TIMP-1 | 5.106 | N/D | | 0.635 |
| TIMP-4 | 1.521 | 1.209 | | N/D |
| VEGF | N/D | N/D | | N/D |

FIG. 7B

| Reference | Gene Symbol | Average Z score |
|---|---|---|
| IPI:IPI00875870.1 | Aebp1 | 3.72 |
| IPI:IPI00330171.7 | Bat2d | 3.80 |
| IPI:IPI00467841.6 | Calm1;Calm3;Calm2 | 3.45 |
| IPI:IPI00848411.1 | Gm2451 | 4.85 |
| IPI:IPI00122012.7 | Golga2 | 4.04 |
| IPI:IPI00930711 | Htra1 | 5.08 |
| IPI:IPI00466610.5 | Map2k1 | 2.69 |
| IPI:IPI00222037.3 | Mia3 | 4.87 |
| IPI:IPI00134621.3 | Ran;LOC100045999 | 2.98 |
| IPI:IPI00830331.1 | Tpm1 | 3.27 |
| IPI:IPI00221814.4 | 6530401N04Rik | -4.05 |
| IPI:IPI00311383.1 | Adipoq | -2.89 |
| IPI:IPI00554894.2 | Anxa5 | -6.56 |
| IPI:IPI00224152.5 | Apex1 | -2.14 |
| IPI:IPI00458833.4 | Asph | -2.51 |
| IPI:IPI00331214.5 | Cd36 | -2.30 |
| IPI:IPI00313390.3 | Chchd6 | -3.08 |
| IPI:IPI00229598.4 | Cnp | -2.80 |
| IPI:IPI00110760.1 | Dnajb4 | -2.63 |
| IPI:IPI00331394.3 | Dnpep | -3.10 |
| IPI:IPI00127364.1 | Epn3 | -2.95 |
| IPI:IPI00122438.1 | Fbn1 | -2.15 |
| IPI:IPI00265899.6 | Fkbp1a | -2.85 |
| IPI:IPI00126508.1 | Fmo3 | -2.51 |
| IPI:IPI00265576.6 | Gm7308 | -2.73 |
| IPI:IPI00110658.1 | Hba-a1;Hba-a2 | -3.54 |
| IPI:IPI00469298.3 | Hnrnpall2 | -2.51 |
| IPI:IPI00331444.7 | Ipo7 | -2.54 |
| IPI:IPI00229517.5 | Lgals1 | -2.34 |
| IPI:IPI00129009.1 | Lims2 | -3.19 |
| IPI:IPI00111831.1 | Naca | -2.51 |
| IPI:IPI00118130.1 | Orm1 | -3.77 |
| IPI:IPI00230003.7 | Pitpna | -2.66 |
| IPI:IPI00473753.2 | Ppp2r2d | -3.23 |
| IPI:IPI00126939.1 | Prkcdbp | -3.28 |
| IPI:IPI00120495.1 | Prmt1 | -2.89 |
| IPI:IPI00407954.2 | Rap1b;LOC100048397 | -3.57 |
| IPI:IPI00222555.5 | S100a10 | -3.34 |
| IPI:IPI00121427.1 | S100a6 | -2.76 |
| IPI:IPI00129323.1 | Sfrs3 | -3.88 |
| IPI:IPI00230056.3 | Tbl1x | -2.86 |
| IPI:IPI00127983.1 | Tmed2;Gm10698 | -3.54 |
| IPI:IPI00874728.1 | Tpm2 | -3.09 |

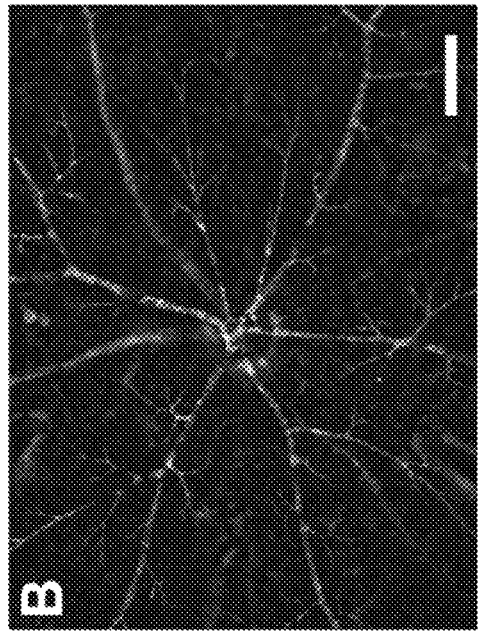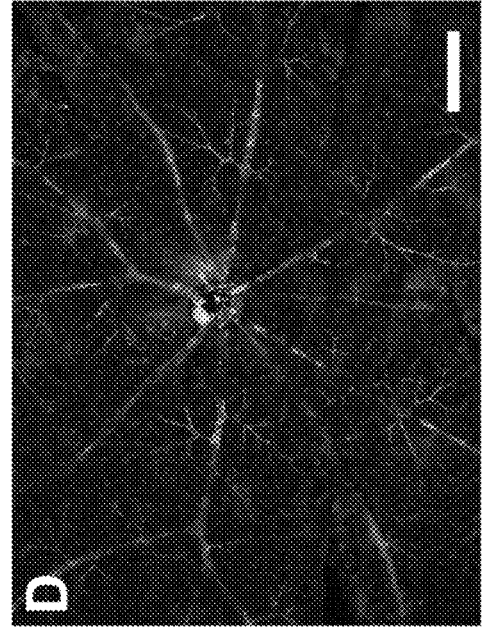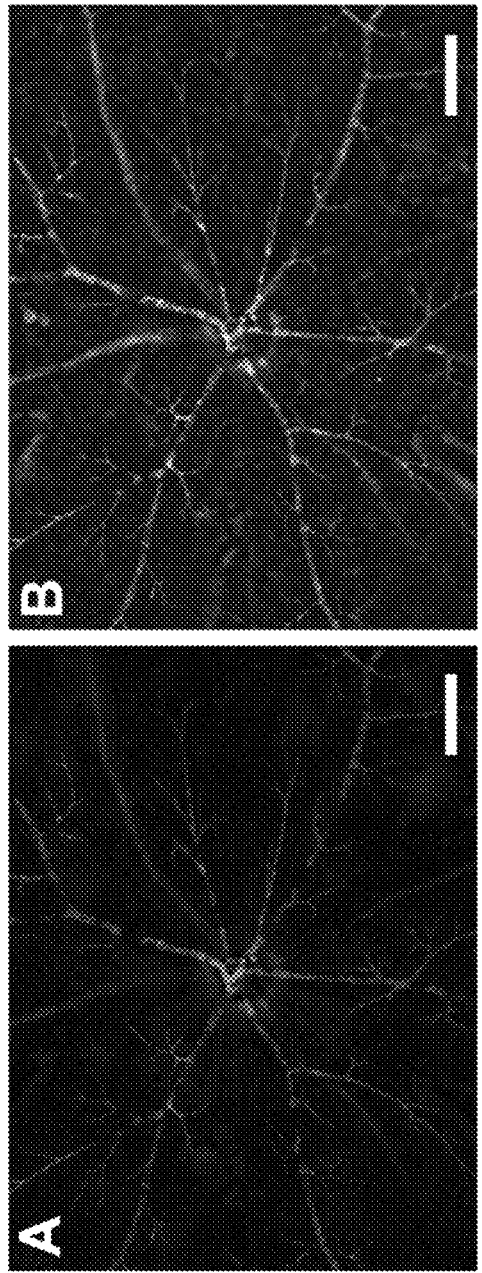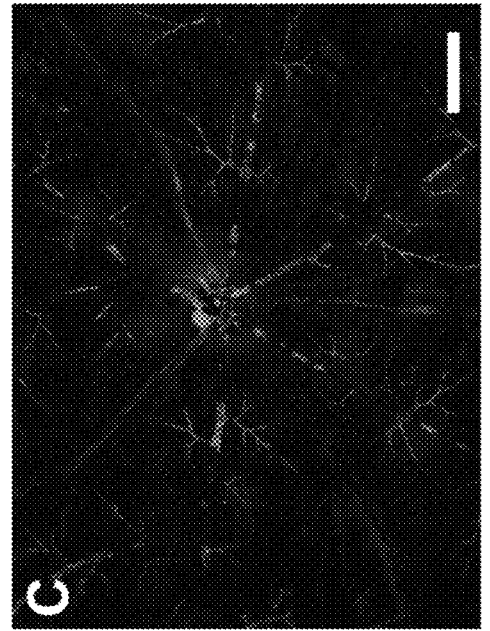

SEQUENCE LISTING

```
Sequence total quantity: 14
SEQ ID NO: 1            moltype = AA   length = 183
FEATURE                 Location/Qualifiers
source                  1..183
                        mol_type = protein
                        organism = Homo sapiens
SEQUENCE: 1
HSHRDFQPVL HLVALNSPLS GGMRGIRGAD FQCFQQARAV GLAGTFRAFL SSRLQDLYSI   60
VRRADRAAVP IVNLKDELLF PSWEALFSGS EGPLKPGARI FSFDGKDVLR HPTWPQKSVW  120
HGSDPNGRRL TESYCETWRT EAPSATGQAS SLLGGRLLGQ SAASCHHAYI VLCIENSFMT  180
ASK                                                                183

SEQ ID NO: 2            moltype = DNA   length = 549
FEATURE                 Location/Qualifiers
source                  1..549
                        mol_type = genomic DNA
                        organism = Homo sapiens
SEQUENCE: 2
cacagccacc gcgacttcca gccggtgctc cacctggttg cgctcaacag ccccctgtca   60
ggcggcatgc ggggcatccg cggggccgac ttccagtgct tccagcaggc gcgggccgtg  120
gggctggcgg gcaccttccg cgccttcctg tcctcgcgcc tgcaggacct gtacagcatc  180
gtgcgccgtg ccgaccgcgc agccgtgccc atcgtcaacc tcaaggacga gctgctgttt  240
cccagctggg aggctctgtt ctcaggctct gagggtccgc tgaagcccgg ggcacgcatc  300
ttctccttg acggcaagga cgtcctgagg cacccacct ggccccagaa gagcgtgtgg  360
catggctcgg accccaacgg gcgcaggctg accgagagct actgtgagac gtggcggacg  420
gaggctccct cggccacggg ccaggcctcc tcgctgctgg ggggcaggct cctggggcag  480
agtgccgcga gctgccatca cgcctacatc gtgctctgca ttgagaacag cttcatgact  540
gcctccaag                                                          549
```

| SEQ ID NO: 3 | moltype = AA   length = 2321 |
| --- | --- |
| FEATURE | Location/Qualifiers |
| source | 1..2321 |
| | mol_type = protein |
| | organism = Homo sapiens |

SEQUENCE: 3

```
MGPGARGRRR RRRPMSPPPP PPPVRALPLL LLLAGPGAAA PPCLDGSPCA NGGRCTQLPS    60
REAACLPPG  WVGERCQLED PCHSGPCAGR GVCQSSVVAG TARFSCRCPR GFRGPDCSLP   120
DPCLSSPCAH GARCSVGPDG RFLCSCPPGY QGRSCRSDVD ECRVGEPCRH GGTCLNTPGS   180
FRCQCPAGYT GPLCENPAVP CAPSPCRNGG TCRQSGDLTY DCACLPGFEG QNCEVNVDDC   240
PGHRCLNGGT CVDGVNTYNC QCPPEWTGQF CTEDVDECQL QPNACHNGGT CFNTLGGHSC   300
VCVNGWTGES CSQNIDDCAT AVCFHGATCH DRVASFYCAC PMGKTGLLCH LDDACVSNPC   360
HEDAICDTNP VNGRAICTCP PGFTGGACDQ DVDECSIGAN PCEHLGRCVN TQGSFLCQCG   420
RGYTGPRCET DVNECLSGPC RNQATCLDRI GQFTCICMAG FTGTYCEVDI DECQSSPCVN   480
GGVCKDRVNG FSCTCPSGFS GSTCQLDVDE CASTPCRNGA KCVDQPDGYE CRCAEGFEGT   540
LCDRNVDDCS PDPCHHGRCV DGIASFSCAC APGYTGTRCE SQVDECRSQP CRHGGKCLDL   600
VDKYLCRCPS GTTGVNCEVN IDDCASNPCT FGVCRDGINR YDCVCQPGFT GPLCNVEINE   660
CASSPCGEGG SCVDGENGFR CLCPPGSLPP LCLPPSHPCA HEPCSHGICY DAPGGFRCVC   720
EPGWSGPRCS QSLARDACES QPCRAGGTCS SDGMGFHCTC PPGVQGRQCE LLSPCTPNPC   780
EHGGRCESAP GQLPVCSCPQ GWQGPRCQQD VDECAGPAPC GPHGICTNLA GSFSCTCHGG   840
YTGPSCDQDI NDCDPNPCLN GGSCQDGVGS FSCSCLPGFA GPRCARDVDE CLSNPCGPGT   900
CTDHVASFTC TCPPGYGGFH CEQDLPDCSP SSCFNGGTCV DGVNSFSCLC RPGYTGAHCQ   960
HEADPCLSRP CLHGGVCSAA HPGFRCTCLE SFTGPQCQTL VDWCSRQPCQ NGGRCVQTGA  1020
YCLCPPGWSG RLCDIRSLPC REAAAQIGVR LEQLCQAGGQ CVDEDSSHYC VCPEGRTGSH  1080
CEQEVDPCLA QPCQHGGTCR GYMGGYMCEC LPGYNGDNCE DDVDECASQP CQHGGSCIDL  1140
VARYLCSCPP GTLGVLCEIN EDDCGPGPPL DSGPRCLHNG TCVDLVGGFR CTCPPGYTGL  1200
RCEADINECR SGACHAAHTR DCLQDPGGGF RCLCHAGFSG PRCQTVLSPC ESQPCQHGGQ  1260
CRPSPGPGGG LTFCTHCAQP FWGPRCERVA RSCRELQCPV GVPCQQTPRG PRCACPPGLS  1320
GPSCRSFPGS PPGASNASCA AAPCLHGGSC RPAPLAPFFR CACAQGWTGP RCEAPAAAPE  1380
VSEEPRCPRA ACQAKRGDQR CDRECNSPGC GWDGGDCSLS VGDPWRQCEA LQCWRLFNNS  1440
RCDPACSSPA CLYDNFDCHA GGRERTCNPV YEKYCADHFA DGRCDQGCNT EECGWDGLDC  1500
ASEVPALLAR GVLVLTVLLP PEELLRSSAD FLQRLSAILR TSLRFRLDAH GQAMVFPYHR  1560
PSPGSEPRAR RELAPEVIGS VVMLEIDNRL CLQSPENDHC FPDAQSAADY LGALSAVERL  1620
DFPYPLRDVR GEPLEPPEPS VPLLPLLVAG AVLLLVILVL GVMVARRKRE HSTLWFPEGF  1680
SLHKDVASGH KGRREPVGQD ALGMKNMAKG ESLMGEVATD WMDTECPEAK RLKVEEPGMG  1740
AEEAVDCRQW TQHHLVAADI RVAPAMALTP PQGDADADGM DVNVRGPDGF TPLMLASFCG  1800
GALEPMPTEE DEADDTSASI ISDLICQGAQ LGARTDRTGE TALHLAARYA RADAAKRLLD  1860
AGADTNAQDH SGRTPLHTAV TADAQGVFQI LIRNRSTDLD ARMADGSTAL ILAARLAVEG  1920
MVEELIASHA DVNAVDELGK SALHWAAAVN NVEATLALLK NGANKDMQDS KEETPLFLAA  1980
REGSYEAAKL LLDHFANREI TDHLDRLPRD VAQERLHQDI VRLLDQPSGP RSPPGPHGLG  2040
PLLCPPGAFL PGLKAAQSGS KKSRRPPGKA GLGPQGPRGR GKKLTLACPG PLADSSVTLS  2100
PVDSLDSPRP FGGPPASPGG FPLEGPYAAA TATAVSLAQL GGPGRAGLGR QPPGGCVLSL  2160
GLLNPVAVPL DWARLPPPAP PGPSFLLPLA PGPQLLNPGT PVSPQERPPP YLAVPGHGEE  2220
YPAAGAHSSP PKARFLRVPS EHPYLTPSPE SPEHWASPSP PSLSDWSEST PSPATATGAM  2280
ATTTGALPAQ PLPLSVPSSL AQAQTQLGPQ PEVTPKRQVL A                      2321
```

| SEQ ID NO: 4 | moltype = DNA   length = 8091 |
| --- | --- |
| FEATURE | Location/Qualifiers |
| source | 1..8091 |
| | mol_type = genomic DNA |
| | organism = Homo sapiens |

SEQUENCE: 4

```
acgcggcgcg gaggctggcc cgggacgcgc ccggagccca gggaaggagg gaggagggga    60
gggtcgcggc cggccgccat ggggccgggg gccgtggcc gccgccgccg ccgtcgcccg   120
atgtcgccgc caccgccacc gccacccgtg cgggcgctgc ccctgctgct gctgctagcg   180
gggccggggg ctgcagcccc ccctgcctg gacggaagcc cgtgtgcaaa tggaggtcgt   240
tgcacccagc tgccctcccg ggaggctgcc tgcctgtgcc cgcctggctg ggtgggtgag   300
cggtgtcagc tggaggaccc ctgtcactca ggccctgtg ctggccgtgg tgtctgccag   360
agttcagtgg tggctggcac cgcccgattc tcatgccggt gcccccgtgg cttccggagc   420
cctgactgct ccctgccaga tccctgcctc agcagccctt gtgccacgg tgccctgcg   480
tcagtgggc ccgatggacg cttcctctgc tcctgcccac ctggctacca gggccgcagc   540
tgccgaagcg acgtggatga gtgccgggtg ggtgagccct gccgccatgg tggcacctgc   600
ctcaacacac tggctccctt ccgctgccag tgtccagctg gctacacagg ccactatgt   660
gagaacccg cggtgccctg tgcgcccctca ccatgccgca acggggcac ctgcaggcag   720
agtggcgacc tcacttacga ctgtgcctgt cttcctgggt tgagggtca gaattgtgaa   780
gtgaacgtgg acgactgtcc aggacaccga tgtctcaatg ggggggacatg cgtggatggc   840
gtcaacacct ataactgcca gtgccctcct gagtggacag gccagttctg cacggaggac   900
gtggatgagt gtcagctgca gcccaacgcc tgccacaatg gggggtacctg cttcaacacg   960
ctgggtggcc acagctgcgt gtgtcaat ggctggacag gtgagagcttg cagtcagaat  1020
atcgatgact gtgccacagc cgtgtgcttc catgggccaa cctgccatga ccgcgtggct  1080
tctttctact gtgcctgccc catgggcaag actggcctcc tgtgtcacct ggatgacgcc  1140
tgtgtcagca cccctgccca cgaggatgct atctgtgaca caaatccggt gaacggccgg  1200
gccattgca cctgtcctcc cggcttcacg ggtgggcat gtgaccagga tgtggacgag  1260
tgctctatcg gcgccaaccc ctgcgagcac ttgggcgaac gaaggggcgg caggcggctg  1320
ttcctgtgcc agtgcggtcg tggctacact ggacctcgct gtgagaccga tgtcaacgaa  1380
tgtctgtcgg ggccctgccg aaaccaggcc acgtgcctcg accgcatag ccagttcacc  1440
tgtatctgta tggcaggctt cacaggaacc tattgcgagg tggacattga cgagtgtcag  1500
agtagccct gtgtcaacgg tggggtctgc aaggaccgag tcaatggctt cagctgcacc  1560
tgcccctcgg gcttcagcgg ctccacgtgt cagctgacg tggacgaatg cgccagcacg  1620
```

```
ccctgcagga atggcgccaa atgcgtggac cagcccgatg gctacgagtg ccgctgtgcc   1680
gagggctttg agggcacgct gtgtgatcgc aacgtggacg actgctcccc tgacccatgc   1740
caccatggtc gctgcgtgga tggcatcgcc agcttctcat gtgcctgtgc tcctggctac   1800
acgggcacac gctgcgagag ccaggtggac gaatgccgca gccagccctg ccgccatggc   1860
ggcaaatgcc tagacctggt ggacaagtac tctctgccgt gcccttctgg gaccacaggt   1920
gtgaactgcg aagtgaacat tgacgactgt gccagcaacc cctgcacctt tggagtctgt   1980
cgtgatgcca tcaaccgcta cgactgtgtc tgccaacctg gcttcacagg gccccttgt    2040
aacgtggaga tcaatgagtg tgcttccagc ccatgcggcg agggaggttc ctgtgtggat   2100
ggggaaaatg gcttccgctg cctctgcccg cctggctcct tgccccact ctgcctcccc    2160
ccgagccatc cctgtgccca tgagccctgc agtcacggca tctgctatga tgcacctgtg   2220
gggttccgct gtgtgtgtga gcctggctgg agtggccccc gctgcagcca gagcctggcc   2280
cgagacgcct gtgagtccca gccgtgcagg gccggtggga catgcagcag cgatggaatg   2340
ggtttccact gcacctgccc gcctggtgtc cagggacgtc agtgtgaact cctctccccc   2400
tgcaccccga accctgtga gcatggggc gctgcgagt ctgcccctgg ccagctgccc     2460
gtctgctcct gcccccaggg ctggcaaggc ccacgatgcc agcaggatgt ggacgagtgt   2520
gctggccccg caccctgtgg ccctcatggt atctgcacca acctggcagg gagtttcagc   2580
tgcacctgcc atggagggta cactggccct tcctgtgatc aggacatcaa tgactgtgac   2640
cccaacccat gcctgaacgg tggctcgtgc aagacgggcg ttgcctctt ttcctgctcc    2700
tgcctccctg gtttcgccgg cccacgatgc gcccgcgatg tggatgagtg cctgagcaac   2760
ccctgcggcc cgggcaccta taccgaccac gtggcctcct tcacctgcac ctgcccgccg   2820
ggctacgagg gcttccactg cgaacaggac ctgcccgact gcagcccag ctcctgcttc    2880
aatggcggga cctgtgtgga cggcgtgaac tcgttcagct gcctgtgccg tccccggctac  2940
acaggagccc actgccaaca tgaggcagac ccctgcctct cgcggccctg cctacacggg   3000
ggcgtctgca gcgccgccca ccctggcttc cgctgcacct gcctcgagag cttcacgggc   3060
ccgcagtgcc agacgctggt ggattggtgc agccgccagc cttgtcaaaa cggggggtcgc  3120
tgcgtccaga ctgggggcta ttgccttttgt cccctggat ggagcggacg cctctgctga   3180
atccgaagct tgccctgcag ggaggccgca gcccagatcg gggtgcggct ggagcagctg   3240
tgtcaggcgg gtgggcagtg tgtggatgaa gacagctccc actactgcgt gtgcccagag   3300
ggccgtactg gtagccactg tgagcaggag gtggaccct gcttggccca gccctgccag    3360
catggggga cctgccgtgg ctatatgggg ggctacatgt gtgagtgtct tcctggctag   3420
aatggtgata actgtgagga cgacgtggac gagtgtgccc ccagccctg ccagcacggg    3480
ggttcatgca ttgacctcgt ggcccgctat ctctgctcct gtccccagg aacgctgggg   3540
gtgctctgcg agattaatga ggatgactgc ggcccaggcc caccgctgga ctcagggccc   3600
cggtgcctac acaatggcac ctgcgtgaac ctggtgggtg gtttccgctg cacctgtccc   3660
ccaggataca ctggtttgcg ctgcgaggca gacatcaatg agtgcgctc aggtgcctgc   3720
cacgcggcac acaccgggga ctgcctgcag gacccaggcg gaggtttccg ttgcctttgt   3780
catgctggct tctcaggtcc tcgctgtcag actgtcctgt ctccctgcga gtcccagcca   3840
tgccagcatg gaggccagtg ccgtcctagc ccgggtcctg ggggtgggct gaccttcacc   3900
tgtcactgtg ccagccgtt ctggggtccg cgttgcagga gtggcgcg ctcctgccgg      3960
gagctgcagt gcccggtggg cgtcccatgc agcagacgc cccgcgggcc cgctgcgcgc    4020
tgccccccag ggttgtcggg accctcctgc cgcagcttcc cggggtcgcc gccggggcc    4080
agcaacgcca gctgcgcggc cgcccctgt ctccacgggg gctcctgccg cccgcgccg     4140
ctcgcgcct tcttccgctg cgcttgcgcg caggcgtgga cccggccgcg ctgcgaggcg    4200
cccgccgcgg cacccgaggt ctcggaggag ccgcggtgcc cgcgcgcgc ctgccaggcc    4260
aagcgcgggg accagcgctg cgaccgcgag tgcaacagcc caggctgcgg ctgggacggc   4320
ggcgactgct cgctgagcgt gggcgacccc tggcggcaat gcgaggcgct gcagtgctgg   4380
cgcctcttca acaacagccg ctgcgaccct gcctgcaact cgccccgcctg cctctacgac  4440
aacttcgact gccacgccgg tggccgcgag cgcacttgca acccggtgta cgagaagtac   4500
tgcgccgacc actttgccga cggccgctgc gaccagggct gcaacacgga gggagtcggc   4560
tgggatgggc tggattgtgc cagcgaggtg ccggccctgc tggcccgcgg cgtgctggtg   4620
ctcacagtgc tgctgccgcc ggaggagcta ctgcgttcca cgccgacctt tctgcagcgg   4680
ctcagcgcca tcctgcgcac ctcgctgcgc ttccgcctgg acgcgcacgg ccaggccatg   4740
gtcttccctt accaccggcc tagtcctggc tccgaacccc gggcccgtcg ggagctggcc   4800
cccgaggtga tcggctcggt agtaatgctg gagattgaca accggctctg cctgcagtcg   4860
cctgagaatg atcactgctt ccccgatgcc cagagcgcg ctgactaccc gggagcgttg    4920
tcagcggtgg agcgcctgga cttcccgtac ccactgcggg acgtgcgggg ggagccgctg   4980
gagcctccag aacccagcgt cccgctgctg ccactgctag tggcgggcgc tgtcttgctg   5040
ctggtcattc tcgtcctggg tgtcatggtg gcccggcgca agcgcgagca cagcaccctc   5100
tggttccctg agggcttctc actgcacaag gacgtggcct ctggtcacaa gggccggccg   5160
gaacccgtgg gccaggacgc gctgggcatg aagaacatgg ccaagggtga gagcctgatg   5220
ggggaggtgg ccacagactg gatggacaca gagtgcccag aggccaagcg gctaaaggta   5280
gaggagccag gcatggggc tgaggaggct gtggattgcc gtcagtggac tcaacaccat   5340
ctggttgctg ctgacatccg cgtggcacca gccatgcac tgacaccacc acagggcgac    5400
gcagatgctg atgcatgga tgtcaatgtg cgtggccgaa atggcttcac cccgctaatg   5460
ctggcttcct tctgtggggg ggctctggag ccaatgccaa ctgaagagga tgaggcagat   5520
gacacatcag ctagcatcat ctccgacctg atctgccagg ggctcagct ggggcacgg    5580
actgaccgta ctgcgagac tgctttgcac ctggctgccc gttatgcccg tgctgatgca   5640
gccaagcggc tgctggatgc tggggcagac accaatgcca aggaccactc aggccgcact   5700
cccctgcaca cagctgtcac agccgatgcc caggtgtct tccagattct catccgaac   5760
cgctctacag acttggatgc ccgcatggca gatgtcaa cggcactgat cctggcggcc    5820
cgcctggcag tagagggcat ggtgaagag ctcatcgcca gccatgctga tgtcaatgct   5880
gtggatgagc ttgggaaatc agccttacac tgggctgcgg ctgtgaacaa cgtggaagcc   5940
actttggccc tgctcaaaaa tggagccaat aaggacatgc aggatagcaa ggaggagacc   6000
ccctattcc tggccgccgc cgagggcagc tatgaggctg ccaagctgct gttggaccac   6060
tttgccaacc gtgagatcac cgaccacctg acaggctgc gcggggacgt agcccaggag   6120
agactgcacc aggacatcgt gcgcttgctg gatcaaccca gtgggccccg cagcccccc    6180
ggtcccacg gcctggggcc tctgctctgt cctccagggg ccttcctccc tggcctcaaa   6240
gcggcacagt cgggtccaa gaagagcagg aggcccccg gaaggcggg gctggggccg     6300
cagggccccc gggggcgggg caagaagctg acgctggcct gcccgggccc cctggctgac   6360
```

-continued

```
agctcggtca cgctgtcgcc cgtggactcg ctggactccc cgcggccttt cggtgggccc    6420
cctgcttccc ctggtggctt cccccttgag gggccctatg cagctgccac tgccactgca    6480
gtgtctctgg cacagcttgg tgggccaggc cgggcaggtc tagggcgcca gccccctgga    6540
ggatgtgtac tcagcctggg cctgctgaac cctgtggctg tgccctcga ttgggcccgg     6600
ctgccccac ctgcccctcc aggccctcg ttcctgctgc cactggcgcc gggaccccga      6660
ctgctcaacc cagggacccc cgtctcccg caggagcggc cccgccttta cctggcagtc     6720
ccaggacatg gcgaggagta cccggtggct ggggcacaca gcagcccccc aaaggcccgc    6780
ttcctgcggg ttcccagtga gcacccttac ctgaccccat cccccgaatc ccctgagcac    6840
tgggccagcc cctcacctcc ctccctctca gactggtccg aatccacgcc tagcccagcc    6900
actgccactg gggccatggc caccaccact ggggcactgc ctgcccagcc acttcccttg    6960
tctgttccca gctcccttgc tcaggccag acccagctgg ggcccagcc ggaagttacc      7020
cccaagaggc aagtgttggc ctgagacgct cgtcagttct tagatcttgg gggcctaaag    7080
agaccccgt cctgcctcct ttctttctct gtctcttcct tccttttagt cttttttcatc    7140
ctcttctctt tccaccaacc ctcctgcatc cttgccttgc agcgtgaccg agataggtca    7200
tcagcccagg gcttcagtct tcctttattt ataatgggtg ggggctacca cccaccctct    7260
cagtcttgtg aagagtctgg gacctcctc ttccccactt ctctcttccc tcattccttt     7320
ctctctcctt ctggcctctc atttccttac actctgacat gaatgaatta ttattattt     7380
tcttttttctt ttttttttta cattttgtat agaaacaaat tcatttaaac aaacttatta   7440
ttattatttt ttacaaaata tatatatgga gatgctccct cccctgtga accccccagt     7500
gccccgtgg ggctgagtct gtgggcccat tcggccaagc tggattctgt gtacctagta     7560
cacaggcatg actgggatcc cgtgtaccga gtacacgacc caggtatgta ccaagtaggc    7620
accctggc gcaccactg gggcaggggg tcggggagt gttgggagcc tcctccccac        7680
ccccacctccc tcacttcact gcattccaga ttggacatgt tccatagcct tgctggggaa   7740
gggcccactg ccaactccct ctgccccagc cccaccttg gccatctccc tttgggaact     7800
agggggctgc tggtgggaaa tgggagccag ggcagatgta tgcattcctt tatgtccctg    7860
taaatgtggg actacaagaa gaggagctgc ctgagtggta cttctcttc ctggtaatcc     7920
tctggcccag ccttatggca gaatagaggt atttttaggc tattttgta atatggcttc     7980
tggtcaaaat ccctgtgtag ctgaattccc aagccctgca ttgtacagcc ccccactccc   8040
ctcaccacct aataaaggaa tagttaacac tcaaaaaaaa aaaaaaaaa a             8091
```

```
SEQ ID NO: 5           moltype = AA  length = 1532
FEATURE                Location/Qualifiers
source                 1..1532
                       mol_type = protein
                       organism = Homo sapiens
SEQUENCE: 5
APPCLDGSPC ANGGRCTQLP SREAACLCPP GWVGERCQLE DPCHSGPCAG RGVCQSSVVA    60
GTARFSCRCP RGFRGPDCSL PDPCLSSPCA HGARCSVGPD GRFLCSCPPG YQGRSCRSDV   120
DECRVGEPCR HGGTCLNTPG SFRCQCPAGY TGPLCENPAV PCAPSPCRNG GTCRQSGDLT   180
YDCACLPGFE GQNCEVNVDD CPGHRCLNGG TCVDGVNTYN CQCPPEWTGQ FCTEDVDECQ   240
LQPNACHNGG TCFNTLGGHS CVCVNGWTGE SCSQNIDDCA TAVCFHGATC HDRVASFYCA   300
CPMGKTGLLC HLDDACVSNP CHEDAICDTN PVNGRAICTC PPGFTGGACD QDVDECSIGA   360
NPCEHLGRCV NTQGSFLCQC GRGYTGPRCE TDVNECLSGP CRNQATCLDR IGQFTCICMA   420
GFTGTYCEVD IDECQSSPCV NGGVCKDRVN GFSCTCPSGF SGSTCQLDVD ECASTPCRNG   480
AKCVDQPDGY ECRCAEGFEG TLCDRNVDDC SPDDPCHHGRC VDGIASFSCA CAPGYTGTRC  540
ESQVDECRSQ PCRHGGKCLD LVDKYLCRCP SGTTGVNCEV NIDDCASNPC TFGVCRDGIN   600
RYDCVCQPGF TGPLCNVEIN ECASSPCGEG GSCVDGENPC RCLCPPGSLP PLCLPPSHPC   660
AHEPCSHGIC YDAPGGFRCV CEPGWSGPRC SQSLARDACE SQPCRAGGTC SSDGMGFHCT   720
CPPGVQGRQC ELLSPCTPNP CEHGGRCESA PGQLPVCSCP QGWQGPRCQQ DVDECAGPAP   780
CGPHGICTNL AGSFSCTCHG GYTGPSCDQD INDCDPNPCL NGGSCQDGVG SFSCSCLPGF   840
AGPRCARDVD ECLSNPCGPG TCTDHVASFT CTCPPGYGGF HCEQDLPDCS PSSCFNGGTC   900
VDGVNSFSCL CRPGYTGAHC QHEADPCLSR PCLHGGVCSA AHPGFRCTCL ESFTGPQCQT   960
LVDWCSRQPC QNGGRCVQTG AYCLCPPGWS GRLCDIRSLP CREAAAQIGV RLEQLCQAGG  1020
QCVDEDSSHY CVCPEGRTGS HCEQEVDPCL AQPCQHGGTC RGYMGGYMCE CLPGYNGDNC  1080
EDDVDECASQ PCQHGGSCID LVARYLCSCP PGTLGVLCEI NEDDCGPGPP LDSGPRCLHN  1140
GTCVDLVGGF RCTCPPGYTG LRCEADINEC RSGACHAAHT RDCLQDPGGG FRCLCHAGFS  1200
GPRCQTVLSP CESQPCQHGG QCRPSPGPGG GLTFTCHCAQ PFWGPRCERV ARSCRELQCP  1260
VGVPCQQTPR GPRCACPPGL SGPSCRSFPG SPPGASNASC AAAPCLHGGS CRPAPLAPFF  1320
RCACAQGWTG PRCEAPAAAP EVSEEPRCPR AACQAKRGDQ RDRECNSPG CGWDGGDCSL   1380
SVGDPWRQCE ALQCWRLFNN SRCDPACSSP ACLYDNFDCH AGGRERTCNP VYEKYCADHF   1440
ADGRCDQGCN TEECGWDGLD CASEVPALLA RGVLVLTVLL PPEELLRSSA DFLQRLSAIL   1500
RTSLRFRLDA HGQAMVFPYH RPSPGSEPRA RR                                 1532
```

```
SEQ ID NO: 6           moltype = AA  length = 1533
FEATURE                Location/Qualifiers
source                 1..1533
                       mol_type = protein
                       organism = Mus musculus
SEQUENCE: 6
APPCLDGSPC ANGGRCTHQQ PSLEAACLCL PGWVGERCQL EDPCHSGPCA GRGVCQSSVV    60
AGTARFSCRC LRGFQGPDCS QPDPCVSRPC VHGAPCSVGP DGRFACACPP GYQGQSCQSD   120
IDECRSGTTC RHGGTCLNTP GSFRCQCPLG YTGLLCENPV VPCAPSPCRN GGTCRQSSDV   180
TYDCACLPGF EGQNCEVNVD DCPGHRCLNG GTCVDGVNTY NCQCPPEWTG QFCTEDVDEC   240
QLQPNACHNG GTCFNLLGGH SCVCVNGWTG ESCSQNIDDC ATAVCFHGAT CHDRVASFYC   300
ACPMGKTGLL CHLDDACVSN PCHEDAICDT NPVSGRAICT CPPGFTGGAC DQDVDECSIG   360
ANPCEHLGRC VNTQGSFLCQ CGRGYTGPRC ETDVNECLSG PCRNQATCLD RIGQFTCICM   420
AGFTGTYCEV DIDECQSSPC VNGGVCKDRV NGFSCTCPSG FSGSMCQLDV DECASTPCRN   480
GAKCVDQPDG YECRCAEGFE GTLCERNVDD CSPDPCHHGR CVDGIASFSC ACAPGYTGIR   540
CESQVDECRS QPCRYGGKCL DLVDKYLCRC PPGTTGVNCE VNIDDCASNP CTFGVCRDGI   600
```

```
NRYDCVCQPG FTGPLCNVEI NECASSPCGE GGSCVDGENG FHCLPPGSL  PPLCLPANHP     660
CAHKPCSHGV CHDAPGGFRC VCEPGWSGPR CSQSLAPDAC ESQPCQAGGT CTSDGIGFRC     720
TCAPGFQGHQ CEVLSPCTPS LCEHGGHCES DPDRLTVCSC PPGWQGPRCQ QDVDECAGAS    780
PCGPHGTCTN LPGNFRCICH RGYTGPFCDQ DIDDCDPNPC LHGGSCQDGV GSFSCSCLDG     840
FAGPRCARDV DECLSSPCGP GTCTDHVASF TCACPPGVGA FHCEIDLPDC SPSSCFNGGT    900
CVDGVSSFSC LCRPGYTGTH CQYEADPCFS RPCLHGGICN PTHPGFECTC REGFTGSQCQ     960
NPVDWCSQAP CQNGGRCVQT GAYCICPPGW SGRLCDIQSL PCTEAAAQMG VRLEQLCQEG    1020
GKCIDKGRSH YCVCPEGRTG SHCEHEVDPC TAQPCQHGGT CRGYMGGYVC ECPAGYAGDS   1080
CEDNIDECAS QPCQNGGSCI DLVARYLCSC PPGTLGVLCE INEDDCDLGP SLDSGVQCLH    1140
NGTCVDLVGG FRCNCPPGYT GLHCEADINE CRPGACHAAH TRDCLQDPGG HFRCVCHPGF    1200
TGPRCQIALS PCESQPCQHG GQCRHSLGRG GGLTFTCHCV PPFWGLRCER VARSCRELQC    1260
PVGIPCQQTA RGPRCACPPG LSGPSCRVSR ASPSGATNAS CASAPCLHGG SCLPVQSVPF    1320
FRCVCAPGWG GPRCETPSAA PEVPEEPRCP RAACQAKRGD QNCDRECNTP GCGWDGGDCS    1380
LNVDDPWRQC EALQCWRLFN NSRCDPACSS PACLYDNFDC YSGGRDRTCN PVYEKYCADH    1440
FADGRCDQGC NTEECGWDGL DCASEVPALL ARGVLVLTVL LPPEELLRSS ADFLQRLSAI    1500
LRTSLRFRLD ARGQAMVFPY HRPSPGSESR VRR                                1533

SEQ ID NO: 7           moltype = AA  length = 259
FEATURE                Location/Qualifiers
source                 1..259
                       mol_type = protein
                       organism = Homo sapiens
SEQUENCE: 7
MSEVPVARVW LVLLLLTVQV GVTAGAPWQC APCSAEKLAL CPPVSASCSE VTRSAGCGCC     60
PMCALPLGAA CGVATARCAR GLSCRALPGE QQPLHALTRG QGACVQESDA SAPHAAEAGS    120
PESPESTEIT EEELLDNFHL MAPSEEDHSI LWDAISTYDG SKALHVTNIK KWKEPCRIEL    180
YRVVESLAKA QETSGEEISK FYLPNCNKNG FYHSRQCETS MDGEAGLCWC VYPWNGKRIP    240
GSPEIRGDPN CQIYFNVQN                                                259

SEQ ID NO: 8           moltype = DNA  length = 1660
FEATURE                Location/Qualifiers
source                 1..1660
                       mol_type = genomic DNA
                       organism = Homo sapiens
SEQUENCE: 8
ggtgcactag caaacaaac  ttattttgaa cactcagctc ctagcgtgcg gcgctgccaa     60
tcattaacct cctggtgcaa gtggcgcggc ctgtgccctt tataaggtgc gcgctgtgtc    120
cagcgagcat cggccaccgc catcccatcc agcgagcatc tgccgccgcg ccgccgccac    180
cctcccagag agcactggcc accgctccac catcacttgc ccagagtttg ggccaccgcc    240
cgccgccacc agcccagaga gcatcggccc ctgtctgctg ctcgcgcctg agatgtcag     300
aggtccccgt tgctcgcgtc tggctggtac tgctcctgct gactgtccag gtcggcgtga    360
cagccggcgc tccgtggcag tgcgcgccct gctccgccga aagctcgcg  ctctgccgc     420
cggtgtccgc ctcgtgctcg gaggtcaccc ggtccgcgtg ctgcccgatg              480
gcgccctgcc tctgggcgcc gcgtgcggcg tggcgactga cgctgcgcc  cggggactca    540
gttgccgcgc gctgccgggg gagcagcaac ctctgcacgc cctcacccgc ggccaaggcg    600
cctgcgtgca ggagtctgac gcctccgctc ccatgctgc  agaggcaggg agccctgaaa    660
gcccagagag cacggagata actgaggagg agctcctgga taatttccat ctgatggcc    720
cttctgaaga ggatcattcc atcctttggg acgccatcag tacctatgat ggctcgaagg    780
ctctccatgt caccaacatc aaaaaatgga aggagccctg ccgaatagaa ctctacagag    840
tcgtagagag tttagccaag gcacaggaga catcaggaga agaaatttcc aaattttacc    900
tgccaaactg caacaagaat ggattttatc acagcagaca gtgtgagaca tccatgatg    960
gagaggcggg actctgctgg tgcgtctacc cttggaatgg gaagaggatc cctgggctc    1020
cagagatcag gggagacccc aactgccaga tatattttaa tgtacaaaac tgaaaccaga   1080
tgaaataatg ttctgtcacg tgaaatattt agtatatag  tatatttata ctctagaaca   1140
tgcacattta tatatatatg tatatgtata tatatatagt aactacttta tactccata    1200
acataactg  atatagaaag ctgtttattt attcactgta agtttatttt ttctacacag    1260
taaaaacttg tactatgtta ataacttgtc ctatgtcaat ttgtatatca tgaaacactt   1320
ctcatcatat tgtatgtaag taattgcatt tctgctcttc caaagctcct gcgtctgttt    1380
ttaaagagca tggaaaaata ctgcctagaa aatgcaaaat gaaataagag agagtagttt   1440
ttcagctagt ttgaaggagg acggttaact tgtatattcc accattcaca tttgatgtac    1500
atgtgtaggg aaagttaaaa gtgttgatta cataatcaaa gctacctgtg gtgatgttgc    1560
cacctgttaa aatgtacact ggatatgttg ttaaacacgt gtctataatg gaaacattta    1620
caataaaatat tctgcatgga aatactgtta aaaaaaaaaa                         1660

SEQ ID NO: 9           moltype = AA  length = 480
FEATURE                Location/Qualifiers
source                 1..480
                       mol_type = protein
                       organism = Homo sapiens
SEQUENCE: 9
MQIPRAALLP LLLLLLAAPA SAQLSRAGRS APLAAGCPDR CEPARCPPQP EHCEGGRARD     60
ACGCCEVCGA PEGAACGLQE GPCGEGLQCV VPFGVPASAT VRRRAQAGLC VCASSEPVCG    120
SDANTYANLC QLRAASRRSE RLHRPPVIVL QRGACGQGQE DPNSLRHKYN FIADVVEKIA    180
PAVVHIELFR KLPFSKREVP VASGSGFIVS EDGLIVTNAH VVTNKHRVKV ELKNGATYEA    240
KIKDVDEKAD IALIKIDHQG KLPVLLLGRS SELRPGEFVV AIGSPFSLQN TVTTGIVSTT    300
QRGGKELGLR NSDMDYIQTD AIINYGNSGG PLVNLDGEVI GINTLKVTAG ISFAIPSDKI    360
KKFLTESHDR QAKGKAITKK KYIGIRMMSL TSSKAKELKD RHRDFPDVIS GAYIIEVIPD    420
TPAEAGGLKE NDVIISINGQ SVVSANDVSD VIKRESTLNM VVRRGNEDIM ITVIPEEIDP    480
```

-continued

```
SEQ ID NO: 10              moltype = AA    length = 22
FEATURE                    Location/Qualifiers
REGION                     1..22
                           note = positions 1-22 of (SEQ ID NO: 9) which correspond to
                           the signalpeptide
source                     1..22
                           mol_type = protein
                           organism = synthetic construct
SEQUENCE: 10
MQIPRAALLP LLLLLLAAPA SA                                              22

SEQ ID NO: 11              moltype = AA    length = 161
FEATURE                    Location/Qualifiers
REGION                     1..161
                           note = positions 204-364 of SEQ ID NO: 9 which correspond
                           to a serineprotease domain
source                     1..161
                           mol_type = protein
                           organism = synthetic construct
SEQUENCE: 11
GSGFIVSEDG LIVTNAHVVT NKHRVKVELK NGATYEAKIK DVDEKADIAL IKIDHQGKLP     60
VLLLGRSSEL RPGEFVVAIG SPFSLQNTVT TGIVSTTQRG GKELGLRNSD MDYIQTDAII    120
NYGNSGGPLV NLDGEVIGIN TLKVTAGISF AIPSDKIKKF L                        161

SEQ ID NO: 12              moltype = DNA    length = 2138
FEATURE                    Location/Qualifiers
source                     1..2138
                           mol_type = genomic DNA
                           organism = Homo sapiens
SEQUENCE: 12
caatgggctg ggccgcgcgg ccgcgcgcac tcgcacccgc tgcccccgag gccctcctgc     60
actctcccg gcgccgctct ccggccctcg ccctgtccgc cgccaccgcc gccgccgcca    120
gagtcgccat gcagatcccg cgcgccgctc ttctcccgct gctgctgctg ctgctggcgg   180
cgcccgcctc ggcgcagctg tcccgggccg gccgctcgg gccttggcc gccgggtgcc    240
cagaccgctg cgagccggcg cgctgcccgc tgcagccgga gcactgcgag ggcggccggc   300
cccgggacgc gtgcggctgc tgcgaggcgt gcggcgcgcc cgagggcgcc gcgtgcggcc   360
tgcaggaggg cccgtgcggc gaggggctgc agtgcgtggt gcccttcggg gtgccagcct   420
cggccacggt gcggcggcgc gcgcaggccg gcctctgtgt gtgcgccagc agcgagcgg   480
tgtgcggcag cgacgccaac acctacgcca acctgtgcgc gctgcgcgcc gccagccgcc   540
gctccgagag gctgcaccgg ccgccggtca tcgtcctgca gcgcggagcc tgcggccaag   600
ggcaggaaga tcccaacagt ttgcgccata aatataactt tatcgcggac gtggtggaga   660
agatcgcccc tgccgtggtt catatcgaat tgtttcgcaa gcttccgttt tctaaacgag   720
aggtgccggt ggctagtggg tctggggttta ttgtgtcgga agatggactg atcgtgacaa   780
atgcccacgt ggtgaccaac aagcaccggg tcaaagttga gctgaagaac ggtgccactt   840
acgaagccaa aatcaaggat gtggatgaga aagcagacat cgcactcatc aaaattgacc   900
accagggcaa gctgcctgtc ctgctgcttg gccgctcctc agagctgcgg ccgggagagt   960
tcgtggtcgc catcggaagc ccgttttccc ttcaaaacac agtcaccacc gggatcgtga  1020
gcaccaccca gcgaggcggc aaagagctgg ggctccgcaa ctcagacatg gactacatcc  1080
agaccgacgc catcatcaac tatggaaact cgggaggccc gttagtaaac ctggacggtg  1140
aagtgattgg aattaacact ttgaaagtga cagctggaat ctccttttgca atcccatctg  1200
ataagattaa aaagttcctc acggagtccc atgaccgaca ggcaaagga aaagccatca  1260
ccaagaagaa gtatattggt atccgaatga tgtcactcac gtccagcaaa gccaagagc  1320
tgaaggaccg gcaccgggac ttcccagacg tgatctcagg agcgtatata attgaagtaa  1380
ttcctgatac cccagcagaa gctggtggtc tcaaggaaaa cgacgtcata atcagcatca  1440
atggacagtc cgtggtctcc gccaatgatg tcagcgacgt cattaaaagg gaaagcaccc  1500
tgaacatggt ggtccgcagg ggtaatgaag atatcatgat cacagtgatt cccgaagaaa  1560
ttgacccata gcagaggca tgagctggac ttcatgtttc cctcaaagac tctcccgtgg  1620
atgacggatg aggactctgg gctgctgaa taggacactc aagacttttg actgccattt  1680
tgttttgttca gtggagactc cctggccaac agaatcctcc ttgatagttt gcaggcaaaa  1740
caaatgtaat gttgcagatc cgcaggcaga agctctgccc ttctgtatcc tatgtatgca  1800
gtgtgctttt tcttgccagc ttgggccatt cttgcttaga cagtcagcat ttgtctcctc  1860
ctttaactga gtcatcatct tagtccaact aatgcagtcg atacaatgcg tagatagaag  1920
aagccccacg ggagccagga tgggactggt cgtgtttgtg cttttctcca agtcagcacc  1980
caaaggtcaa tgcacagaga ccccgggtgg gtgagccgtg gcttctcaaa cggccgaagt  2040
tgcctcttt aggaatctct ttggaattgg gagcacgatg actctgagtt tgagctatta  2100
aagtacttct tacacattgc aaaaaaaaaa aaaaaaaa                          2138

SEQ ID NO: 13              moltype = DNA    length = 8089
FEATURE                    Location/Qualifiers
source                     1..8089
                           mol_type = genomic DNA
                           organism = Homo sapiens
SEQUENCE: 13
gcggcgcgga ggctggcccg ggacgcgccc ggagcccagg gaaggaggga ggaggggagg     60
gtcgcgccg gccgccatgg ggccggggc ccgtggccgc cgccgccgcc gtcgcccgat    120
gtcgccgcca ccgccaccgc cacccgtgcg ggcgctgccc ctgctgctgc tgctagcggg   180
gccgggggct gcagccccc cttgcctgga cggaagcccg tgtgcaaatg gaggtcgttg    240
cacccagctg ccctcccggg aggctgcctg cctgtgcccg cctggctggg tgggtgagcg    300
gtgtcagctg gaggaccccct gtcactcagg ccctgtgct ggccgtggtg tctgccagag   360
```

```
ttcagtggtg gctggcaccg cccgattctc atgccggtgc ccccgtggct tccgaggccc    420
tgactgctcc ctgccagatc cctgcctcag cagcccttgt gcccacggtg cccgctgctc    480
agtggggccc gatggacgct tcctctgctc ctgcccacct ggctaccagg gccgcagctg    540
ccgaagcgac gtggatgagt gccgggtggg tgagccctgc cgccatggtg gcacctgcct    600
caacacacct ggctccttcc gctgccagtg tccagctgga tacacagggc cactatgtga    660
gaaccccgcg gtgccctgtg caccctcacc atgccgtaac gggggcacct gcaggcagag    720
tggcgacctc acttacgact gtgcctgtct tcctgggttt gagggtcaga attgtgaagt    780
gaacgtggac gactgtccag gacaccgatg tctcaatggg gggacatgcg tggatggcgt    840
caacacctat aactgccagt gccctcctga gtggacaggc cagttctgca cggaggacgt    900
ggatgagtgt cagctgcagc ccaacgcctg ccacaatggg ggtacctgct tcaacacgct    960
gggtggccac agctgcgtgt gtgtcaatgg ctggacaggc gagcctgca gtcagaatat    1020
cgatgactgt gccacagccg tgtgcttcca tggggccacc tgccatgacc gcgtggcttc    1080
tttctactgt gcctgcccca tgggcaagac tggcctcctg tgtcacctgg atgacgcctg    1140
tgtcagcaac ccctgccacg aggatgctat ctgtgcacaa aatccggtga acggccgtgc    1200
catttgcacc tgtcctcccg gcttcacggg tggggcatgt gaccaggatg tggacgagtg    1260
ctctatcggc gccaaccct gcgagcactt gggcaggtgc gtgaacacgc agggctcctt    1320
cctgtgccag tgcggtcgtg gctacactgg acctcgctgt gagaccgatg tcaacgagtg    1380
tctgtcgggg ccctgccgaa accaggccac gtgcctcgac cgcataggcc agttcacctg    1440
tatctgtatg gcaggcttca caggaaccta ttgcgaggtg gacattgacg agtgtcagag    1500
tagcccctgt gtcaacggtg gggtctgcaa ggaccgagtc aatggcttca gctgcacctg    1560
cccctcgggc ttcagcggct ccacgtgtca gctggacgtg gacgaatgcg ccagcacgcc    1620
ctgcaggaat ggcgccaaat gcgtcgacca gcccgatgcc tacgagtgcc gctgtgccga    1680
gggctttgag ggcacgctgt gtgatcgcaa cgtggacgac tgctcccctg acccatgcca    1740
ccatggtcgc tgccgtggatg gcatcgccag cttctcatgt gcctgtgctc ctggctacac    1800
gggcacacgc tgcgagagcc aggtggacga atgccgcagc cagccctgcc gccatggcgg    1860
caaatgccta gacctggtgg acaagtacct ctgccgctgc cccttctggga ccacaggtgt    1920
gaactgcgaa gtgaacattg acgactgtgc cagcaacccc tgcaccttg gagtctgccg    1980
tgatggcatc aaccgctacg actgtgtctg ccaacctggc ttcacagggc cctttgtaa    2040
cgtggagatc aatgagtgtg cttccagccc atgcggcgag ggaggttcct gtgtggatgg    2100
ggaaaatggc ttccgcttgc tctgcccgcc tggctccttg ccccactct gcctccccc    2160
gagccatccc tgtgcccatg agccctgcag tcacggcatc tgctatgatg cacctggccg    2220
gttccgctgt gtgtgtgagc ctggctgag tggccccgc tgcagccaga gcctggccg    2280
agacgcctgt gagtcccagc cgtgcagggc cggtgggaca tgcagcagcg atggaatggg    2340
tttccactgc acctgcccgc ctggtgtcca gggacgtcag tgtgaactcc tctccccctg    2400
caccccgaac ccctgtgagc atggggggcg ctgccctgcc agctgcctgt    2460
ctgctcctgc ccccagggct ggcaaggcc acgatgccag caggatgtgg acgagtgtgc    2520
tggccccgca ccctgtggcc ctcatggtat ctgcaccaac ctggcaggga gtttcagctg    2580
cacctgccat ggagggtaca ctggccccttc ctgcgatcag gacatcaatg actgtgaccc    2640
caaccatgc ctgaacggtg gctcgtgcca agacgcctgg ggctccttt cctgctcctg    2700
cctccctggt ttcgccggcc cacgatgcgc ccgcgatgtg gatgagtgcc tgagcaaccc    2760
ctgcggccg gcacctgta ccgaccacgt ggcctccttc acctgcacct gcccgccagg    2820
ctacggaggc ttccactgcg aacaggacct gcccgactgc agcccccagct cctgcttcaa    2880
tggccggacc tgtgtggacg gcgtgaactc gttcagctgc ctgtgccgtc cggctacac    2940
aggagcccac tgccaacatg aggcagaccc ctgcctctcg cggccctgcc tacacggggg    3000
cgtctgcagc gccgccaccc ctggcttccg ctgcacctgc ctcgagagct tcacgggccc    3060
gcagtgccag acgctggtgg attggtcag ccgccagcct tgtcaaaacg ggggtcgctg    3120
cgtccagact ggggccattt gccttttgtcc ccctggattgg agcggaccgc tctgtgacat    3180
ccgaagcttg ccctgcaggg aggccgcagc ccagatcggg gtgcggctgg agcagctgtg    3240
tcaggcgggt gggcagtgtg tggatgaaga cagctcccac tactgcgtgt gcccagaggg    3300
ccgtactggt agccactgtg agcaggaggt ggaccctgg tggcccagc cctgccagca    3360
tggggggacc tgccgtggct atatggggggg ctacatgtgt gagtgtcttc ctggctacaa    3420
tggtgataac tgtgaggacg acgtgcacga gtgtgcctcc cagccctgcc agcacggggg    3480
ttcatgcatt gacctcgtgg cccgctatct ctgctcctgt ccccaggaa cgctgggggt    3540
gctctgcgag attaatgagg atgactgcgg cccaggccca ccgctggact cagggccccg    3600
gtgcctacac aatggcaacct gcgtcgactt ggtgggtggt ttccgctgca cctgtcccct    3660
aggatacact ggtttggct gcgaggcaga catcaatgag tgtcgctcag gtgcctgcca    3720
cgcggcacac acccgggact gcctgcagga cccaggcgga ggtttcgtt gccttttgtca    3780
tgctggcttc tcaggtcctc gctgtcagac tgtcctgtct ccctgcgagt cccagccatg    3840
ccagcatgga ggccagtgcc gtcctagccc gggtcctggg ggtgggctga ccttcacctg    3900
tcactgtgcc cagccgttct ggggtcgacg ttgcgagcgg gtgccgcgct cctgccggga    3960
gctgcagtgc ccggtgggcg tccatgcca gcagacgccc cgcggccgc gctgcgcctg    4020
ccccccaggg ttgtcgggac cctcctgccg cagcttcccg gggtcgccgc cggggggcag    4080
caacgccagc tgcgcggccg cccctgtct ccacgggggg tcctgccgcc ccgcgccgct    4140
cgcccccttc ttccgctggg cttgcgcgca gggctggacc gggggcgacc gcgaggcgcc    4200
cgccgcggca cccgaggtct cggaggagcc gcgggtgcccg cgccgcgcct gcaggccaa    4260
gcgcggggac cagcggctgcg accgcgagtc aacagcccca ggctgcggct gggacgcgg    4320
cgactgctcg ctgagcgtgg cgaccccctg gcggcaatgc gaggcgctgc agtgctggcg    4380
cctcttcaac aacagccgct gcgaccccgc ctgcagcctg cccgcctgct tctacgacaa    4440
cttcgactgc cacgccggtg gccgcgagcg cacttgtcaac ccggtgtacg agaagtactg    4500
cgccgaccac tttgccgacg gccgctgcga ccagggctgc aacacggagg agtgcggctg    4560
ggatgggctg gattgtgcca gcgaggtgcc ggccctgctg gcccgcggcg tgctggtgct    4620
cacagtgctg ctgccgccag aggagctact gcgttccagc gccgactttc tgcagcggct    4680
cagcgccatc ctgcgcacct cgctgcgctt ccgcctggac gcgcacggcc aggccatggt    4740
cttccccttac caccggcctca gtcctggtc cgaaccccggg agctgcccc    4800
cgaggtgatc ggctcggtag taatgctgga gattgacaac cggtctctgcc tgcagtcgcc    4860
tgagaatgat cactgcttcc ccgatgccca gagcgccgct gactacctgg gagcgttgtc    4920
agcggtggag cgcctggact tcccgtaccc actgcgggac gtgcggggggg agccgctgga    4980
gcctccagaa cccagcgtcc cgctgctgcc actgctagtg gcgggcgctg tcttgctgct    5040
ggtcattctc gtcctgggtg tcatggtggc ccggcgcaag cgcgagcaca gcaccctctg    5100
```

-continued

```
gttccctgag ggcttctcac tgcacaagga cgtggcctct ggtcacaagg gccggcggga 5160
acccgtgggc caggacgcgc tgggcatgaa gaacatggcc aagggtgaga gcctgatggg 5220
ggaggtggcc acagactgga tggacacaga gtgcccagag gccaagcggc taaaggtaga 5280
ggagccaggc atgggggctg aggaggctgt ggattgccgt cagtggactc aacaccatct 5340
ggttgctgct gacatccgcg tggccaccagc catggccgca caccaccaac agggcgacgc 5400
agatgctgat ggcatggatg tcaatgtgcg tggcccagat ggcttcaccc cgctaatgct 5460
ggcttccttc tgtgggggg ctctggagcc aatgccaact gaagaggatg aggcagatga 5520
cacatcagct agcatcatct ccgacctgat ctgccagggg gctcagcttg ggcacggac 5580
tgaccgtact ggcgagactg ctttgcacct ggctgcccgt tatgcccgtg ctgatgcgag 5640
caagcggctg ctggatgctg gggcagacac caatgcccag gaccactcag gccgcactcc 5700
cctgcacaca gctgtcacag ccgatgccca gggtgtcttc cagattctca tccgaaaccg 5760
ctctacagac ttggatgccc gcatggcaga tggctcaacg gcactgatcc tggcggcccg 5820
cctggcagta gagggcatgg tggaagagct catcgccagc catgctgatg tcaatgtgt 5880
ggatgagctt gggaaatcag cctacactg gctggcggct gtgaacaacg tggaagccac 5940
tttggccctg ctcaaaaatg gagccaataa ggacatggac gatagcaagg aggacccc 6000
cctattcctg gccgcccgcg agggcagcta tgaggctgcc aagctgctgt ggaccactt 6060
tgccaaccgt gagatcaccg accacctgga caggctgccg cggacgtag cccaggagag 6120
actgcaccag gacatcgtgc gcttgctgga tcaacccagt gggccccgca gccccccgg 6180
tccccacggc ctggggcctc tgctctgtcc tccaggggcc ttcctccctg gcctcaaagc 6240
ggcacagtcg gggtccaaga agagcaggag gccccccggg aaggcggggc tggggccgca 6300
ggggccccgg ggcggggca agaagctgac gctggcctgc ccgggcccc tggctgacag 6360
ctcggtcacg ctgtcccccg tggactcgt ggactcctca cggcctttcg gtgggcccc 6420
tgcttcccct ggtggcttcc cccttgaggg gccctatgca gctgccactg ccactgcagt 6480
gtctctggca cagcttggtg gcccaggccg ggcgggtcta gggcgccagc ccctggagg 6540
atgtgtactc agcctgggcc tgctgaaccc tgtggctgtg ccctcgatt gggcccggct 6600
gcccccacct gccctccag gccctcgtt cctgctgcca ctggcgccgg gaccccagct 6660
gctcaaccca gggaccccg tctcccgca ggagcggccc ccgccttacc tggcagtccc 6720
aggacatggc gaggagtacc cggcggctgg ggcacacagc agcccccaa aggcccgctt 6780
cctgcgggtt cccagtgagc acccttacct gacccccatcc cccgaatccc ctgagcactg 6840
ggccagcccc tcacctccct ccctctcaga ctggtccgaa tccacgccta gccagccag 6900
tgccactggg gccatggcca ccaccactgg ggcactggct gccagccac ttcccttgtc 6960
tgttcccagc tcccttgctc aggcccagac ccagctgggg cccagccgg aagttacccc 7020
caagaggcaa gtgttggcct gagacgtcg tcagttctta gatcttgggg gcctaaagag 7080
accccccgtcc tcctccttt ctttctctgt ctctccttc cttttagtct ttttcatcct 7140
cttctcttc caccaacct cctgcatcct tgccttgcag cgtgaccgag ataggtcatc 7200
agcccagggc ttcagtcttc ctttatttat aatgggtggg ggctaccacc cacctctca 7260
gtcttgtgaa gagtctggga cctccttctt ccccactcct ctcttccctc attcctttct 7320
ctctcctttct ggcctctcat ttccttacac tctgacatga atgaattatt attattta 7380
tttttttt ttttttaca ttttgtatag aaacaaattc atttaaacaa acttattatt 7440
attattttt acaaaatata tatatgaga tgctccctcc ccctgtgaac cccccagtgc 7500
ccccgtggg ctgagtctgt gggcccattc ggccaagctg gattctgtgt acctagtaca 7560
caggcatgac tgggatcccg tgtaccgagt acacgaccca ggtatgtacc aagtaggcac 7620
cttgggac acccactggg gccaggggtc ggggagtgt tgggagcctc ctccccaccc 7680
caccctcccctc acttcactgc attcagatg ggacatgttc catagccttg ctggggaagg 7740
gcccactgcc aactcccctct gccccagccc caccccttggc catctccctt tgggaactag 7800
gggctgctg gtgggaaatg ggagccaggg cagatgtatg cattccttt gtgccctgta 7860
aatgtgggac tacaagaaga gggagctgcct gagtggtact ttctcttcct ggtaatcctc 7920
tggcccagcc tcatggcaga atagaggtat ttttaggcta tttttgtaat atggcttctg 7980
gtcaaaatcc ctgtgtagct gaattcccaa gccctgcatt gtacagcccc ccactcccct 8040
caccacctaa taaggaata gttaacactc aaaaaaaaaa aaaaaaaa 8089

SEQ ID NO: 14           moltype = AA  length = 2321
FEATURE                 Location/Qualifiers
source                  1..2321
                        mol_type = protein
                        organism = Homo sapiens
SEQUENCE: 14
MGPGARGRRR RRRPMSPPPP PPPVRALPLL LLLAGPGAAA PPCLDGSPCA NGGRCTQLPS    60
REAACLCPPG WVGERCQLED PCHSGPCAGR GVCQSSVVAG TARFSCRCPR GFRGPDCSLP   120
DPCLSSPCAH GARCSVGPDG RFLCSCPPGY QGRSCRSDVD ECRVGEPCRH GGTCLNTPGS   180
FRCQCPAGYT GPLCENPAVP CAPSPCRNGG TCRQSGDLTY DCACLPGFEG QNCEVNVDDC   240
PGHRCLNGGT CVDGVNTYNC QCPPEWTGQF CTEDVDECQL QPNACHNGGT CFNTLGGHSC   300
VCVNGWTGES CSQNIDDCAT AVCFHGATCH DRVASFYCAC PMGKTGLLCH LDDACVSNPC   360
HEDAICDTNP VNGRAICTCP PGFTGGACDQ DVDECSIGAN PCEHLGRCVN TQGSFLCQCG   420
RGYTGPRCET DVNECLSGPC RNQATCLDRI GQFTCICMAG FTGTYCEVDI DECQSSPCVN   480
GGVCKDRVNG FSCTCPSGFS GSTCQLDVDE CASTPCRNGA KCVDQPDGYE CRCAEGFEGT   540
LCDRNVDDCS PDPCHHGRCV DGIASFSCAC APGYTGTRCE SQVDECRSQP CRHGGKCLDL   600
VDKYLCRCPS GTTGVNCEVN IDDCASNPCT FGVCRDGINR YDCVCQPGFT GPLCNVEINE   660
CASSPCGEGG SCVDGENGFR CLCPPGSLPP LCLPPSHPCA HEPCSHGICY DAPGGFRCVC   720
EPGWSGPRCS QSLARDACES QPCRAGGTCS SDGMGFHCTC PPGVQGRQCE LLSPCTPNPC   780
EHGGRCESAP GQLPVCSCPQ GWQGPRCQQD VDECAGPAPC GPHGICTNLA GSFSCTCHGG   840
YTGPSCDQDI NDCDPNPCLN GGSCQDGVGS FSCSCLPGFA GPRCARDVDE CLSNPCGPGT   900
CTDHVASFTC TCPPGYGGFH CEQDLPDCSP SSCFNGGTCV DGVNSFSCLC RPGYTGAHCQ   960
HEADPCLSRP CLHGGVCSAA HPGFRCTCLE SFTGPQCQTL VDWCSRQPCQ NGGRCVQTGA  1020
YCLCPPGWSG RLCDIRSLPC REAAAQIGVR LEQLCQAGGQ CVDEDSSHYC VCPEGRTGSH  1080
CEQEVDPCLA QPCQHGGTCR GYMGGYMCEC LPGYNGDNCE DDVDECASQP CQHGGSCIDL  1140
VARYLCSCPP GTLGVLCEIN EDDCGPGPPL DSGPRCLHNG TCVDLVGGFR CTCPPGYTGL  1200
RCEADINECR SGACHAAHTR DCLQDPGGGF RCLCHAGFSG PRCQTVLSPC ESQPCQHGGQ  1260
CRPSPGPGGG LTFTCHCAQP FWGPRCERVA RSCRELQCPV GVPCQQTPRG PRCACPPGLS  1320
```

-continued

```
GPSCRSFPGS PPGASNASCA AAPCLHGGSC RPAPLAPFFR CACAQGWTGP RCEAPAAAPE 1380
VSEEPRCPRA ACQAKRGDQR CDRECNSPGC GWDGGDCSLS VGDPWRQCEA LQCWRLFNNS 1440
RCDPACSSPA CLYDNFDCHA GGRERTCNPV YEKYCADHFA DGRCDQGCNT EECGWDGLDC 1500
ASEVPALLAR GVLVLTVLLP PEELLRSSAD FLQRLSAILR TSLRFRLDAH GQAMVFPYHR 1560
PSPGSEPRAR RELAPEVIGS VVMLEIDNRL CLQSPENDHC FPDAQSAADY LGALSAVERL 1620
DFPYPLRDVR GEPLEPPEPS VPLLPLLVAG AVLLLVILVL GVMVARRKRE HSTLWFPEGF 1680
SLHKDVASGH KGRREPVGQD ALGMKNMAKG ESLMGEVATD WMDTECPEAK RLKVEEPGMG 1740
AEEAVDCRQW TQHHLVAADI RVAPAMALTP PQGDADADGM DVNVRGPDGF TPLMLASFCG 1800
GALEPMPTEE DEADDTSASI ISDLICQGAQ LGARTDRTGE TALHLAARYA RADAAKRLLD 1860
AGADTNAQDH SGRTPLHTAV TADAQGVFQI LIRNRSTDLD ARMADGSTAL ILAARLAVEG 1920
MVEELIASHA DVNAVDELGK SALHWAAAVN NVEATLALLK NGANKDMQDS KEETPLFLAA 1980
REGSYEAAKL LLDHFANREI TDHLDRLPRD VAQERLHQDI VRLLDQPSGP RSPPGPHGLG 2040
PLLCPPGAFL PGLKAAQSGS KKSRRPPGKA GLGPQGPRGR GKKLTLACPG PLADSSVTLS 2100
PVDSLDSPRP FGGPPASPGG FPLEGPYAAA TATAVSLAQL GGPGRAGLGR QPPGGCVLSL 2160
GLLNPVAVPL DWARLPPPAP PGPSFLLPLA PGPQLLNPGT PVSPQERPPP YLAVPGHGEE 2220
YPVAGAHSSP PKARFLRVPS EHPYLTPSPE SPEHWASPSP PSLSDWSEST PSPATATGAM 2280
ATTTGALPAQ PLPLSVPSSL AQAQTQLGPQ PEVTPKRQVL A                    2321
```

BLOOD BIOMARKERS AND DIAGNOSTIC METHODS FOR SMALL VESSEL DISEASES

RELATED APPLICATIONS

This application is a continuation of U.S. patent application Ser. No. 16/499,192, filed Sep. 27, 2019, which is a national stage application filed under 35 U.S.C. § 371, of International Patent Application No. PCT/US2018/024394, filed Mar. 26, 2018, which claims the benefit of and priority to U.S. Provisional Patent Application No. 62/477,274, filed Mar. 27, 2017, the entire contents of each of which are incorporated herein by reference.

STATEMENT AS TO FEDERALLY SPONSORED RESEARCH

This invention was made with government support under R01EY005318 and R00EY021624 and P30EY003790 awarded by the National Institutes of Health. The government has certain rights in the invention.

SEQUENCE LISTING

This application contains a Sequence Listing that has been submitted electronically as an XML file named "00633-0307002_SL_ST26.XML." The XML file, created on Nov. 22, 2022, is 43,199 bytes in size. The material in the XML file is hereby incorporated by reference in its entirety.

FIELD OF THE INVENTION

The present invention relates to therapeutics and diagnostics for small vessel diseases.

BACKGROUND

Currently, there are no diagnostic or prognostic biomarkers for small vessel diseases (SVDs). SVDs include very prevalent conditions affecting richly perfused tissues like the retina, brain, heart and the kidney. In the brain, SVD is a prevalent neurological condition, a major contributor to the presence of covert strokes, and a strong contributor to stroke susceptibility and vascular cognitive impairment and dementia. In the retina, SVD is a main contributor to blindness in diabetic individuals in a condition known as diabetic retinopathy and also has been shown to play a role in age-related macular degeneration (AMD).

SVD is more common in women and in people who have diabetes or high blood pressure. The condition is treatable but can be difficult to detect (www.mayoclinic.org/diseases-conditions/small-vessel-disease/home/ovc-20198376). In those suffering from diabetes, SVD (e.g., microvascular disease) includes nephropathy, retinopathy, and neuropathy. Diabetes is one of the most common endocrine disorders in the world; it affected roughly 6% of the global population ca. in the year 2000, and an estimated 300 million people in 2025. Diabetic retinopathy affects 35% of the patients in the diabetic population and is the main cause of permanent vision loss (Cade W T, Phys Ther. 2008; 88(11): 1322-1335). Cerebral SVD is perhaps among the most common pathologies in the aging brain, primarily affecting the small perforating arteries and arterioles in the cortex and underlying structures of the white and deep gray matter. Vascular disease of the brain is the third leading cause of death and the leading cause of severe long-term disability in the United States (Auriat et al., Front Neurol. 2015; 6: 175).

Biomarkers, diagnostic tests, and therapeutic regimens for SVDs are needed.

SUMMARY OF THE INVENTION

The present subject matter provides, inter alia, methods, compositions, devices, systems, and kits for detecting Neurogenic Locus Notch Homolog Protein 3 (NOTCH3), collagen18α1 or endostatin, insulin-like growth factor binding protein 1 (IGFBP-1), and/or High-Temperature Requirement A Serine Peptidase 1 (HTRA1) in a test sample obtained from a subject. In some embodiments, these proteins are detected as individual proteins and in some embodiments these proteins are detected as bound to each other. A difference (increase or decrease) in the level of one or more of these markers compared to a normal control indicates the presence or risk of a small vessel disease (SVD). For example, a decrease in the level of HTRA1 indicates that a subject has or is at risk of developing cerebral autosomal recessive arteriopathy with subcortical infarcts and leukoencephalopathy (CARASIL), whereas an increase in the level of HTRA1 indicates that a subject has or is at risk of developing cerebral autosomal-dominant arteriopathy with subcortical infarcts and leukoencephalopathy (CADASIL).

In some embodiments, an assay to measure amounts or levels of biomarkers such as those described above comprise an enzyme immunoassay (EIA). In some embodiments, the assay comprises an enzyme-linked immunosorbent assay, a (ELISA), a Western blot, a mass spectrometry assay, a radioimmunoassay, or a fluoroimmunoassay.

An aspect included herein provides a method for assessing NOTCH signaling comprising detecting the level of collagen18α1/endostatin and/or NOTCH3. In some embodiments, the level of collagen18α1/endostatin is increased. In certain embodiments, the level of collagen18α1/endostatin is decreased. In various embodiments, the level of NOTCH3 is increased. In some embodiments, the level of NOTCH3 is decreased.

An aspect provides a method for diagnosing a SVD in a subject comprising assaying the level of collagen18α1/endostatin, IGFBP-1, HTRA1, and/or NOTCH3 in a test sample from a subject; and diagnosing the subject with the SVD if the level of collagen18α1/endostatin, IGFBP-1, HTRA1, and/or NOTCH3 is increased or reduced in the test sample compared to the normal control. In some embodiments, the subject with the SVD is diagnosed with a SVD if the level of collagen18α1/endostatin is increased in the test sample compared to the normal control. In examples, the subject with the SVD is diagnosed with a SVD if the level of the complex of NOTCH3 complexed with itself, and/or with HTRA1 and/or IGFBP-1 is increased in the test sample compared to the normal control. In examples, the subject with the SVD is diagnosed with a SVD if the level of the complex of NOTCH3 complexed with itself, and/or with HTRA1 and/or IGFBP-1 is decreased in the test sample compared to the normal control.

In certain embodiments, the subject with the SVD is diagnosed with a SVD if the level of collagen18α1/endostatin is increased in the test sample compared to the normal control. In some embodiments, the subject with the SVD is diagnosed with a SVD if the level of IGFBP-1 is increased in the test sample compared to the normal control. In certain embodiments, the subject with the SVD is diagnosed with a SVD if the level of IGFBP-1 is increased in the test sample compared to the normal control. In some embodiments, the subject with the SVD is diagnosed with a SVD if the level of HTRA1 is increased in the test sample compared to the normal control. In certain embodiments, the subject with the SVD is diagnosed with a SVD if the level of HTRA1 is increased in the test sample compared to the normal control. In some embodiments, the subject with the SVD is diagnosed with a SVD if the level of NOTCH3 is increased in the test sample compared to the normal control. In certain embodiments, the subject with the SVD is diagnosed with a SVD if the level of NOTCH3 is increased in the test sample compared to the normal control.

An aspect provides a method for diagnosing a SVD in a subject comprising assaying the level of collagen18α1/endostatin, IGFBP-1, HTRA1, and/or NOTCH3 in a test sample from a subject; and diagnosing the subject with the SVD if (i) the level of collagen18α1/endostatin, IGFBP-1, and/or HTRA1 is elevated in the test sample compared to a normal control, and/or (ii) the level of NOTCH3 is reduced in the test sample compared to the normal control.

In various embodiments, detecting collagen18α1/endostatin, IGFBP-1, HTRA1, and/or NOTCH3 or the level thereof comprises detecting collagen18α1/endostatin, IGFBP-1, HTRA1, or NOTCH3 protein or the level thereof, respectively. In various embodiments, detecting collagen18α1/endostatin, IGFBP-1, HTRA1, and/or NOTCH3 or the level thereof comprises detecting mRNA that encodes collagen18α1/endostatin, IGFBP-1, HTRA1, or NOTCH3 protein or the level thereof, respectively.

In various embodiments, the subject is diagnosed with the SVD if (i) the level of collagen18α1/endostatin, IGFBP-1, and/or HTRA1 is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in said test sample compared to a normal control; and/or (ii) the level of NOTCH3 reduced by about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% in said test sample compared to a normal control.

In an aspect, included herein is a method for assessing the level of NOTCH signaling (e.g., NOTCH3 signaling) comprising detecting the level of collagen18α1/endostatin and/or an extracellular domain of NOTCH3 (e.g., N3ECD) in a subject. In various embodiments, an increased level of collagen18α1/endostatin and/or an extracellular domain of NOTCH3 indicates an increased level of NOTCH3 signaling. In some embodiments, a decreased level of collagen18α1/endostatin and/or an extracellular domain of NOTCH3 indicates a decreased level of NOTCH3 signaling.

In an aspect, provided herein is a method of detecting a protein-protein interaction, comprising detecting NOTCH3 binding to collagen18α1/endostatin, IGFBP-1, and/or HTRA1 in a test sample from a subject. In some embodiments, the protein-protein interaction is an aberrant protein-protein interaction. In certain embodiments, the method further comprises diagnosing the subject as having an SVD (such as CADASIL) if NOTCH3 is binding to collagen18α1/endostatin, IGFBP-1, and/or HTRA1 is detected in the sample. Such interactions can be present in normal subject (i.e., those known not to comprise SVD).

In some embodiments, a test sample obtained from the subject comprises a level of NOTCH3 protein bound to collagen18α1 and/or endostatin and/or HTRA1 and/or IGFBP-1 that is different than a normal control. For example, the test sample may comprise levels of NOTCH3 protein bound to collagen18α1 and/or endostatin and/or HTRA1 and/or IGFBP-1 that is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in the test sample compared to a normal control.

In some embodiments, the ratio of HTRA1 to NOTCH3 differs compared to a normal control.

In certain embodiments, the ratio of HTRA1 to NOTCH3 is at least about 1.5 to 1, 2 to 1, 2.5 to 1, 3 to 1, 4 to 1, or 5 to 1. In some embodiments, a ratio of HTRA1 to NOTCH3 is at least about 1.5 to 1, 2 to 1, 2.5 to 1, 3 to 1, 4 to 1, or 5 to 1 identifies a subject as having a SVD such as CADASIL.

Aspects of the present subject matter also provide a method for identifying whether a subject is at risk of developing a SVD comprising (a) providing a test sample from said subject; (b) assaying the level of collagen18α1 or endostatin, IGFBP-1, HTRA1, and/or NOTCH3 in the test sample; and (c) identifying the subject as at risk of developing the SVD if (i) the level of collagen18α1/endostatin, IGFBP-1, and/or HTRA1 is elevated in the test sample compared to a normal control, and/or (ii) the level of NOTCH3 is reduced in the test sample compared to the normal control.

In various embodiments, the subject is identified as at risk of developing the SVD if (i) the level of collagen18α1 or endostatin, IGFBP-1, and/or HTRA1 is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in said test sample compared to a normal control; and/or (ii) the level of NOTCH3 reduced by about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% in said test sample compared to a normal control. In some examples, endostatin levels can also be reduced in SVD, e.g., depending on the age and on the status of NOTCH3 activity. Endostatin may be reduced in a situation in which NOTCH3 signaling is reduced e.g., in a situation in which NOTCH3 has a stop codon and there is haploinsufficiency.

In some embodiments, a method provided herein further comprises directing the subject to obtain (i) additional screening or an additional diagnostic test for the SVD if the subject is identified as at risk of developing the SVD; or (ii) treatment to reduce, delay, or prevent the onset or progression of the SVD.

Aspects of the present subject matter also provide a method for monitoring whether a SVD is progressing in a subject who has been diagnosed with the SVD, comprising periodically determining the level of collagen18α1 or endostatin, IGFBP-1, HTRA1, and/or NOTCH3 in the subject, and (1) identifying the SVD as worsening if (i) the level of collagen18α1 or endostatin, IGFBP-1, and/or HTRA1 increases over time, and/or (ii) the level of NOTCH3 decreases over time; (2) identifying the SVD as improving if (i) the level of collagen18α1/endostatin, IGFBP-1, and/or HTRA1 decreases over time, and/or (ii) the level of NOTCH3 increases over time; or (3) identifying the SVD as neither worsening nor improving if the level of collagen18α1/endostatin, IGFBP-1, HTRA1, and/or NOTCH3 remains the same or about the same over time, wherein determining the level of collagen18α1/endostatin, IGFBP-1, HTRA1, and/or NOTCH3 comprises (a) providing a test sample from said subject; and (b) assaying the level of collagen18α1/endostatin, IGFBP-1, HTRA1, and/or NOTCH3 in the test sample.

In some embodiments, the level of collagen18α1/endostatin, IGFBP-1, NOTCH3, and/or HTRA1 is determined at least about 1, 2, 3, 4, 5, 6, 7, 8, 9, 10 or more times and/or at least once every 1, 2, 3, or 4 weeks; at least once every 1, 2, 3, 4, 5, or 6 weeks; or at least once every 1, 2, 3, 4, or 5 years.

The present subject matter also provides a method for identifying a prognosis for a subject who has been diagnosed with a SVD comprising (a) providing a test sample from said subject; (b) assaying the level of collagen18α1 or endostatin, IGFBP-1, HTRA1, and/or NOTCH3 in the test sample; and (c) comparing the level of collagen18α1/endostatin, IGFBP-1, HTRA1, and/or NOTCH3 determined in (b) to a value in a database to identify the subject's risk of suffering from a symptom of SVD. In some embodiments, the database contains (i) collagen18α1/endostatin, IGFBP-1, HTRA1, and/or NOTCH3 level values from subjects who have suffered from said symptom of SVD; or (ii) absolute or relative risk values calculated based on collagen18α1/endostatin, IGFBP-1, HTRA1, and/or NOTCH3 level values from subjects who have suffered from said symptom of SVD. In certain embodiments, the absolute or relative risk values comprise mean or median level values calculated using collagen18α1/endostatin, IGFBP-1, HTRA1, and/or NOTCH3 level values from subjects who have suffered from said symptom of SVD.

Aspects of the present subject matter also provide a method of prophylaxis for a SVD, comprising identifying whether a subject is at risk of suffering from SVD according to a method provided herein, and administering to the subject a compound that is used to treat the SVD if the subject is identified as at risk of suffering from SVD. In some embodiments, the compound comprises a an anti-angiogenic compound, an anti-vascular endothelial growth factor (VEGF) compound, an anti-platelet compound, an antihypertensive compound, a platelet antiaggregant, a cholesterol-lowering compound, a 3-hydroxy-3-methylglutaryl coenzyme A (HMG-CoA) reductase inhibitor, nimodipine, propentofylline, posatirelin, bevacizumab, ranibizumab, pegaptanib, aflibercept, nicardipine, verteporfin, anecortave acetate, triamcinolone acetonide, aspirin, dipyridamole, ticlopidine, or clopidogrel.

Aspects provide methods for determining whether thrombolytic therapy should be administered to a subject who has or is suspected of having a stroke (e.g., the subject has a symptom such as 1 or more or any combination of drooping of or numbness in one side of the face, inability to smile evenly, asymmetric weakness or numbness such as in the arms, slurred speech, speech loss, difficulty speaking, limping, confusion, blurred vision, sudden visual loss, vertigo, or rapid involuntary eye movement). Thrombolytic therapy is indicated for acute treatment of ischemic stroke with a short therapeutic window of 3 hours after stroke onset. A non-limiting example of thrombolytic therapy includes Activase® (Alteplase) (a recombinant tissue plasminogen activator, tPA). tPA therapy is contraindicated in patients with CADASIL. There is a clinical need to rule out CADASIL in patients presenting with ischemic stroke and unknown history of CADASIL. In various embodiments, a subject is not administered a thrombolytic therapy if (i) the level of collagen18α1/endostatin, IGFBP-1, and/or HTRA1 is elevated in a test sample from the subject compared to a normal control, and/or (ii) the level of NOTCH3 is reduced in the test sample compared to the normal control.

The present subject matter also provides a method for adjusting the dose of a compound that is administered to a subject during a treatment regimen for a SVD, comprising periodically determining the level of collagen18α1 or endostatin, IGFBP-1, HTRA1, and/or NOTCH3 in the subject, and (1) increasing the dose of the compound if (i) the level of collagen18α1/endostatin, IGFBP-1, and/or HTRA1 increases over time, and/or (ii) the level of NOTCH3 decreases over time; (2) maintaining or decreasing the dose of the compound if (i) the level of collagen18α1/endostatin, IGFBP-1, and/or HTRA1 decreases over time, and/or (ii) the level of NOTCH3 increases over time; or (3) maintaining or increasing the dose of the compound if the level of collagen18α1/endostatin, IGFBP-1, HTRA1, and/or NOTCH3 remains the same or about the same over time, wherein determining the level of collagen18α1/endostatin, IGFBP-1, HTRA1, and/or NOTCH3 comprises (a) providing a test sample from said subject; and (b) assaying the level of collagen18α1/endostatin, IGFBP-1, HTRA1, and/or NOTCH3 in the test sample.

Aspects of the present subject matter provide method for identifying whether a therapy has reduced or ameliorated a SVD in a subject comprising (a) providing a pre-therapy test sample from said subject; (b) assaying the pre-therapy level of collagen18α1 or endostatin, IGFBP-1, HTRA1, and/or NOTCH3 in the pre-therapy test sample; (c) administering the therapy to the subject; (d) providing a post-therapy test sample from said subject; (e) assaying the post-therapy level of collagen18α1/endostatin, IGFBP-1, HTRA1, and/or NOTCH3 in the post-therapy test sample; and (f) identifying the therapy as having reduced or ameliorated said SVD if (i) the level of collagen18α1/endostatin, IGFBP-1, and/or HTRA1 in the post-therapy test sample is lower than the level of collagen18α1/endostatin, IGFBP-1, and/or HTRA1 in the pre-therapy test sample, and/or (ii) the level of NOTCH3 in the post-therapy test sample is higher than the level of NOTCH3 in the pre-therapy test sample.

In some embodiments, the SVD comprises Age-Related Macular Degeneration (AMD).

In some embodiments, the level of collagen18α1/endostatin, IGFBP-1, HTRA1, and/or NOTCH3 is the level of collagen18α1/endostatin and HTRA1.

In some embodiments, the method does not comprise assaying and/or detecting HTRA 1.

In some embodiments, the method does not comprise assaying and/or detecting IGFBP-1.

In some embodiments, the NOTCH3 is an extracellular portion of NOTCH3. For example, the extracellular portion of NOTCH3 may be the NOTCH3 extracellular domain (N3ECD).

In some embodiments, the test sample comprises a bodily fluid from said subject. In some embodiments, the bodily fluid includes whole blood, a component of whole blood, plasma, serum. In some embodiments, the body fluid comprises tears, vitreous, cerebrospinal fluid, sweat, cerebrospinal fluid, or urine. In some embodiments, the test sample is other than a tissue biopsy.

In some embodiments, the subject does not contain a mutated HTRA1 gene.

In some embodiments, the method does not comprise assaying and/or detecting the level of Fas ligand (FasL).

In some embodiments, the SVD comprises cerebral SVD. In some embodiments, the SVD comprises a stroke, vascular cognitive impairment, dementia, microangiopathy, nephropathy, retinopathy, or neuropathy.

In some embodiments, the SVD comprises CARASIL, age-related macular degeneration (AMD), CADASIL, retinopathy such as diabetic retinopathy, skin microangiopathy, heart small vessel disease, coronary microangiopathy, proximal 19p13.12 microdeletion syndrome, myocardial ischemia, nephropathy or another SVD of the kidney, microangiopathy, Alagille syndrome, familial tetralogy of Fallot, patent ductus arteriosus, a cerebral cavernous malformation, a HTRA1-associated small vessel disease, pulmonary arterial hypertension, or heart failure.

In some embodiments, the SVD comprises AMD and the AMD is dry AMD or wet AMD.

In some embodiments, the subject has diabetes, high blood pressure, or dyslipidemia.

In some embodiments, assaying the level of collagen18α1/endostatin, IGFBP-1, HTRA1, and/or NOTCH3 comprises contacting said collagen18α1/endostatin, IGFBP-1, HTRA1, and/or NOTCH3 with an collagen18α1/endostatin-specific, IGFBP-1-specific, HTRA1-specific and/or NOTCH3-specific binding agent.

In some embodiments, the binding agent comprises an antibody or a fragment thereof, or a polypeptide or a fragment thereof. In some embodiments, the binding agent comprises an antibody or a fragment thereof. In some embodiments, the antibody comprises an anti-collagen18α1/endostatin antibody, an anti-IGFBP-1 antibody, an anti-HTRA1 antibody or an anti-NOTCH3 antibody. In some embodiments, the antibody or fragment thereof is attached to a solid support.

In certain embodiments, detecting the level of a protein comprises immunoprecipitating the protein and then measuring the level of the protein by mass spectrometry. In various embodiments, assaying comprises high-performance liquid chromatography (HPLC), liquid chromatography-mass spectrometry (LC/MS), protein immunoprecipitation, immunoelectrophoresis, or protein immunostaining. General descriptions relating to the measurement of biomarkers by immunoprecipitation coupled with mass spectrometry provided in Nakamura et al. (2018) *Nature* 2018 Feb. 8; 554(7691):249-254, the entire content of which is incorporated herein by reference.

In some embodiments, assaying comprises imaging of a marker in a subject, such as by using an ultrasound, a computerized tomography (CT) scans, an X-ray, magnetic resonance imaging (MRI), positron emission tomography (PET), or single-photon emission computed tomography (SPECT). Such assays may be used to detect the presence or level of collagen18α1/endostatin, IGFBP-1, HTRA1, and/or NOTCH3 within and/or differing between, e.g., a bodily fluid such as blood, cerebrospinal fluid, or lymph, and/or a tissue such as muscle, nervous, or blood vessel tissue.

In vivo imaging of collagen18α1/endostatin, IGFBP-1, HTRA1, and/or NOTCH3 may be performed by any suitable technique. For example, Technetium-99, 99Tc-labeling or labeling with another β-ray emitting isotope may be used to label a binding agent (e.g., an antibody or a fragment thereof, a peptide such as a ligand or a fragment thereof, or a molecule having a molecular weight of less than about 2000 daltons) that is specific for collagen18α1/endostatin, IGFBP-1, HTRA1, and/or NOTCH3. Variations on this technique may include the use of magnetic resonance imaging (MRI) to improve imaging over gamma camera techniques. Similar immunoscintigraphy methods and principles are described in, e.g., Srivastava (ed.), Radiolabeled Monoclonal Antibodies For Imaging And Therapy (Plenum Press 1988), Chase, "Medical Applications of Radioisotopes," in Remington's Pharmaceutical Sciences, 18th Edition, Gennaro et al., (eds.), pp. 624-652 (Mack Publishing Co., 1990), and Brown, "Clinical Use of Monoclonal Antibodies," in Biotechnology And Pharmacy 227-49, Pezzuto et al., (eds.) (Chapman & Hall 1993). In certain embodiments, imaging of collagen18α1/endostatin, IGFBP-1, HTRA1, and/or NOTCH3 comprises PET or SPECT.

In some embodiment, the present invention provides an in vivo imaging method wherein a binding agent is conjugated to a detection-promoting agent, the conjugated binding agent is administered to a host, such as by injection into the bloodstream, and the presence and location of the labeled binding agent in the host is assayed. Through this technique and any other diagnostic method provided herein, the present invention provides a method for determining the level and/or location of collagen18α1 or endostatin, IGFBP-1, HTRA1, and/or NOTCH3 in a human patient or a biological sample taken from a human patient.

For diagnostic imaging, radioisotopes may be bound to a binding agent either directly, or indirectly by using an intermediary functional group. Useful intermediary functional groups include chelators, such as ethylenediaminetetraacetic acid and diethylenetriaminepentaacetic acid (see for instance U.S. Pat. No. 5,057,313). In such diagnostic assays involving radioisotope-conjugated binding agents, the dosage of conjugated binding agent delivered to the patient typically is maintained at as low a level as possible through the choice of isotope for the best combination of minimum half-life, minimum retention in the body, and minimum quantity of isotope, which will permit detection and accurate measurement.

In addition to radioisotopes and radio-opaque agents, diagnostic methods may be performed using binding agents that are conjugated to dyes (such as with the biotin-streptavidin complex), contrast agents, fluorescent compounds or molecules and enhancing agents (e.g. paramagnetic ions) for magnetic resonance imaging (MRI) (see, e.g., U.S. Pat. No. 6,331,175, which describes MRI techniques and the preparation of antibodies conjugated to a MRI enhancing agent). Such diagnostic/detection agents may be selected from agents for use in magnetic resonance imaging, and fluorescent compounds.

In order to load a protein binding agent (such as an antibody, a ligand, or a fragment of a ligand or an antibody) with radioactive metals or paramagnetic ions, it may be necessary to react it with a reagent having a long tail to which are attached a multiplicity of chelating groups for binding the ions. Such a tail may be a polymer such as a polylysine, polysaccharide, or other derivatized or derivatizable chain having pendant groups to which can be bound chelating groups such as, e.g., porphyrins, polyamines, crown ethers, bisthiosemicarbazones, polyoximes, and like groups known to be useful for this purpose.

Chelates may be coupled to binding agents using standard chemistries. In the case of antibodies and antibody fragments, a chelate is normally linked by a group that enables formation of a bond to the molecule with minimal loss of immunoreactivity and minimal aggregation and/or internal cross-linking.

Examples of potentially useful metal-chelate combinations include 2-benzyl-DTPA and its monomethyl and cyclohexyl analogs, used with diagnostic isotopes in the general energy range of 60 to 4,000 keV, such as $^{125}$I, $^{123}$I, $^{124}$I, $^{62}$Cu, $^{64}$Cu, $^{18}$F, $^{111}$In, $^{67}$Ga, $^{99}$Tc, $^{94}$Tc, $^{11}$C, $^{13}$N, $^{5}$O, and $^{76}$Br for radio-imaging.

Labels include a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{110}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94}$mTc, $^{94}$Tc, $^{99}$mTc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52}$mMn, $^{55}$Co, $^{72}$As, $^{75}$Br, $^{76}$Br, $^{82}$mRb, $^{83}$Sr, or other γ-, β-, or positron-emitters.

Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III).

Ultrasound contrast agents may comprise liposomes, such as gas filled liposomes. Radiopaque diagnostic agents may be selected from compounds, barium compounds, gallium compounds, and thallium compounds.

These and similar chelates, when complexed with non-radioactive metals, such as manganese, iron, and gadolinium may be useful for MRI diagnostic methods in connection with binding agents. Macrocyclic chelates such as NOTA, DOTA, and TETA are of use with a variety of metals and radiometals, most particularly with radionuclides of gallium, yttrium, and copper, respectively. Such metal-chelate complexes may be made very stable by tailoring the ring size to the metal of interest. Other ring-type chelates such as macrocyclic polyethers, which are of interest for stably binding nuclides, such as 223Ra may also be suitable in diagnostic methods.

Thus, the present invention provides diagnostic binding agent conjugates, wherein the binding agent conjugate is conjugated to a contrast agent (such as for magnetic resonance imaging, computed tomography, or ultrasound contrast-enhancing agent) or a radionuclide that may be, for example, a γ-, β-, α-, Auger electron-, or positron-emitting isotope.

In some embodiments, the binding agent comprises a nucleic acid molecule, such as a sequence that is complementary to mRNA or cDNA produced from mRNA that encodes collagen18α1/endostatin, IGFBP-1, HTRA1 or NOTCH3. In some aspects, the present subject matter provides a composition utilizing a binding agent, wherein the binding agent is attached to a solid support, (e.g., a strip, a polymer, a bead, a nanoparticle, a plate such as a multiwell plate, or an array such as a microarray). In embodiments relating to the use of a nucleic acid probe attached to a solid support (such as a microarray), nucleic acid in a test sample may be amplified (e.g., using PCR) before or after the nucleic acid to be measured is hybridized with the probe. Various embodiments comprise reverse transcription polymerase chain reaction (RT-PCR) to detect mRNA levels (e.g., to determine the level of collagen18α1/endostatin, IGFBP-1, HTRA1 or NOTCH3). In some embodiments involving a probe on a solid support, the mRNA (or a portion thereof) in a test sample is converted to cDNA or partial cDNA and then the cDNA or partial cDNA is hybridized to a probe (e.g., on a microarray), hybridized to a probe and then amplified, or amplified and then hybridized to a probe. In some examples, a strip may be a nucleic acid-probe coated porous or non-porous solid support strip comprising linking a nucleic acid probe to a carrier to prepare a conjugate and immobilizing the conjugate on a porous solid support. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present subject matter. The support material may have any structural configuration so long as the coupled molecule is capable of binding to a binding agent (e.g., an antibody). Thus, the support configuration may be spherical, as in a bead, or cylindrical, as in the inside surface of a test tube, or the external surface of a rod. Alternatively, the surface may be flat such as a plate (or a well within a multiwell plate), sheet, or test strip, etc. Preferred supports include polystyrene beads. Those skilled in the art will know many other suitable carriers for binding antibody or antigen, or will be able to ascertain the same by use of routine experimentation.

In certain embodiments, the solid support comprises a polymer, to which an agent is chemically bound, immobilized, dispersed, or associated. A polymer support may be, e.g., a network of polymers, and may be prepared in bead form (e.g., by suspension polymerization). The location of active sites introduced into a polymer support depends on the type of polymer support. For example, in a swollen-gel-bead polymer support the active sites are distributed uniformly throughout the beads, whereas in a macroporous-bead polymer support they are predominantly on the internal surfaces of the macropores. The solid support, e.g., a device, may contain one or more or any combination of a collagen18α1/endostatin, IGFBP-1, HTRA1 or NOTCH3 binding agent.

In some embodiments, detection is accomplished using an enzyme-linked immunosorbent assay (ELISA) or Western blot format. In other examples, the binding agent comprises an collagen18α1/endostatin, IGFBP-1, HTRA1 or NOTCH3 specific nucleic acid (e.g., primers or a probe complementary for collagen18α1/endostatin, IGFBP-1, HTRA1 or NOTCH3 RNA or cDNA), and the detecting step is accomplished using a polymerase chain reaction (PCR) or Northern blot format, or other means of detection. In various embodiments, a probe or primer is about 10-20, 15-25, 15-35, 15-25, 20-80, 50-100, or 10-100 nucleotides in length, e.g., about 10, 12, 15, 20, 25, 30, 35, 40, 45, 50, 55, 60, 70, 80, 90, or 100 nucleotides in length or less than about 30, 35, 40, 45, 50, 55, 60, 70, 80, 90, or 100 nucleotides in length.

Biomarker changes that may be detected also include the redistribution of biomarkers between different compartments of a body, such as between a vessel and blood or between cerebrospinal fluid (CSF) and blood. Therefore, assaying of one or more of the biomarkers provided herein may be performed using a specific binding agent that may be detected with via imaging. Non-limiting examples of imaging technologies include PET and SPECT.

Aspects of the present subject matter provide a kit comprising (a) at least two agents selected from the group consisting of (i) an agent for detecting the level of collagen18α1 or endostatin; (ii) an agent for detecting the level of NOTCH3; (iii) an agent for detecting the level of IGFBP-1; and (iv) an agent for detecting the level of HTRA1, and (b) instructions for using the agent for diagnosing a SVD, for identifying whether a subject is at risk of developing the SVD, for determining the prognosis of the SVD, for determining the progression of SVD, for assessing the efficacy of a treatment for the SVD, and/or for adjusting the dose of a compound during the treatment of SVD. Embodiments of the present subject matter relate to kits that detect two or more of the biomarkers disclosed herein (e.g., at the same time) and/or protein-protein interactions between them. In some embodiments, the kid detects two or more of these proteins at the same time, or detects one or more protein-protein interactions between them. In various embodiments, a kit comprises reagents such as binding agents for use in assays to detect protein-protein interactions (e.g., with immunoprecipitation) between a biomarker herein and one or more proteins.

The present subject matter also provides a diagnostic system comprising (a) an assortment, collection, or compilation of test results data representing the level of collagen18α1/endostatin, IGFBP-1, HTRA1, and/or NOTCH3 in a plurality of test samples; (b) a means for computing an index value using said level, wherein the index value comprises a diagnostic, prognostic, progression, or treatment score; and (c) a means for reporting the index value.

Aspects of the present subject matter are directed to diagnostic biomarkers (e.g., collagen18α1/endostatin, IGFBP-1, HTRA1, and NOTCH3) for small vessel diseases that are associated with progressive vascular degeneration [e.g., CADASIL, AMD, CADASIL, DR, etc.].

In some embodiments, the level of collagen18α1/endostatin, IGFBP-1, N3ECD, and/or HTRA1 is measured in one or more biological fluids as part of a diagnostic or prognostic test for SVD. Measurements of collagen18α1/endostatin, IGFBP-1, N3ECD, and/or HTRA1 in biological fluids can be used as diagnostic or prognostic readouts for SVD. In certain embodiments, a method disclosed herein is part of a battery of testing for SVD. For example, a subject may be screened/tested and/or directed to receive additional screening/testing for a SVD based on the level of collagen18α1/endostatin, IGFBP-1, N3ECD, and/or HTRA1 in one or more bodily fluids.

In various embodiments, the level of collagen18α1/endostatin, IGFBP-1, N3ECD, and/or HTRA1 is measured in one or more biological fluids as part of a method for evaluating the effectiveness of a treatment or the progression of a disease. Measures of collagen18α1/endostatin, IGFBP-1, N3ECD, and/or HTRA1 in biological fluids can be used as biomarkers to determine the efficacy of a treatment in an animal model or human. For example, a subject may be administered and/or directed to receive a different treatment, an increased dose of a therapeutic compound, or a decreased dose of a therapeutic compound based on the level of collagen18α1/endostatin, IGFBP-1, N3ECD, and/or HTRA1 in one or more bodily fluids. In some embodiments, the therapeutic compound is a test compound being evaluated in a clinical trial. In certain embodiments, the therapeutic compound is a compound that has been approved for use in humans by a regulatory body such as the United States Food and Drug Administration.

In instances where an SVD cannot be specifically treated, the diagnostic and prognostic methods of the present subject matter provide valuable information to subjects that will allow them to make relevant lifestyle decisions and plan for the onset of likely symptoms. Thus, the present subject matter provides valuable tools, resources, and information to subjects with incurable SVDs.

In some embodiments, composite measurements and/or calculations based on multiple biomarkers are used. For example, composite measurements including the ratio of HTRA1 levels over that of N3ECD and/or collagen18α1/endostatin can be used as a diagnostic, prognostic, and/or efficacy biomarker.

Methods described herein represent a non-invasive (or minimally invasive) test assay. For example, the test sample such as blood is obtained by venipuncture, and the sample comprises a bodily fluid such as blood, serum, or plasma. In another example, the test sample comprises saliva, tears, vitreous, cerebrospinal fluid, sweat, cerebrospinal fluid, or urine.

In various implementations, the methods described herein may also include computing a level of collagen18α1/endostatin, IGFBP-1, N3ECD, HTRA1, or any combination thereof in a process that includes the use of a binding agent. An exemplary example of a binding agent includes an antibody (or a fragment thereof) or a detectable protein (or a fragment thereof). The antibody may be labeled with a detectable moiety, e.g., a fluorescent compound or a radioactive agent (e.g., technetium-99m, iodine-123, iodine-125, iodine-131, indium-111, carbon-11, nitrogen-13, oxygen-15, fluorine-18, gallium-68, zirconium-89, or rubidium-82). When the fluorescently labeled antibody is exposed to light of the proper wave length, its presence can then be detected due to fluorescence. Non-limiting examples of fluorescent labeling compounds include fluorescein isothiocyanate, rhodamine, phycoerythrin, phycocyanin, allophycocyanin, p-phthaldehyde, and fluorescamine. The antibody can also be detectably labeled using fluorescence emitting metals such as europium-152, or others of the lanthanide series. These metals can be attached to the antibody using such metal chelating groups as diethylenetriaminepentacetic acid (DTPA) or ethylenediaminetetraacetic acid (EDTA). The antibody also can be detectably labeled by coupling it to a chemiluminescent compound. The presence of the chemiluminescent-tagged antibody is then determined by detecting the presence of luminescence that arises during the course of chemical reaction. Non-limiting examples of particularly useful chemiluminescent labeling compounds include luminol, isoluminol, theromatic acridinium ester, imidazole, acridinium salt, and oxalate ester.

In various embodiments, the subject has cerebral SVD. In some embodiments, the subject comprises granular osmiophilic material (GOM) deposits. In certain embodiments, the subject does not comprise GOM deposits.

As used herein, a "specific binding agent" describes an agent having a greater than 10-fold, preferably greater than 100-fold, and most preferably, greater than 1000-fold affinity for a target molecule as compared to another molecule. As the skilled artisan will appreciate, the term "specific" is used to indicate that other biomolecules present in the sample do not significantly bind to the binding agent specific for the target molecule. In various embodiments, the level of binding to a biomolecule other than the target molecule results in a binding affinity which is at most only 10% or less, only 5% or less only 2% or less or only 1% or less of the affinity to the target molecule, respectively. A preferred specific binding agent will fulfill both the above minimum criteria for affinity as well as for specificity. For example, an antibody has a binding affinity in the low micromolar ($10^{-6}$), nanomolar ($10^{-7}$-$10^{-5}$), with high affinity antibodies in the low nanomolar ($10^{-9}$) or pico molar ($10^{-12}$) range for its specific target ligand.

The present subject matter describes a composition utilizing a binding agent, wherein the binding agent is attached to a solid support, (e.g., a strip, a polymer, a bead, or a nanoparticle). Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present subject matter. The support material may have virtually any possible structural configuration so long as the target molecule (e.g., an collagen18α1/endostatin, IGFBP-1, N3ECD, and/or HTRA1 protein) is capable of binding to a binding agent (e.g., an antibody). Thus, the support configuration may be spherical, as in a bead, or cylindrical, as in the inside surface of a test tube, or the external surface of a rod. Alternatively, the surface may be flat such as a sheet, or test strip, etc. In some embodiments, the support includes polystyrene beads. Those skilled in the art will know many other suitable carriers and supports, or will be able to ascertain the same by use of routine experimentation.

In some aspects, the solid support comprises a polymer, to which an agent is chemically bound, immobilized, dispersed, or associated. A polymer support may be a network of polymers, and may be prepared in bead form (e.g., by suspension polymerization). The location of active sites introduced into a polymer support depends on the type of polymer support. For example, in a swollen-gel-bead polymer support the active sites are distributed uniformly throughout the beads, whereas in a macroporous-bead polymer support they are predominantly on the internal surfaces of the macropores. In various embodiments, the solid support contains an collagen18α1/endostatin binding agent alone or together with a binding agent for at least one, two, three or more other molecules, e.g., IGFBP-1, NOTCH3 (e.g., N3ECD) and/or HTRA1. In some embodiments, the solid support contains a N3ECD binding agent alone or together with a binding agent for at least one, two, three or more other molecules, e.g., collagen18α1/endostatin, IGFBP-1, and/or HTRA1. In certain embodiments, the solid support contains a HTRA1 binding agent alone or together with a binding agent for at least one, two, three or more other molecules, e.g., collagen18α1/endostatin, IGFBP-1, and/or N3ECD. In certain embodiments, the solid support contains a IGFBP-1 binding agent alone or together with a binding agent for at least one, two, three or more other molecules, e.g., collagen18α1/endostatin, IGFBP-1, HTRA1, and/or N3ECD.

In various embodiments, a test (e.g., assay) is carried out on a bodily fluid such as blood, serum, plasma, saliva, tears, vitreous, cerebrospinal fluid, sweat, cerebrospinal fluid, or urine. The level of a protein may be measured using any applicable method known in the art, such as an immunoassay such as an enzyme-linked immunosorbent assay (ELISA), Western blot, radioimmunoassay (RIA), fluoroimmunoassay, or mass spectrometry. Non-limiting examples of mass spectrometry techniques include electrospray ionization (ESI), matrix assisted laser desorption (MALDI), MALDI-TOF (Time of flight), Fourier transform ion cyclotron resonance (FTIC), and surface-enhanced laser desorption (SELDI). Non-limiting examples of live imaging techniques for detecting the level and/or location (e.g., expression or localization changes) of a biomarker in the body of a subject include ultrasound, CT scans, an X-ray, MRI, PET, and SPECT.

As used herein, the term "assay" is intended to exclude the mere reading of a report or database entry. An assay is an investigative (analytic) procedure for qualitatively assessing or quantitatively measuring presence or amount or the functional activity of a target entity (e.g., the amount or level of collagen18α1/endostatin, IGFBP-1, N3ECD, and/or HTRA1 protein in a test sample).

The term "sample" as used herein refers to a biological sample obtained for the purpose of evaluation in vitro. In embodiments, the sample may comprise a body fluid. In some embodiments, the body fluid includes, but is not limited to, whole blood, plasma, serum, lymph, breast milk, saliva, mucous, semen, cellular extracts, inflammatory fluids, cerebrospinal fluid, vitreous humor, tears, vitreous, aqueous humor, or urine obtained from the subject. In some aspects, the sample is a composite panel of two or more body fluids. In exemplary aspects, the sample comprises blood or a fraction thereof (e.g., plasma, serum, of a fraction obtained via leukapheresis). In embodiments, the sample is a tissue sample, such as a biopsy.

Various methods disclosed herein comprise repeating providing, contacting, detecting, assaying, identifying, and/or computing steps over time. A progressive increase over time in the level of collagen18α1/endostatin, IGFBP-1, and/or HTRA1 indicates a progressive worsening of the severity of a SVD. A progressive decrease over time in the level of N3ECD indicates an amelioration of a SVD. In some embodiments, a method may include the step of treatment following risk stratification as described herein. For example, a method further comprises identifying a subject with a high risk of a particular symptom or disease and administering to that subject a therapeutic regimen to inhibit, treat, or prevent the symptom or disease.

Also disclosed herein is a kit comprising an collagen18α1/endostatin-, IGFBP N3ECD-, and/or HTRA1-binding agent(s) and instructions for using the agent(s) for diagnosing a subject, evaluating a subject's prognosis, or determining the efficacy of a therapeutic regimen. In some embodiments, the agent is attached to a solid support such a test strip. The kit optionally contains buffers, enzymes, salts, stabilizing agents, preservatives, and a container for receiving a test sample of bodily fluid or cell. In some cases, such a container contains an anti-coagulant or a cell separation agent (e.g., to separate white cells from red blood cells). In various embodiments, the agent is attached to a solid support (e.g., a test strip). A complex intermediate of collagen18α1/endostatin, IGFBP-1, N3ECD, and/or HTRA1 protein and binding agent may be formed to detect such collagen18α1/endostatin, IGFBP-1, N3ECD, and/or HTRA1 protein. Various embodiments relate to a kit comprising agents for measuring a group of markers, wherein the group of markers are defined as described in any of the paragraphs, or panels containing figures, or other descriptions of preferred sets or panels of markers found herein. In some variations, such agents are packaged together. In some variations, the kit further includes an analysis tool for evaluating risk of an individual developing an SVD or a symptom thereof from measurements of the group of markers from at least one biological sample from the subject.

The diagnostic or prognostic assay is optionally formulated in a two-antibody binding format in which one collagen18α1/endostatin-, IGFBP-1-, N3ECD-, or HTRA1-protein-specific antibody captures a collagen18α1/endostatin-, IGFBP-1-, N3ECD-, or HTRA1-protein, e.g., in a patient sample and another anti-collagen18α1/endostatin, anti-IGFBP-1, anti-N3ECD, or anti-HTRA1 antibody is used to detect captured protein. For example, the capture antibody is immobilized on a solid phase, e.g., an assay plate, an assay well, a nitrocellulose membrane, a bead, a dipstick, or a component of an elution column. The second antibody, i.e., the detection antibody, is typically tagged with a detectable label such as a colorimetric agent or radioisotope.

The present subject matter also describes diagnostic test system that obtains test results data representing levels of a marker in at least one biological sample. In various embodiments, the results are collected and tracked by the system. In some embodiments, the system comprises a means for computing an index value from said marker, wherein the index value comprises a SVD risk score or a SVD symptom risk score. The system may also include a means of reporting the index value.

Aspects of the present subject matter relate to a diagnostic test system comprising a means for obtaining test results data representing levels of a marker (e.g., the level of collagen18α1/endostatin, IGFBP-1, N3ECD, and/or HTRA1 protein) in at least one biological sample; a means for collecting and tracking test results data for one or more individual biological samples; a means for computing an index value from marker measurement data, wherein said biomarker measurement data is representative of measured levels of markers, wherein said measured levels of markers comprise the levels of a set or panel of markers; and a means for reporting said index value. In some variations of the diagnostic test system, the index value is a SVD risk score or a symptom risk score. In certain variations, the risk score is computed according to the methods described herein for computing such scores. In some variations, the means for collecting and tracking test results data representing information and/or index values for one or more individuals comprises a data structure or database. In various embodiments, the means for computing a risk score comprises a computer or microprocessor, comprising a visible display, an audio output, a link to a data structure or database, or a printer.

Methods, compositions, kits, and systems disclosed herein may be used to indicate that the method according to the present invention will, alone or together with other variables, establish or confirm the absence or presence of a SVD, or aid a physician in the prognosis, and or the monitoring of treatment. The skilled artisan will appreciate that any such evaluation or assessment is made using an in vitro assay. The patient sample is solely used for the in vitro diagnostic method and the material of the patient sample is not transferred back into the patient's body. Typically, the sample is a liquid sample, e.g., whole blood, serum, plasma, saliva, tears, vitreous, cerebrospinal fluid, sweat, cerebrospinal fluid, or urine.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DESCRIPTION OF THE DRAWINGS

FIG. 3A: ELISA detection of endostatin in plasma from mice (200 d) expressing the human NOTCH3 CADASIL mutation (N3KO; C455R+/−; SM22-Cre), or control (N3KO; WT76+/−; SM22-Cre) showing that there is significantly more endostatin protein circulating in the blood of CADASIL mice. Number of biological replicates is indicated in parenthesis.

FIG. 5A: Linear range of the N3ECD ELISA was found to range up to 2 μg/ml. FIG. 5B: N3ECD in human plasma and serum samples from patients with no known CADASIL mutations was significantly more abundant in human serum than plasma. Number of biological replicates is indicated in parenthesis. FIG. 5C: ELISA detection of human N3ECD in the plasma of mice (200 d) expressing the human NOTCH3 CADASIL mutation (N3KO; C455R+/−; SM22-Cre), or control (N3KO; WT76+/−; SM22-Cre) showing significantly less N3ECD protein circulating in the blood of CADASIL mice. Number of biological replicates is indicated in parenthesis. FIG. 5D: Primary cultures of MEFs from Cre-inducible CADASIL (N3KO; C455R+/+) or control mice (N3KO; WT76+/+), upon Adeno-Cre induction, expressed their respective transgenes at a similar level, irrespective of monoculture or coculture conditions. Asterisks (*) indicate P-value<0.05 (unpaired t-test).

FIG. 6A: Representative images of retinas from control mice (N3KO; WT76+/−; SM22-Cre) stained with the VSMC marker SMA (red). FIG. 6B: Same image from FIG. 6A, merged with IB4 staining (green). Overlay image shows SMA staining in 81% of the vascularized area. FIG. 6C: Representative images of retinas from CADASIL mice (N3KO; C455R+/−; SM22-Cre) stained with the VSMC marker SMA (red). FIG. 6D: Same image from FIG. 6C, merged with IB4 staining (green). Overlay image shows SMA staining in 55% of the total vascularized area. FIG. 6E: Quantification of VSMC coverage in the CADASIL mouse model. Merged images (see FIG. 8) of IB4 and SMA-stained retinas from control (N3KO; WT76+/−; SM22-Cre) or CADASIL (N3KO; C455R+/−; SM22-Cre) mice were quantified via Image J. To determine VSMC coverage, positive SMA staining was normalized to IB4. The number of biological replicates is indicated in parenthesis. Asterisks (*) indicate P-value<0.05 (unpaired t-test). The scale bar is 50 μm.

FIGS. 7A and B are tables showing results from candidate screening for CADASIL biomarkers. FIG. 7A: Relative expression of angiogenesis-related proteins in the plasma of mice expressing the human NOTCH3 CADASIL mutation (N3KO; C455R+/−; SM22-Cre), or NOTCH3 knockouts (N3KO), compared to control (N3KO; WT76+/−; SM22-Cre). Fold changes considered significant by variance analysis are highlighted in grey. "N/D" indicates proteins that were not detected. Fold changes are averages of two biological replicates. FIG. 7B: Mass spectrometry data of the aorta proteome from mice expressing the human NOTCH3 CADASIL mutation (N3KO; R1031C+/−; SM22-Cre) compared to control (N3KO; WT76+/−; SM22-Cre). HTRA1, highlighted in grey, was the highest Z scoring protein.

FIGS. 8A-D are images showing VSMC loss in the retinal vasculature using retinal flat mounts. FIG. 8A: Representative images of retinas from control mice (N3KO; WT76+/−; SM22-Cre), expressing the human WT NOTCH3, stained with the VSMC marker SMA (red). Image is centered on the optic nerve and the scale bar is 250 µm. FIG. 8B: Same image from FIG. 8A, merged with Isolectin B4 staining (green). Scale bar is 250 µm. FIG. 8C: Representative images of retinas from CADASIL mice (N3KO; C455R+/−; SM22-Cre), expressing the NOTCH3 CADASIL mutation, stained with the VSMC marker SMA (red). Image is centered on the optic nerve and the scale bar is 250 µm. FIG. 8D: Same image from panel A, merged with isolectin B4 staining (green). Scale bar is 250 µm.

DETAILED DESCRIPTION

Figure 1:
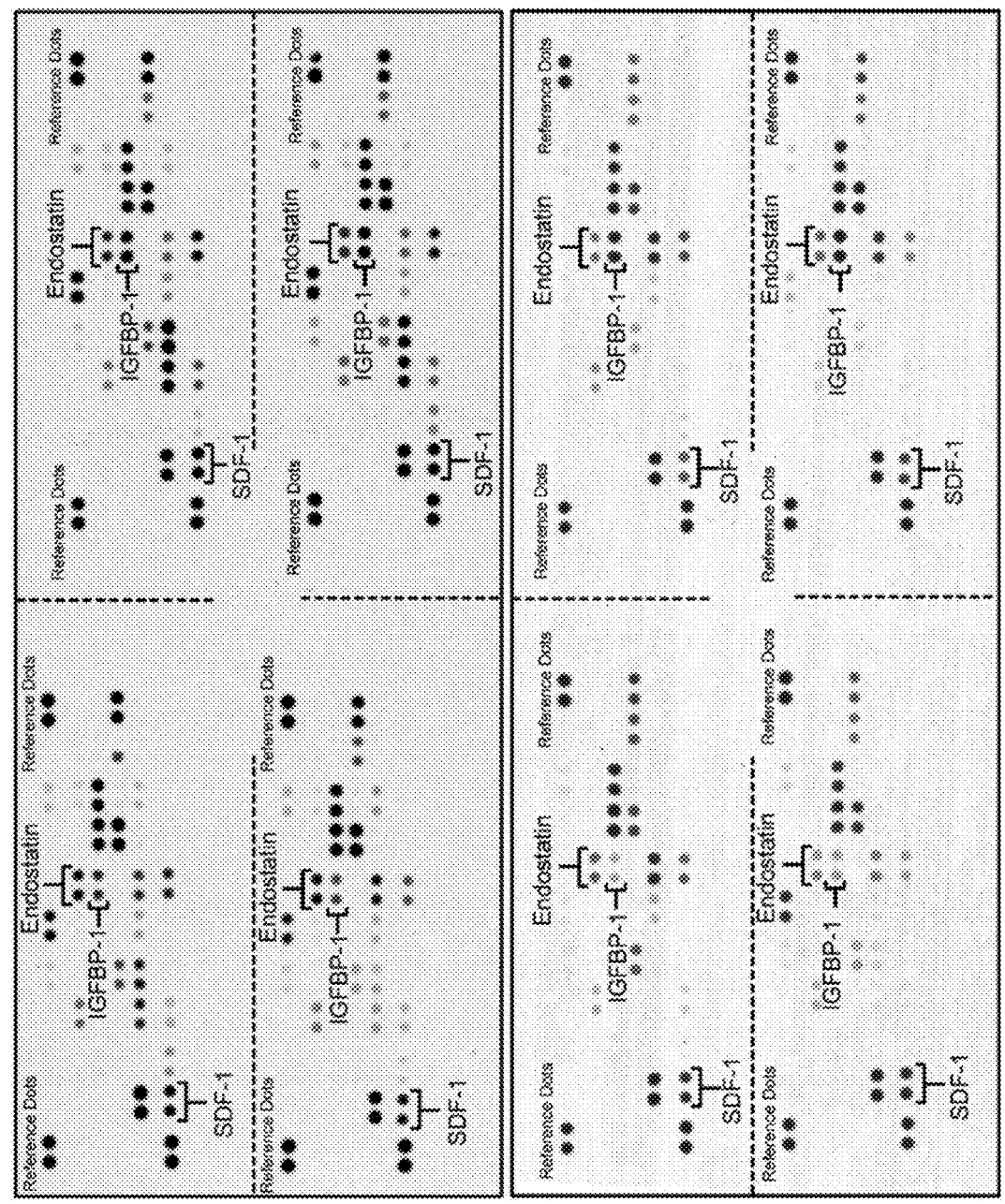
FIG. 1 is set of images of dot blots relating to a proteomic screen in CADASIL mice. Dot blots represent levels of specific proteins, in technical duplicate, found in plasma from two male CADASIL mice collected at 100 or 200 days of age (N3KO; C455R+/−; SM22-Cre) and two control (N3KO; WT76+/−; SM22-Cre). IGFBP-1, SDF-1, and collagen18α1/endostatin were found to be differentially expressed, as established by a variance analysis.

The present disclosure provides biomarkers that are useful in treatment, diagnostic, and prognostic methods relating to SVD. Methods include body fluid tests (such as blood tests) for the levels of biomarkers associated with SVD. Prior to the present invention, there were no protein biomarkers were available for the diagnosis or prognosis of SVD changes associated with vascular degeneration. Brain SVD is detected using expensive imaging techniques such as magnetic resonance imaging (MRI) or laborious neurological and neuropsychological tests. Retina SVD is detected by retinal imaging of the consequences of vascular damage. There are also no methods for analysis of small vessel degeneration at preclinical stages.

By using a model of a monogenic SVD affecting the brain and the retina, a group of proteins was identified to be biomarkers of SVD associated with progressive vascular degeneration. Measuring these biomarkers in biological fluids including blood, plasma, serum, tears, sweat, saliva, vitreous, cerebrospinal fluid, cerebrospinal fluid, or urine is useful for diagnostic and/or prognosis of SVD. Aspects of the present subject matter relate to the following unexpected discoveries:
  (i) NOTCH3 is a transmembrane cell surface receptor. It was unexpected that the extracellular domain of the receptor circulates in blood and/or body fluids and that its levels change in SVD.
  (ii) HTRA1 levels change in CADASIL, a condition that leads to stroke and vascular dementia.
  (iii) HTRA1 levels, independent of HTRA1 gene mutation status, change in subjects with SVD.
  (iv) The levels of a fragment of collagen18α1 known as "endostatin" change in the presence of SVD
  (v) The levels of IGFBP-1 change in subject with SVD.

In various embodiments, NOTCH3 binding to itself or another protein (such as collagen18α1/endostatin, IGFBP-1, and/or HTRA1) is indicative of SVD or a risk of developing a SVD. See, e.g., Arboleda-Velasquez et al. (2005) "CADASIL mutations impair Notch3 glycosylation by Fringe" Hum Mol Genet. 14(12):1631-9, the entire contents of which are incorporated herein by reference. In some embodiments, a NOTCH3 homodimer is indicative of SVD or a risk thereof. In certain embodiments, a NOTCH heterodimer is indicative of SVD or a risk thereof. In various embodiments, the protein-protein interaction is an aberrant protein-protein interaction. In certain embodiments, the method further comprises diagnosing a subject as having an SVD (such as CADASIL) if NOTCH3 is binding to collagen18α1/endostatin, IGFBP-1, and/or HTRA1 is detected in the subject (e.g., in a test sample from the subject).

In various embodiments, a mutation in the NOTCH3 gene triggers adult-onset stroke and vascular dementia in, e.g., a subject with a SVD such as CADASIL. In some embodiments, the mutation affects an epidermal growth factor-like (EGF-like) repeat located in the extracellular domain of the NOTCH3 receptor. EGF-like repeats in the NOCTH3 receptor is also the target of sequential complex O-linked glycosylation mediated by protein O-fucosyltransferase 1 and Fringe. In certain embodiments, the mutation does not affect the addition of O-fucose but does impair carbohydrate chain elongation by Fringe. In various embodiments, a subject has aberrant homodimerization of mutant NOTCH3 fragments and/or heterodimerization of mutant NOTCH3 with Lunatic Fringe itself. In certain embodiments, a subject has a complex (such as a dimer) comprising N3ECD and at least one other protein. In various embodiments, the interaction between the components of a homodimer or heterodimer comprising NOTCH3 or a portion thereof (e.g., a mutant NOTCH3 or N3ECD) is enhanced by one or more abnormal disulfide bonds. In some embodiments, a NOTCH3 homodimer comprises one or more disulfide bonds covalently connecting each NOTCH3 monomer.

In various embodiments, a subject comprises a N3ECD homodimer. In some embodiments, the N3ECD homodimer comprises one or more disulfide bonds covalently connecting each NOTCH3 monomer.

Endostatin

Endostatin is a naturally-occurring, 20-kDa C-terminal fragment derived collagen18α1 (which is encoded by the COL18A1 gene). Endostatin is cleaved off collagen18α1. It is reported to serve as an anti-angiogenic agent, similar to angiostatin and thrombospondin. Endostatin is a broad-spectrum angiogenesis inhibitor and may interfere with the pro-angiogenic action of growth factors such as basic fibroblast growth factor (bFGF/FGF-2) and vascular endothelial growth factor (VEGF).

A binding agent (e.g., an antibody) that specifically binds endostatin may also bind full-length collagen18α1. In various embodiments, it is not necessary to distinguish endostatin that is detected from collagen18α1 (i.e., it is not necessary to rule out or determine that a portion of the endostatin detected is full-length collagen18α1).

An amino acid sequence for human endostatin is publically available in the UniProt database as positions 1572-1754 of accession number P39060 (SEQ ID NO: 1) and is as follows:

HSHRDFQPVLHLVALNSPLSGGMRGIRGADFQCFQQARAVGLAGTFRAFL

SSRLQDLYSIVRRADRAAVPIVNLKDELLFPSWEALFSGSEGPLKPGARI

FSFDGKDVLRHPTWPQKSVWHGSDPNGRRLTESYCETWRTEAPSATGQAS

SLLGGRLLGQSAASCHHAYIVLCIENSFMTASK

A nucleotide sequence that encodes human endostatin is publically available in the GenBank database as positions 4021-4569 of accession number NM 030582.3 (SEQ ID NO: 2) and is as follows:

```
CACAGCCACC GCGACTTCCA GCCGGTGCTC CACCTGGTTG

CGCTCAACAG CCCCCTGTCAGGCGGCATGC GGGGCATCCG

CGGGGCCGAC TTCCAGTGCT TCCAGCAGGC GCGGGCCGTG

GGGCTGGCGG GCACCTTCCG CGCCTTCCTG TCCTCGCGCC

TGCAGGACCT GTACAGCATCGTGCGCCGTG CCGACCGCGC

AGCCGTGCCC ATCGTCAACC TCAAGGACGA GCTGCTGTTT

CCCAGCTGGG AGGCTCTGTT CTCAGGCTCT GAGGGTCCGC

TGAAGCCCGG GGCACGCAT CTTCTCCTTTG ACGGCAAGGA

CGTCCTGAGG CACCCCACCT GGCCCCAGAA GAGCGTGTGG

CATGGCTCGG ACCCCAACGG GCGCAGGCTG ACCGAGAGCT

ACTGTGAGAC GTGGCGGACGGAGGCTCCCT CGGCCACGGG

CCAGGCCTCC TCGCTGCTGG GGGGCAGGCT CCTGGGGCAG

AGTGCCGCGA GCTGCCATCA CGCCTACATC GTGCTCTGCA

TTGAGAACGA CTTCATGACTGCCTCCAAG
```

NOTCH3

The NOTCH3 gene encodes the third discovered human homologue of the *Drosophila melanogaster* type I membrane protein notch. In *Drosophila*, notch's interaction with its cell-bound ligands (delta, serrate) establishes an intercellular signaling pathway that plays a key role in neural development. Homologues of the notch-ligands have also been identified in humans, but precise interactions between these ligands and the human notch homologues remains to be determined. NOTCH3 functions as a receptor for membrane-bound ligands JAGGED1, JAGGED2 and DELTA-LIKE1, DELTA-LIKE3, and DELTA-LIKE4 to regulate cell-fate determination. NOTCH3 has been proposed to affect the implementation of differentiation, proliferation and apoptotic programs.

Mutations in NOTCH3 have been identified as the underlying cause of cerebral autosomal dominant arteriopathy with subcortical infarcts and leukoencephalopathy (CADASIL). NOTCH3 mutations (including mutations that result in amino acid changes other than cysteine substitutions in the extracellular domain) are also associated with SVDs other than CADASIL. NOTCH3 loss of function-associated SVD is distinct from CADASIL because it lacks the characteristic accumulation of NOTCH3 extracellular domain in vessels and it lacks granular osmiophilic deposits (GOMs). In embodiments, a subject with such a SVD has symptoms that are similar to CADASIL. See, e.g., Moccia et al., (2015) Hypomorphic NOTCH3 mutation in an Italian family with CADASIL features. Neurobiol Aging 36(1):547.e5-11; and Fouillade et al., (2008) Activating NOTCH3 mutation in a patient with small-vessel-disease of the brain. Hum Mutat. 29(3):452, the entire contents of each of which are incorporated herein by reference. In various embodiments, the subject has migraines. In some embodiments, the subject has migraines with aura. In certain embodiments, the skin of the subject comprises vascular damage. A non-limiting example of a mutation that may result in a SVD symptoms similar to CADASIL is a C to U substitution at position 307 of the open reading frame of NOTCH3-encoding mRNA (a cDNA sequence is provided as SEQ ID NO: 4), which results in a truncation of the protein such that amino acids from position R103 to the wild-type C-terminus are missing. Another non-limiting example includes a L1515P substitution.

In some embodiments, the subject comprises a R103X substitution mutation. In certain embodiments, the mutation results in a substitution or a truncation within an Epidermal Growth-Factor-like Repeat of NOTCH3. In various embodiments, the mutation is within one of exons 2-24 of the NOTCH3 gene. In some embodiments, the mutation is a missense mutation in exon 25 of NOTCH3. In certain embodiments, the mutation comprises a substitution or mutation within the heterodimerization domain of NOTCH3. In various embodiments, the mutation results in a L1515P substitution. In some embodiments, the substitution is not a conservative substitution. In certain embodiments, the subject comprises an autosomal mutation in NOTCH3. In some embodiments, the mutation results in reduced NOTCH3 function. In various embodiments, the mutation results in increased NOTCH3 function. In some embodiments, the mutation comprises substitution in the extracellular domain of NOTCH3 that adds or removes a cysteine compared to wild-type NOTCH3. In certain embodiments, the mutation comprises a truncation beginning in the extracellular domain of the NOTCH3 protein. In embodiments, the subject is heterozygous for the mutation. In embodiments, the subject is homozygous for the mutation.

In certain embodiments, the subject expresses NOTCH3 with any of the following CADASIL mutations: C43G, C49F, C49Y, R54C, 560C, C65S, C67Y, W71C, C76R, C76W, 77-82del, 80-84del, C87R, C87Y, R90C, C93F, C93Y, C106W, C108W, C108Y, R110C, 114-120del, C117F, S118C, C123F, C123Y, C128Y, R133C, C134W, R141C, F142C, C1445, C144Y, 5145C, C146R, G149C, Y150C, 153-155del, R153C, C1555, C1625, R169C, G171C, C174F, C174R, C174Y, S180C, R182C, C183F, C183R, C1835, C185G, C185R, Y189C, C194F, C194R, C1945, C194Y, C201Y, C206Y, R207C, C2125, R213K, C222G, C222Y, C224Y, C233S, C233Y, 239-253del, C240S, C245R, C251R, Y258C, C260Y, C311G, A319C, R332C, 5335C, Y337C, C349S, C379S, C395R, G420C, R421C, C428S, C428Y, C440G, C440R, C446S, R449C, C455R, C484F, C484Y, C495Y, C511R, C542Y, R544C, C549Y, R558C, R578C, R587C, R607C, C608Y, C624S, C635C, R640C, R717C, Y710C, R728C, C775S, G942C, R951C, G953C, F984C, R985C, R1006C, C1015R, Y1021C, R1031C, R1143C, D1063C, R1190C, R1201C, C1202S, R1210C, C1222G, R1231C, R1242C, C1261R, and C1261Y. In certain embodiments, the subject expresses NOTCH3 with a mutation that results in an extracellular domain of NOTCH3 having an odd number of cysteines according to the formula CnX or XnC where C stands for cysteine, n for an amino acid number in the NOTCH3 extracellular domain and X any amino replacing cysteine (for CnX) or replaced by cysteine (for XnC). In certain embodiments, n is the amino acid number (i.e., position) of any amino acid in the extracellular domain of NOTCH3. In certain embodiments, n is any one of positions 40-1643 of SEQ ID NO: 10. In certain embodiments, n is any one of positions 40-100, 100-250, 250-500, 500-750, 750-1000, 1000-1250, 1250-1500, or 1500-1643 of SEQ ID NO: 3. In certain embodiments, the subject express NOTCH3 with cysteine-sparing mutations either of the following: R61W, R75P, D80G 88-91del. See, e.g., Wollenweber et al., (2015) Cysteine-sparing CADASIL mutations in NOTCH3 show proaggregatory properties in vitro. Stroke 46(3):786-92, the entire content of which is incorporated herein by reference. In certain embodiments, the subject carries loss of function mutations in NOTCH 3 including frame shift, premature stop codon, out of frame insertions or deletions, or splicing mutations including any of the following mutations: p.R113Ter, p.R103Ter, p.R156Ter, p.Y220Ter, c.1951+2delT, p.C729Ter, p.R735Ter, p.C966Ter, p.G2035RfsTer60, p.T1816ITer3, c.2566+1G>C, p.C1110Ter, p.E1125Ter, p.Y1453Ter, p.R1851VfsTer60, c.5667+1G>A, p.R1893Ter, c.5914-2_5914-linsT, p.G2035RfsTer60, p.G2035VfsTer50. See, e.g., Pippucci et al., (2015) Homozygous NOTCH3 null mutation and impaired NOTCH3 signaling in recessive early-onset arteriopathy and cavitating leukoencephalopathy. EMBO Mol Med. 7(6):848-58; Moccia et al., (2015) Hypomorphic NOTCH3 mutation in an Italian family with CADASIL features. Neurobiol Aging 36(1):547.e5-11, the entire contents of each of which are incorporated herein by reference.

An amino acid sequence for human NOTCH3 is publically available in the UniProt database under accession number Q9UM47 (SEQ ID NO: 3) is as follows (exemplary sites that may be substituted in subjects with SVD including CADASIL, cysteine-sparing mutations and NOTCH3 loss of function mutations are bolded and underlined):

MGPGARGRRRRRRPMSPPPPPPPVRALPLLLLLAGPGAAAPPCLDGSPCA

NGGRCTQLPSREAACLCPPGWVGERCQLEDPCHSGPCAGRGVCQSSVVAG

TARFSCRCPRGFRGPDCSLPDPCLSSPCAHGARCSVGPDGRFLCSCPPGY

QGRSCRSDVDECRVGEPCRHGGTCLNTPGSFRCQCPAGYTGPLCENPAVP

CAPSPCRNGGTCRQSGDLTYDCACLPGFEGQNCEVNVDDCPGHRCLNGGT

CVDGVNTYNCQCPPEWTGQFCTEDVDECQLQPNACHNGGTCFNTLGGHSC

VCVNGWTGESCSQNIDDCATAVCFHGATCHDRVASFYCACPMGKTGLLCH

LDDACVSNPCHEDAICDTNPVNGRAICTCPPGFTGGACDQDVDECSIGAN

PCEHLGRCVNTQGSFLCQCGRGYTGPRCETDVNECLSGPCRNQATCLDRI

GQFTCICMAGFTGTYCEVDIDECQSSPCVNGGVCKDRVNGFSCTCPSGFS

GSTCQLDVDECASTPCRNGAKCVDQPDGYECRCAEGFEGTLCDRNVDDCS

PDPCHHGRCVDGIASFSCACAPGYTGTRCESQVDECRSQPCRHGGKCLDL

VDKYLCRCPSGTTGVNCEVNIDDCASNPCTFGVCRDGINRYDCVCQPGFT

GPLCNVEINECASSPCGEGGSCVDGENGFRCLCPPGSLPPLCLPPSHPCA

HEPCSHGICYDAPGGFRCVCEPGWSGPRCSQSLARDACESQPCRAGGTCS

SDGMGFHCTCPPGVQGRQCELLSPCTPNPCEHGGRCESAPGQLPVCSCPQ

GWQGPRCQQDVDECAGPAPCGPHGICTNLAGSFSCTCHGGYTGPSCDQDI

NDCDPNPCLNGGSCQDGVGSFSCSCLPGFAGPRCARDVDECLSNPCGPGT

CTDHVASFTCTCPPGYGGFHCEQDLPDCSPSSCFNGGTCVDGVNSFSCLC

RPGYTGAHCQHEADPCLSRPCLHGGVCSAAHPGFRCTCLESFTGPQCQTL

VDWCSRQPCQNGGRCVQTGAYCLCPPGWSGRLCDIRSLPCREAAAQIGVR

LEQLCQAGGQCVDEDSSHYCVCPEGRTGSHCEQEVDPCLAQPCQHGGTCR

GYMGGYMCECLPGYNGDNCEDDVDECASQPCQHGGSCIDLVARYLCSCPP

GTLGVLCEINEDDCGPGPPLDSGPRCLHNGTCVDLVGGFRCTCPPGYTGL

RCEADINECRSGACHAAHTRDCLQDPGGGFRCLCHAGFSGPRCQTVLSPC

ESQPCQHGGQCRPSPGPGGGLTFTCHCAQPFWGPRCERVARSCRELQCPV

GVPCQQTPRGPRCACPPGLSGPSCRSFPGSPPGASNASCAAAPCLHGGSC

RPAPLAPFFRCACAQGWTGPRCEAPAAAPEVSEEPRCPRAACQAKRGDQR

CDRECNSPGCGWDGGDCSLSVGDPWRQCEALQCWRLFNNSRCDPACSSPA

CLYDNFDCHAGGRERTCNPVYEKYCADHFADGRCDQGCNTEECGWDGLDC

ASEVPALLARGVLVLTVLLPPEELLRSSADFLQRLSAILRTSLRFRLDAH

GQAMVFPYHRPSPGSEPRARRELAPEVIGSVVMLEIDNRLCLQSPENDHC

FPDAQSAADYLGALSAVERLDFPYPLRDVRGEPLEPPEPSVPLLPLLVAG

AVLLLVILVLGVMVARRKREHSTLWFPEGFSLHKDVASGHKGRREPVGQD

ALGMKNMAKGESLMGEVATDWMDTECPEAKRLKVEEPGMGAEEAVDCRQW

TQHHLVAADIRVAPAMALTPPQGDADADGMDVNVRGPDGFTPLMLASFCG

GALEPMPTEEDEADDTSASIISDLICQGAQLGARTDRTGETALHLAARYA

RADAAKRLLDAGADTNAQDHSGRTPLHTAVTADAQGVFQILIRNRSTDLD

ARMADGSTALILAARLAVEGMVEELIASHADVNAVDELGKSALHWAAAVN

NVEATLALLKNGANKDMQDSKEETPLFLAAREGSYEAAKLLLDHFANREI

TDHLDRLPRDVAQERLHQDIVRLLDQPSGPRSPPGPHGLGPLLCPPGAFL

PGLKAAQSGSKKSRRPPGKAGLGPQGPRGRGKKLTLACPGPLADSSVTLS

PVDSLDSPRPFGGPPASPGGFPLEGPYAAATATAVSLAQLGGPGRAGLGR

QPPGGCVLSLGLLNPVAVPLDWARLPPPAPPGPSFLLPLAPGPQLLNPGT

PVSPQERPPPYLAVPGHGEEYPAAGAHSSPPKARFLRVPSEHPYLTPSPE

SPEHWASPSPPSLSDWSESTPSPATATGAMATTTGALPAQPLPLSVPSSL

AQAQTQLGPQPEVTPKRQVLA

A nucleotide sequence that encodes human NOTCH3 is publically available in the GenBank database under accession number NM 000435.2 and is as follows (the start and stop codons are underlined and bolded):

(SEQ ID No. 13)
GCGGCGCGGAGGCTGGCCCGGGACGCGCCCGGAGCCCAGGGAAGGAGGGA

GGAGGGAGGGTCGCGGCCGGCCGCCATGGGGCCGGGGGCCCGTGGCCGC

CGCCGCCGCCGTCGCCCGATGTCGCCGCCACCGCCACCGCCACCCGTGCG

GGCGCTGCCCCTGCTGCTGCTGCTAGCGGGGCCGGGGGCTGCAGCCCCCC

CTTGCCTGGACGGAAGCCCGTGTGCAAATGGAGGTCGTTGCACCCAGCTG

CCCTCCCGGGAGGCTGCCTGCCTGTGCCCGCCTGGCTGGGTGGGTGAGCG

-continued

GTGTCAGCTGGAGGACCCCTGTCACTCAGGCCCCTGTGCTGGCCGTGGTG

TCTGCCAGAGTTCAGTGGTGGCTGGCACCGCCCGATTCTCATGCCGGTGC

CCCCGTGGCTTCCGAGGCCCTGACTGCTCCCTGCCAGATCCCTGCCTCAG

CAGCCCTTGTGCCCACGGTGCCCGCTGCTCAGTGGGGCCCGATGGACGCT

TCCTCTGCTCCTGCCCACCTGGCTACCAGGGCCGCAGCTGCCGAAGCGAC

GTGGATGAGTGCCGGGTGGGTGAGCCCTGCCGCCATGGTGGCACCTGCCT

CAACACACCTGGCTCCTTCCGCTGCCAGTGTCCAGCTGGCTACACAGGGC

CACTATGTGAGAACCCCGCGGTGCCCTGTGCACCCTCACCATGCCGTAAC

GGGGGCACCTGCAGGCAGAGTGGCGACCTCACTTACGACTGTGCCTGTCT

TCCTGGGTTTGAGGGTCAGAATTGTGAAGTGAACGTGGACGACTGTCCAG

GACACCGATGTCTCAATGGGGGACATGCGTGGATGGCGTCAACACCTAT

AACTGCCAGTGCCCTCCTGAGTGGACAGGCCAGTTCTGCACGGAGGACGT

GGATGAGTGTCAGCTGCAGCCCAACGCCTGCCACAATGGGGGTACCTGCT

TCAACACGCTGGGTGGCCACAGCTGCGTGTGTGTCAATGGCTGGACAGGC

GAGAGCTGCAGTCAGAATATCGATGACTGTGCCACAGCCGTGTGCTTCCA

TGGGGCCACCTGCCATGACCGCGTGGCTTCTTTCTACTGTGCCTGCCCCA

TGGGCAAGACTGGCCTCCTGTGTCACCTGGATGACGCCTGTGTCAGCAAC

CCCTGCCACGAGGATGCTATCTGTGACACAAATCCGGTGAACGGCCGGGC

CATTTGCACCTGTCCTCCCGGCTTCACGGGTGGGGCATGTGACCAGGATG

TGGACGAGTGCTCTATCGGCGCCAACCCCTGCGAGCACTTGGGCAGGTGC

GTGAACACGCAGGGCTCCTTCCTGTGCCAGTGCGGTCGTGGCTACACTGG

ACCTCGCTGTGAGACCGATGTCAACGAGTGTCTGTCGGGGCCCTGCCGAA

ACCAGGCCACGTGCCTCGACCGCATAGGCCAGTTCACCTGTATCTGTATG

GCAGGCTTCACAGGAACCTATTGCGAGGTGGACATTGACGAGTGTCAGAG

TAGCCCCTGTGTCAACGGTGGGGTCTGCAAGGACCGAGTCAATGGCTTCA

GCTGCACCTGCCCCTCGGGCTTCAGCGGCTCCACGTGTCAGCTGGACGTG

GACGAATGCGCCAGCACGCCCTGCAGGAATGCGCCAAATGCGTGGACCA

GCCCGATGGCTACGAGTGCCGCTGTGCCGAGGGCTTTGAGGGCACGCTGT

GTGATCGCAACGTGGACGACTGCTCCCCTGACCCATGCCACCATGGTCGC

TGCGTGGATGGCATCGCCAGCTTCTCATGTGCCTGTGCTCCTGGCTACAC

GGGCACACGCTGCGAGAGCCAGGTGGACGAATGCCGCAGCCAGCCCTGCC

GCCATGGCGGCAAATGCCTAGACCTGGTGGACAAGTACCTCTGCCGCTGC

CCTTCTGGGACCACAGGTGTGAACTGCGAAGTGAACATTGACGACTGTGC

CAGCAACCCCTGCACCTTTGGAGTCTGCCGTGATGGCATCAACCGCTACG

ACTGTGTCTGCCAACCTGGCTTCACAGGGCCCCTTTGTAACGTGGAGATC

AATGAGTGTGCTTCCAGCCCATGCGGCGAGGGAGGTTCCTGTGTGGATGG

GGAAAATGGCTTCCGCTGCCTCTGCCCGCCTGGCTCCTTGCCCCCACTCT

GCCTCCCCCCGAGCCATCCCTGTGCCCATGAGCCCTGCAGTCACGGCATC

TGCTATGATGCACCTGGCGGGTTCCGCTGTGTGTGTGAGCCTGGCTGGAG

TGGCCCCCGCTGCAGCCAGAGCCTGGCCCGAGACGCCTGTGAGTCCCAGC

CGTGCAGGGCCGGTGGGACATGCAGCAGCGATGGAATGGGTTTCCACTGC

-continued

ACCTGCCCGCCTGGTGTCCAGGGACGTCAGTGTGAACTCCTCTCCCCCTG

CACCCCGAACCCCTGTGAGCATGGGGGCCGCTGCGAGTCTGCCCCTGGCC

AGCTGCCTGTCTGCTCCTGCCCCCAGGGCTGGCAAGGCCCACGATGCCAG

CAGGATGTGGACGAGTGTGCTGGCCCCGCACCCTGTGGCCCTCATGGTAT

CTGCACCAACCTGGCAGGGAGTTTCAGCTGCACCTGCCATGGAGGGTACA

CTGGCCCTTCCTGCGATCAGGACATCAATGACTGTGACCCCAACCCATGC

CTGAACGGTGGCTCGTGCCAAGACGGCGTGGGCTCCTTTTCCTGCTCCTG

CCTCCCTGGTTTCGCCGGCCCACGATGCGCCCGCGATGTGGATGAGTGCC

TGAGCAACCCCTGCGGCCCGGGCACCTGTACCGACCACGTGGCCTCCTTC

ACCTGCACCTGCCCGCCAGGCTACGGAGGCTTCCACTGCGAACAGGACCT

GCCCGACTGCAGCCCCAGCTCCTGCTTCAATGGCGGGACCTGTGTGGACG

GCGTGAACTCGTTCAGCTGCCTGTGCCGTCCCGGCTACACAGGAGCCCAC

TGCCAACATGAGGCAGACCCCTGCCTCTCGCGGCCCTGCCTACACGGGGG

CGTCTGCAGCGCCGCCCACCCTGGCTTCCGCTGCACCTGCCTCGAGAGCT

TCACGGGCCCGCAGTGCCAGACGCTGGTGGATTGGTGCAGCCGCCAGCCT

TGTCAAAACGGGGGTCGCTGCGTCCAGACTGGGGCCTATTGCCTTTGTCC

CCCTGGATGGAGCGGACGCCTCTGTGACATCCGAAGCTTGCCCTGCAGGG

AGGCCGCAGCCCAGATCGGGGTGCGGCTGGAGCAGCTGTGTCAGGCGGGT

GGGCAGTGTGTGGATGAAGACAGCTCCCACTACTGCGTGTGCCCAGAGGG

CCGTACTGGTAGCCACTGTGAGCAGGAGGTGGACCCCTGCTTGGCCCAGC

CCTGCCAGCATGGGGGGACCTGCCGTGGCTATATGGGGGGCTACATGTGT

GAGTGTCTTCCTGGCTACAATGGTGATAACTGTGAGGACGACGTGGACGA

GTGTGCCTCCCAGCCCTGCCAGCACGGGGGTTCATGCATTGACCTCGTGG

CCCGCTATCTCTGCTCCTGTCCCCCAGGAACGCTGGGGGTGCTCTGCGAG

ATTAATGAGGATGACTGCGGCCCAGGCCCACCGCTGGACTCAGGGCCCCG

GTGCCTACACAATGGCACCTGCGTGGACCTGGTGGGTGGTTTCCGCTGCA

CCTGTCCCCCAGGATACACTGGTTTGCGCTGCGAGGCAGACATCAATGAG

TGTCGCTCAGGTGCCTGCCACGCGGCACACACCCGGGACTGCCTGCAGGA

CCCAGGCGGAGGTTTCCGTTGCCTTTGTCATGCTGGCTTCTCAGGTCCTC

GCTGTCAGACTGTCCTGTCTCCCTGCGAGTCCCAGCCATGCCAGCATGGA

GGCCAGTGCCGTCCTAGCCCGGGTCCTGGGGGTGGGCTGACCTTCACCTG

TCACTGTGCCCAGCCGTTCTGGGGTCCGCGTTGCGAGCGGGTGGCGCGCT

CCTGCCGGGAGCTGCAGTGCCGGTGGGCGTCCATGCCAGCAGACGCCCC

CGCGGGCCGCGCTGCGCCTGCCCCCCAGGGTTGTCGGGACCCTCCTGCCG

CAGCTTCCGGGGTCGCCGCCGGGGGCCAGCAACGCCAGCTGCGCGGCCG

CCCCCTGTCTCCACGGGGGCTCCTGCCGCCCCGCGCCGCTCGCGCCCTTC

TTCCGCTGCGCTTGCGCGCAGGGCTGGACCGGGCCGCGCTGCGAGGCGCC

CGCCGCGGCACCCGAGGTCTCGGAGGAGCCGCGGTGCCCGCGCGCCGCCT

GCCAGGCCAAGCGCGGGGACCAGCGCTGCGACCGCGAGTGCAACAGCCCA

GGCTGCGGCTGGGACGGCGGCGACTGCTCGCTGAGCGTGGGCGACCCCTG

-continued
GCGGCAATGCGAGGCGCTGCAGTGCTGGCGCCTCTTCAACAACAGCCGCT
GCGACCCCGCCTGCAGCTCGCCCGCCTGCCTCTACGACAACTTCGACTGC
CACGCCGGTGGCCGCGAGCGCACTTGCAACCCGGTGTACGAGAAGTACTG
CGCCGACCACTTTGCCGACGGCCGCTGCGACCAGGGCTGCAACACGGAGG
AGTGCGGCTGGGATGGGCTGGATTGTGCCAGCGAGGTGCCGGCCCTGCTG
GCCCGCGGCGTGCTGGTGCTCACAGTGCTGCTGCCGCCAGAGGAGCTACT
GCGTTCCAGCGCCGACTTTCTGCAGCGGCTCAGCGCCATCCTGCGCACCT
CGCTGCGCTTCCGCCTGGACGCGCACGGCCAGGCCATGGTCTTCCCCTTAC
CACCGGCCTAGTCCTGGCTCCGAACCCCGGGCCCGTCGGGAGCTGGCCCC
CGAGGTGATCGGCTCGGTAGTAATGCTGGAGATTGACAACCGGCTCTGCC
TGCAGTCGCCTGAGAATGATCACTGCTTCCCCGATGCCCAGAGCGCCGCT
GACTACCTGGGAGCGTTGTCAGCGGTGGAGCGCCTGGACTTCCCGTACCC
ACTGCGGGACGTGCGGGGGAGCCGCTGGAGCCTCCAGAACCCAGCGTCC
CGCTGCTGCCACTGCTAGTGGCGGGCGCTGTCTTGCTGCTGGTCATTCTC
GTCCTGGGTGTCATGGTGGCCCGGCGCAAGCGCGAGCACAGCACCCTCTG
GTTCCCTGAGGGCTTCTCACTGCACAAGGACGTGGCCTCTGGTCACAAGG
GCCGGCGGGAACCCGTGGGCCAGGACGCGCTGGGCATGAAGAACATGGCC
AAGGGTGAGAGCCTGATGGGGGAGGTGGCCACAGACTGGATGGACACAGA
GTGCCCAGAGGCCAAGCGGCTAAAGGTAGAGGAGCCAGGCATGGGGGCTG
AGGAGGCTGTGGATTGCCGTCAGTGGACTCAACACCATCTGGTTGCTGCT
GACATCCGCGTGGCACCAGCCATGGCACTGACACCACCACAGGGCGACGC
AGATGCTGATGGCATGGATGTCAATGTGCGTGGCCCAGATGGCTTCACCC
CGCTAATGCTGGCTTCCTTCTGTGGGGGGCTCTGGAGCAATGCCAACT
GAAGAGGATGAGGCAGATGACACATCAGCTAGCATCATCTCCGACCTGAT
CTGCCAGGGGGCTCAGCTTGGGGCACGGACTGACCGTACTGGCGAGACTG
CTTTGCACCTGGCTGCCCGTTATGCCCGTGCTGATGCAGCCAAGCGGCTG
CTGGATGCTGGGGCAGACACCAATGCCCAGGACCACTCAGGCCGCACTCC
CCTGCACACAGCTGTCACAGCCGATGCCCAGGGTGTCTTCCAGATTCTCA
TCCGAAACCGCTCTACAGACTTGGATGCCCGCATGGCAGATGGCTCAACG
GCACTGATCCTGGCGGCCCGCCTGGCAGTAGAGGGCATGGTGGAAGAGCT
CATCGCCAGCCATGCTGATGTCAATGCTGTGGATGAGCTTGGGAAATCAG
CCTTACACTGGGCTGCGGCTGTGAACAACGTGGAAGCCACTTTGGCCCTG
CTCAAAAATGGAGCCAATAAGGACATGCAGGATAGCAAGGAGGAGACCCC
CCTATTCCTGGCCGCCCGCGAGGGCAGCTATGAGGCTGCCAAGCTGCTGT
TGGACCACTTTGCCAACCGTGAGATCACCGACCACCTGGACAGGCTGCCG
CGGGACGTAGCCCAGGAGAGACTGCACCAGGACATCGTGCGCTTGCTGGA
TCAACCCAGTGGGCCCCGCAGCCCCCCGGTCCCCACGGCCTGGGGCCTC
TGCTCTGTCCTCCAGGGGCCTTCCTCCCTGGCCTCAAAGCGGCACAGTCG
GGGTCCAAGAAGAGCAGGAGGCCCCCGGGAAGGCGGGGCTGGGGCCGCA
GGGGCCCCGGGGCGGGGCAAGAAGCTGACGCTGGCCTGCCCGGGCCCCC
TGGCTGACAGCTCGGTCACGCTGTCGCCCGTGGACTCGCTGGACTCCCCG -continued
CGGCCTTTCGGTGGGCCCCCTGCTTCCCCTGGTGGCTTCCCCCTTGAGGG
GCCCTATGCAGCTGCCACTGCCACTGCAGTGTCTCTGGCACAGCTTGGTG
GCCCAGGCCGGGCGGGTCTAGGGCGCCAGCCCCCTGGAGGATGTGTACTC
AGCCTGGGCCTGCTGAACCCTGTGGCTGTGCCCCTCGATTGGGCCCGGCT
GCCCCCACCTGCCCCTCCAGGCCCCTCGTTCCTGCTGCCACTGGCGCCGG
GACCCCAGCTGCTCAACCCAGGGACCCCCGTCTCCCCGCAGGAGCGGCCC
CCGCCTACCTGGCAGTCCCAGGACATGGCGAGGAGTACCCGGCGGCTGG
GGCACACAGCAGCCCCCAAAGGCCCGCTTCCTGCGGGTTCCCAGTGAGC
ACCCTTACCTGACCCCATCCCCCGAATCCCTGAGCACTGGGCCAGCCCC
TCACCTCCCTCCCTCTCAGACTGGTCCGAATCCACGCCTAGCCCAGCCAC
TGCCACTGGGGCCATGGCCACCACCACTGGGGCACTGCCTGCCCAGCCAC
TTCCCTTGTCTGTTCCCAGCTCCCTTGCTCAGGCCCAGACCCAGCTGGGG
CCCCAGCCGGAAGTTACCCCCAAGAGGCAAGTGTTGGCCTGAGACGCTCG
TCAGTTCTTAGATCTTGGGGGCCTAAAGAGACCCCCGTCCTGCCTCCTTT
CTTTCTCTGTCTCTTCCTTCCTTTTAGTCTTTTTCATCCTCTTCTCTTTC
CACCAACCCTCCTGCATCCTTGCCTTGCAGCGTGACCGAGATAGGTCATC
AGCCCAGGGCTTCAGTCTTCCTTTATTTATAATGGGTGGGGGCTACCACC
CACCCTCTCAGTCTTGTGAAGAGTCTGGGACCTCCTTCTTCCCCACTTCT
CTCTTCCCTCATTCCTTTCTCTCTCCTTCTGGCCTCTCATTTCCTTACAC
TCTGACATGAATGAATTATTATTATTTTTATTTTTCTTTTTTTTTTTACA
TTTTTGTATAGAAACAAATTCATTTAAACAAACTTATTATTATTATTTTT
ACAAAATATATATATGGAGATGCTCCCTCCCCCTGTGAACCCCCCAGTGC
CCCCGTGGGGCTGAGTCTGTGGGCCCATTCGGCCAAGCTGGATTCTGTGT
ACCTAGTACACAGGCATGACTGGGATCCCGTGTACCGAGTACACGACCCA
GGTATGTACCAAGTAGGCACCCTTGGGCGCACCCACTGGGGCCAGGGGTC
GGGGGAGTGTTGGGAGCCTCCTCCCCACCCCACCTCCCTCACTTCACTGC
ATTCCAGATGGGACATGTTCCATAGCCTTGCTGGGGAAGGGCCCACTGCC
AACTCCCTCTGCCCCAGCCCCACCCTTGGCCATCTCCCTTTGGGAACTAG
GGGGCTGCTGGTGGGAAATGGGAGCCAGGGCAGATGTATGCATTCCTTTG
TGTCCCTGTAAATGTGGGACTACAAGAAGAGGAGCTGCCTGAGTGGTACT
TTCTCTTCCTGGTAATCCTCTGGCCCAGCCTCATGGCAGAATAGAGGTAT
TTTTAGGCTATTTTTGTAATATGGCTTCTGGTCAAAATCCCTGTGTAGCT
GAATTCCCAAGCCCTGCATTGTACAGCCCCCACTCCCCTCACCACCTAA
TAAAGGAATAGTTAACACTCAAAAAAAAAAAAAAAAAA In a NOTCH3-encoding mRNA sequence, each "T" in the sequence above would be a "U".

Another amino acid sequence for human NOTCH3 is publically available in the GenBank database under accession number AAB91371.1 and is as follows:

(SEQ ID No. 14)
MGPGARGRRRRRRPMSPPPPPPPVRALPLLLLLAGPGAAAPPCLDGSPCA

NGGRCTQLPSREAACLCPPGWVGERCQLEDPCHSGPCAGRGVCQSSVVAG

TARFSCRCPRGFRGPDCSLPDPCLSSPCAHGARCSVGPDGRFLCSCPPGY

QGRSCRSDVDECRVGEPCRHGGTCLNTPGSFRCQCPAGYTGPLCENPAVP

CAPSPCRNGGTCRQSGDLTYDCACLPGFEGQNCEVNVDDCPGHRCLNGGT

CVDGVNTYNCQCPPEWTGQFCTEDVDECQLQPNACHNGGTCFNTLGGHSC

VCVNGWTGESCSQNIDDCATAVCFHGATCHDRVASFYCACPMGKTGLLCH

LDDACVSNPCHEDAICDTNPVNGRAICTCPPGFTGGACDQDVDECSIGAN

PCEHLGRCVNTQGSFLCQCGRGYTGPRCETDVNECLSGPCRNQATCLDRI

GQFTCICMAGFTGTYCEVDIDECQSSPCVNGGVCKDRVNGFSCTCPSGFS

GSTCQLDVDECASTPCRNGAKCVDQPDGYECRCAEGFEGTLCDRNVDDCS

PDPCHHGRCVDGIASFSCACAPGYTGTRCESQVDECRSQPCRHGGKCLDL

VDKYLCRCPSGTTGVNCEVNIDDCASNPCTFGVCRDGINRYDCVCQPGFT

GPLCNVEINECASSPCGEGGSCVDGENGFRCLCPPGSLPPLCLPPSHPCA

HEPCSHGICYDAPGGFRCVCEPGWSGPRCSQSLARDACESQPCRAGGTCS

SDGMGFHCTCPPGVQGRQCELLSPCTPNPCEHGGRCESAPGQLPVCSCPQ

GWQGPRCQQDVDECAGPAPCGPHGICTNLAGSFSCTCHGGYTGPSCDQDI

NDCDPNPCLNGGSCQDGVGSFSCSCLPGFAGPRCARDVDECLSNPCGPGT

CTDHVASFTCTCPPGYGGFHCEQDLPDCSPSSCFNGGTCVDGVNSFSCLC

RPGYTGAHCQHEADPCLSRPCLHGGVCSAAHPGFRCTCLESFTGPQCQTL

VDWCSRQPCQNGGRCVQTGAYCLCPPGWSGRLCDIRSLPCREAAAQIGVR

LEQLCQAGGQCVDEDSSHYCVCPEGRTGSHCEQEVDPCLAQPCQHGGTCR

GYMGGYMCECLPGYNGDNCEDDVDECASQPCQHGGSCIDLVARYLCSCPP

GTLGVLCEINEDDCGPGPPPLDSGPRCLHNGTCVDLVGGFRCTCPPGYTGL

RCEADINECRSGACHAAHTRDCLQDPGGGFRCLCHAGFSGPRCQTVLSPC

ESQPCQHGGQCRPSPGPGGGLTFTCHCAQPFWGPRCERVARSCRELQCPV

GVPCQQTPRGPRCACPPGLSGPSCRSFPGSPPGASNASCAAAPCLHGGSC

RPAPLAPFFRCACAQGWTGPRCEAPAAAPEVSEEPRCPRAACQAKRGDQR

CDRECNSPGCGWDGGDCSLSVGDPWRQCEALQCWRLFNNSRCDPACSSPA

CLYDNFDCHAGGRERTCNPVYEKYCADHFADGRCDQGCNTEECGWDGLDC

ASEVPALLARGVLVLTVLLPPEELLRSSADFLQRLSAILRTSLRFRLDAH

GQAMVFPYHRPSPGSEPRARRELAPEVIGSVVMLEIDNRLCLQSPENDHC

FPDAQSAADYLGALSAVERLDFPYPLRDVRGEPLEPPEPSVPLLPLLVAG

AVLLLVILVLGVMVARRKREHSTLWFPEGFSLHKDVASGHKGRREPVGQD

ALGMKNMAKGESLMGEVATDWMDTECPEAKRLKVEEPGMGAEEAVDCRQW

TQHHLVAADIRVAPAMALTPPQGDADADGMDVNVRGPDGFTPLMLASFCG

GALEPMPTEEDEADDTSASIISDLICQGAQLGARTDRTGETALHLAARYA

RADAAKRLLDAGADTNAQDHSGRTPLHTAVTADAQGVFQILIRNRSTDLD

ARMADGSTALILAARLAVEGMVEELIASHADVNAVDELGKSALHWAAAVN

NVEATLALLKNGANKDMQDSKEETPLFLAAREGSYEAAKLLLDHFANREI

TDHLDRLPRDVAQERLHQDIVRLLDQPSGPRSPPGPHGLGPLLCPPGAFL

PGLKAAQSGSKKSRRPPGKAGLGPQGPRGRGKKLTLACPGPLADSSVTLS

PVDSLDSPRPFGGPPASPGGFPLEGPYAAATATAVSLAQLGGPRAGLGR

QPPGGCVLSLGLLNPVAVPLDWARLPPPAPPGPSFLLPLAPGPQLLNPGT

PVSPQERPPPYLAVPGHGEEYPVAGAHSSPPKARFLRVPSEHPYLTPSPE

SPEHWASPSPPSLSDWSESTPSPATATGAMATTTGALPAQPLPLSVPSSL

AQAQTQLGPQPEVTPKRQVLA

A nucleotide sequence that encodes human NOTCH3 is publically available in the GenBank database under accession number U97669.1 (SEQ ID NO: 4) and is as follows (the start and stop codons are underlined and bolded):

ACGCGGCGCGGAGGCTGGCCCGGGACGCGCCCGGAGCCCAGGGAAGGAGG

GAGGAGGGGAGGGTCGCGGCCGGCCGCCATGGGGCCGGGGGCCCGTGGCC

GCCGCCGCCGTCGCCCGATGTCGCCGCCACCGCCACCGCCACCCGTG

CGGGCGCTGCCCCTGCTGCTGCTGCTAGCGGGGCCGGGGGCTGCAGCCCC

CCCTTGCCTGGACGGAAGCCCGTGTGCAAATGGAGGTCGTTGCACCCAGC

TGCCCTCCCGGGAGGCTGCCTGCCTGTGCCCGCCTGGCTGGGTGGGTGAG

CGGTGTCAGCTGGAGGACCCCTGTCACTCAGGCCCCTGTGCTGGCCGTGG

TGTCTGCCAGAGTTCAGTGGTGGCTGGCACCGCCCGATTCTCATGCCGGT

GCCCCCGTGGCTTCCGAGGCCCTGACTGCTCCCTGCCAGATCCCTGCCTC

AGCAGCCCTTGTGCCCACGGTGCCCGCTGCTCAGTGGGGCCCGATGGACG

CTTCCTCTGCTCCTGCCCACCTGGCTACCAGGGCCGCAGCTGCCGAAGCG

ACGTGGATGAGTGCCGGGTGGGTGAGCCCTGCCGCCATGGTGGCACCTGC

CTCAACACACCTGGCTCCTTCCGCTGCCAGTGTCCAGCTGGCTACACAGG

GCCACTATGTGAGAACCCCGCGGTGCCCTGTGCGCCCTCACCATGCCGTA

ACGGGGGCACCTGCAGGCAGAGTGGCGACCTCACTTACGACTGTGCCTGT

CTTCCTGGGTTTGAGGGTCAGAATTGTGAAGTGAACGTGGACGACTGTCC

AGGACACCGATGTCTCAATGGGGGACATGCGTGGATGCGTCAACACCT

ATAACTGCCAGTGCCCTCCTGAGTGGACAGGCCAGTTCTGCACGGAGGAC

GTGGATGAGTGTCAGCTGCAGCCCAACGCCTGCCACAATGGGGGTACCTG

CTTCAACACGCTGGGTGGCCACAGCTGCGTGTGTGTCAATGGCTGGACAG

GTGAGAGCTGCAGTCAGAATATCGATGACTGTGCCACAGCCGTGTGCTTC

CATGGGGCCACCTGCCATGACCGCGTGGCTTCTTTCTACTGTGCCTGCCC

CATGGGCAAGACTGGCCTCCTGTGTCACCTGGATGACGCCTGTGTCAGCA

ACCCCTGCCACGAGGATGCTATCTGTGACACAAATCCGGTGAACGGCCGG

GCCATTTGCACCTGTCCTCCCGGCTTCACGGGTGGGCATGTGACCAGGA

TGTGGACGAGTGCTCTATCGGCGCCAACCCCTGCGAGCACTTGGGCAGGT

GCGTGAACACGCAGGGCTCCTTCCTGTGCCAGTGCGGTCGTGGCTACACT

GGACCTCGCTGTGAGACCGATGTCAACGAGTGTCTGTCGGGGCCCTGCCG

AAACCAGGCCACGTGCCTCGACCGCATAGGCCAGTTCACCTGTATCTGTA

TGGCAGGCTTCACAGGAACCTATTGCGAGGTGGACATTGACGAGTGTCAG

AGTAGCCCCTGTGTCAACGGTGGGGTCTGCAAGGACCGAGTCAATGGCTT
CAGCTGCACCTGCCCCTCGGGCTTCAGCGGCTCCACGTGTCAGCTGGACG
TGGACGAATGCGCCAGCACGCCCTGCAGGAATGCGCCAAATGCGTGGAC
CAGCCCGATGGCTACGAGTGCCGCTGTGCCGAGGGCTTTGAGGGCACGCT
GTGTGATCGCAACGTGGACGACTGCTCCCCTGACCCATGCCACCATGGTC
GCTGCGTGGATGGCATCGCCAGCTTCTCATGTGCCTGTGCTCCTGGCTAC
ACGGGCACACGCTGCGAGAGCCAGGTGGACGAATGCCGCAGCCAGCCCTG
CCGCCATGGCGGCAAATGCCTAGACCTGGTGGACAAGTACCTCTGCCGCT
GCCCTTCTGGGACCACAGGTGTGAACTGCGAAGTGAACATTGACGACTGT
GCCAGCAACCCCTGCACCTTTGGAGTCTGCCGTGATGGCATCAACCGCTA
CGACTGTGTCTGCCAACCTGGCTTCACAGGGCCCCTTTGTAACGTGGAGA
TCAATGAGTGTGCTTCCAGCCCATGCGGCGAGGGAGGTTCCTGTGTGGAT
GGGGAAAATGGCTTCCGCTGCCTCTGCCCGCCTGGCTCCTTGCCCCCACT
CTGCCTCCCCCGAGCCATCCCTGTGCCCATGAGCCCTGCAGTCACGGCA
TCTGCTATGATGCACCTGGCGGGTTCCGCTGTGTGTGTGAGCCTGGCTGG
AGTGGCCCCGCTGCAGCCAGAGCCTGGCCCGAGACGCCTGTGAGTCCCA
GCCGTGCAGGGCCGGTGGGACATGCAGCAGCGATGGAATGGGTTTCCACT
GCACCTGCCCGCCTGGTGTCCAGGGACGTCAGTGTGAACTCCTCTCCCCC
TGCACCCCGAACCCCTGTGAGCATGGGGGCCGCTGCGAGTCTGCCCCTGG
CCAGCTGCCTGTCTGCTCCTGCCCCCAGGGCTGGCAAGGCCCACGATGCC
AGCAGGATGTGGACGAGTGTGCTGGCCCCGCACCCTGTGGCCCTCATGGT
ATCTGCACCAACCTGGCAGGGAGTTTCAGCTGCACCTGCCATGGAGGGTA
CACTGGCCCTTCCTGTGATCAGGACATCAATGACTGTGACCCCAACCCAT
GCCTGAACGGTGGCTCGTGCCAAGACGGCGTGGGCTCCTTTTCCTGCTCC
TGCCTCCCTGGTTTCGCCGGCCCACGATGCGCCCGCGATGTGGATGAGTG
CCTGAGCAACCCCTGCGGCCCGGGCACCTGTACCGACCACGTGGCCTCCT
TCACCTGCACCTGCCCGCCGGGCTACGGAGGCTTCCACTGCGAACAGGAC
CTGCCCGACTGCAGCCCCAGCTCCTGCTTCAATGGCGGGACCTGTGTGGA
CGGCGTGAACTCGTTCAGCTGCCTGTGCCGTCCCGGCTACACAGGAGCCC
ACTGCCAACATGAGGCAGACCCCTGCCTCTCGCGGCCCTGCCTACACGGG
GGCGTCTGCAGCGCCGCCCACCCTGGCTTCCGCTGCACCTGCCTCGAGAG
CTTCACGGGCCCGCAGTGCCAGACGCTGGTGGATTGGTGCAGCCGCCAGC
CTTGTCAAAACGGGGGTCGCTGCGTCCAGACTGGGGCCTATTGCCTTTGT
CCCCCTGGATGGAGCGGACGCCTCTGTGACATCCGAAGCTTGCCCTGCAG
GGAGGCCGCAGCCCAGATCGGGGTGCGGCTGGAGCAGCTGTGTCAGGCGG
GTGGGCAGTGTGTGGATGAAGACAGCTCCCACTACTGCGTGTGCCCAGAG
GGCCGTACTGGTAGCCACTGTGAGCAGGAGGTGGACCCCTGCTTGGCCCA
GCCCTGCCAGCATGGGGGGACCTGCCGTGGCTATATGGGGGGCTACATGT
GTGAGTGTCTTCCTGGCTACAATGGTGATAACTGTGAGGACGACGTGGAC
GAGTGTGCCTCCCAGCCCTGCCAGCACGGGGGTTCATGCATTGACCTCGT
GGCCCGCTATCTCTGCTCCTGTCCCCCAGGAACGCTGGGGGTGCTCTGCG

AGATTAATGAGGATGACTGCGGCCCAGGCCCACCGCTGGACTCAGGGCCC
CGGTGCCTACACAATGGCACCTGCGTGGACCTGGTGGGTGGTTTCCGCTG
CACCTGTCCCCCAGGATACACTGGTTTGCGCTGCGAGGCAGACATCAATG
AGTGTCGCTCAGGTGCCTGCCACGCGGCACACACCCGGGACTGCCTGCAG
GACCCAGGCGGAGGTTTCCGTTGCCTTTGTCATGCTGGCTTCTCAGGTCC
TCGCTGTCAGACTGTCCTGTCTCCCTGCGAGTCCCAGCCATGCCAGCATG
GAGGCCAGTGCCGTCCTAGCCCGGGTCCTGGGGGTGGGCTGACCTTCACC
TGTCACTGTGCCCAGCCGTTCTGGGGTCCGCGTTGCGAGCGGGTGGCGCG
CTCCTGCCGGGAGCTGCAGTGCCCGGTGGGCGTCCCATGCCAGCAGACGC
CCCGCGGGCCGCGCTGCGCCTGCCCCCCAGGGTTGTCGGGACCCTCCTGC
CGCAGCTTCCCGGGGTCGCCGCCGGGGGCCAGCAACGCCAGCTGCGCGGC
CGCCCCCTGTCTCCACGGGGGCTCCTGCCGCCCCGCGCCGCTCGCGCCCT
TCTTCCGCTGCGCTTGCGCGCAGGGCTGGACCGGGCCGCGCTGCGAGGCG
CCCGCCGCGGCACCCGAGGTCTCGGAGGAGCCGCGGTGCCCGCGCGCCGC
CTGCCAGGCCAAGCGCGGGGACCAGCGCTGCGACCGCGAGTGCAACAGCC
CAGGCTGCGGCTGGGACGGCGGCGACTGCTCGCTGAGCGTGGGCGACCCC
TGGCGGCAATGCGAGGCGCTGCAGTGCTGGCGCCTCTTCAACAACAGCCG
CTGCGACCCCGCCTGCAGCTCGCCCGCCTGCCTCTACGACAACTTCGACT
GCCACGCCGGTGGCCGCGAGCGCACTTGCAACCCGGTGTACGAGAAGTAC
TGCGCCGACCACTTTGCCGACGGCCGCTGCGACCAGGGCTGCAACACGGA
GGAGTGCGGCTGGGATGGGCTGGATTGTGCCAGCGAGGTGCCGGCCCTGC
TGGCCCGCGGCGTGCTGGTGCTCACAGTGCTGCTGCCGCCGGAGGAGCTA
CTGCGTTCCAGCGCCGACTTTCTGCAGCGGCTCAGCGCCATCCTGCGCAC
CTCGCTGCGCTTCCGCCTGGACGCGCACGGCCAGGCCATGGTCTTCCCTT
ACCACCGGCCTAGTCCTGGCTCCGAACCCCGGGCCCGTCGGGAGCTGGCC
CCCGAGGTGATCGGCTCGGTAGTAATGCTGGAGATTGACAACCGGCTCTG
CCTGCAGTCGCCTGAGAATGATCACTGCTTCCCCGATGCCCAGAGCGCCG
CTGACTACCTGGGAGCGTTGTCAGCGGTGGAGCGCCTGGACTTCCCGTAC
CCACTGCGGGACGTGCGGGGGAGCCGCTGGAGCCTCCAGAACCCAGCGT
CCCGCTGCTGCCACTGCTAGTGGCGGGCGCTGTCTTGCTGCTGGTCATTC
TCGTCCTGGGTGTCATGGTGGCCCGGCGCAAGCGCGAGCACAGCACCCTC
TGGTTCCCTGAGGGCTTCTCACTGCACAAGGACGTGGCCTCTGGTCACAA
GGGCCGGCGGGAACCCGTGGGCCAGGACGCGCTGGGCATGAAGAACATGG
CCAAGGGTGAGAGCCTGATGGGGGAGGTGGCCACAGACTGGATGGACACA
GAGTGCCCAGAGGCCAAGCGGCTAAAGGTAGAGGAGCCAGGCATGGGGC
TGAGGAGGCTGTGGATTGCCGTCAGTGGACTCAACACCATCTGGTTGCTG
CTGACATCCGCGTGGCACCAGCCATGGCACTGACACCACCACAGGGCGAC
GCAGATGCTGATGGCATGGATGTCAATGTGCGTGGCCCAGATGGCTTCAC
CCCGCTAATGCTGGCTTCCTTCTGTGGGGGGCTCTGGAGCCAATGCCAA
CTGAAGAGGATGAGGCAGATGACACATCAGCTAGCATCATCTCCGACCTG

-continued
ATCTGCCAGGGGGCTCAGCTTGGGCACGGACTGACCGTACTGGCGAGAC

TGCTTTGCACCTGGCTGCCCGTTATGCCCGTGCTGATGCAGCCAAGCGGC

TGCTGGATGCTGGGGCAGACACCAATGCCCAGGACCACTCAGGCCGCACT

CCCCTGCACACAGCTGTCACAGCCGATGCCCAGGGTGTCTTCCAGATTCT

CATCCGAAACCGCTCTACAGACTTGGATGCCCGCATGGCAGATGGCTCAA

CGGCACTGATCCTGGCGGCCCGCCTGGCAGTAGAGGGCATGGTGGAAGAG

CTCATCGCCAGCCATGCTGATGTCAATGCTGTGGATGAGCTTGGGAAATC

AGCCTTACACTGGGCTGCGGCTGTGAACAACGTGGAAGCCACTTTGGCCC

TGCTCAAAAATGGAGCCAATAAGGACATGCAGGATAGCAAGGAGGAGACC

CCCCTATTCCTGGCCGCCCGCGAGGGCAGCTATGAGGCTGCCAAGCTGCT

GTTGGACCACTTTGCCAACCGTGAGATCACCGACCACCTGGACAGGCTGC

CGCGGGACGTAGCCCAGGAGAGACTGCACCAGGACATCGTGCGCTTGCTG

GATCAACCCAGTGGGCCCCGCAGCCCCCCGGTCCCCACGGCCTGGGGCC

TCTGCTCTGTCCTCCAGGGGCCTTCCTCCCTGGCCTCAAAGCGGCACAGT

CGGGGTCCAAGAAGAGCAGGAGGCCCCCGGGAAGGCGGGGCTGGGGCCG

CAGGGGCCCCGGGGCGGGGCAAGAAGCTGACGCTGGCCTGCCCGGGCCC

CCTGGCTGACAGCTCGGTCACGCTGTCGCCCGTGGACTCGCTGGACTCCC

CGCGGCCTTTCGGTGGGCCCCCTGCTTCCCCTGGTGGCTTCCCCCTTGAG

GGGCCCTATGCAGCTGCCACTGCCACTGCAGTGTCTCTGGCACAGCTTGG

TGGCCCAGGCCGGGCAGGTCTAGGGCGCCAGCCCCCTGGAGGATGTGTAC

TCAGCCTGGGCCTGCTGAACCCTGTGGCTGTGCCCCTCGATTGGGCCCGG

CTGCCCCCACCTGCCCCTCCAGGCCCCTCGTTCCTGCTGCCACTGGCGCC

GGGACCCCAGCTGCTCAACCCAGGGACCCCCGTCTCCCCGCAGGAGCGGC

CCCCGCCTTACCTGGCAGTCCCAGGACATGGCGAGGAGTACCCGGTGGCT

GGGGCACACAGCAGCCCCCCAAAGGCCCGCTTCCTGCGGGTTCCCAGTGA

GCACCCTTACCTGACCCCATCCCCCGAATCCCCTGAGCACTGGGCCAGCC

CCTCACCTCCCTCCCTCTCAGACTGGTCCGAATCCACGCCTAGCCCAGCC

ACTGCCACTGGGGCCATGGCCACCACCACTGGGGCACTGCCTGCCCAGCC

ACTTCCCTTGTCTGTTCCCAGCTCCCTTGCTCAGGCCCAGACCCAGCTGG

GGCCCCAGCCGGAAGTTACCCCCAAGAGGCAAGTGTTGGCTGAGACGCT

CGTCAGTTCTTAGATCTTGGGGGCCTAAAGAGACCCCCGTCCTGCCTCCT

TTCTTTCTCTGTCTCTTCCTTCCTTTTAGTCTTTTTCATCCTCTTCTCTT

TCCACCAACCCTCCTGCATCCTTGCCTTGCAGCGTGACCGAGATAGGTCA

TCAGCCCAGGGCTTCAGTCTTCCTTTATTTATAATGGGTGGGGGCTACCA

CCCACCCTCTCAGTCTTGTGAAGAGTCTGGGACCTCCTTCTTCCCCACTT

CTCTCTTCCCTCATTCCTTTCTCTCTCCTTCTGGCCTCTCATTTCCTTAC

ACTCTGACATGAATGAATTATTATTATTTTTCTTTTTCTTTTTTTTTTA

CATTTTGTATAGAAACAAATTCATTTAAACAAACTTATTATTATTATTTT

TTACAAAATATATATATGGAGATGCTCCCTCCCCCTGTGAACCCCCCAGT

GCCCCCGTGGGGCTGAGTCTGTGGGCCCATTCGGCCAAGCTGGATTCTGT

GTACCTAGTACACAGGCATGACTGGGATCCCGTGTACCGAGTACACGACC

-continued
CAGGTATGTACCAAGTAGGCACCCTTGGGCGCACCCACTGGGGCCAGGGG

TCGGGGGAGTGTTGGGAGCCTCCTCCCCACCCCACCTCCCTCACTTCACT

GCATTCCAGATTGGACATGTTCCATAGCCTTGCTGGGGAAGGGCCCACTG

CCAACTCCCTCTGCCCCAGCCCCACCCTTGGCCATCTCCCTTTGGGAACT

AGGGGGCTGCTGGTGGGAAATGGGAGCCAGGGCAGATGTATGCATTCCTT

TATGTCCCTGTAAATGTGGGACTACAAGAAGAGGAGCTGCCTGAGTGGTA

CTTTCTCTTCCTGGTAATCCTCTGGCCCAGCCTTATGGCAGAATAGAGGT

ATTTTTAGGCTATTTTTGTAATATGGCTTCTGGTCAAAATCCCTGTGTAG

CTGAATTCCCAAGCCCTGCATTGTACAGCCCCCCACTCCCCTCACCACCT

AATAAAGGAATAGTTAACACTCAAAAAAAAAAAAAAAAAAA

In a NOTCH3-encoding mRNA sequence, each "T" in the sequence above would be a "U".

The human NOTCH3 ectodomain sequence comprises amino acid positions 40 to 1571 of accession number Q9UM47. With respect to embodiments relating to CADA-SIL, the ectodomain comprises the extracellular domain until the furin cleavage site. This excludes the signal peptide from positions 1 to 39 and also excludes the 1572 to 2321 amino acid region encompassing a small portion that is extracellular, the transmembrane domain, and the intracellular domain.

An amino acid sequence for human N3ECD is:

```
                                            (SEQ ID NO: 5)
APPCLDGSPC ANGGRCTQLP SREAACLCPP GWVGERCQLE

DPCHSGPCAG RGVCQSSVVAGTARFSCRCP RGFRGPDCSL

PDPCLSSPCAHGARCSVGPD GRFLCSCPPG YQGRSCRSDVD

ECRVGEPCR HGGTCLNTPG SFRCQCPAGY TGPLCENPAV

PCAPSPCRNG GTCRQSGDLTYDCACLPGFE GQNCEVNVDD

CPGHRCLNGG TCVDGVNTYN CQCPPEWTGQ FCTEDVDECQ

LQPNACHNGG TCFNTLGGHS CVCVNGWTGE SCSQNIDDCA

TAVCFHGATC HDRVASFYCA CPMGKTGLLC HLDDACVSNP

CHEDAICDTN PVNGRAICTC PPGFTGGACD QDVDECSIGA

NPCEHLGRCV NTQGSFLCQC GRGYTGPRCE TDVNECLSGP

CRNQATCLDRIGQFTCICMAGFTGTYCEVD IDECQSSPCV

NGGVCKDRVN GFSCTCPSGF SGSTCQLDVD ECASTPCRNG

AKCVDQPDGY ECRCAEGFEG TLCDRNVDDC SPDPCHHGRC

VDGIASFSCA CAPGYTGTRCESQVDECRSQ PCRHGGKCLD

LVDKYLCRCP SGTTGVNCEV NIDDCASNPC TFGVCRDGIN

RYDCVCQPGF TGPLCNVEIN ECASSPCGEG GSCVDGENGF

RCLCPPGSLP PLCLPPSHPCAHEPCSHGIC YDAPGGFRCV

CEPGWSGPRC SQSLARDACE SQPCRAGGTC SSDGMGFHCT

CPPGVQGRQC ELLSPCTPNP CEHGGRCESA PGQLPVCSCP

QGWQGPRCQQ DVDECAGPAPCGPHGICTNL AGSFSCTCHG

GYTGPSCDQD INDCDPNPCL NGGSCQDGVG SFSCSCLPGF
```

```
AGPRCARDVD ECLSNPCGPG TCTDHVASFT CTCPPGYGGF

HCEQDLPDCS PSSCFNGGTC VDGVNSFSCL CRPGYTGAHC

QHEADPCLSR PCLHGGVCSA AHPGFRCTCL ESFTGPQCQT

LVDWCSRQPC QNGGRCVQTG AYCLCPPGWS GRLCDIRSLP

CREAAAQIGV RLEQLCQAGGQCVDEDSSHY CVCPEGRTGS

HCEQEVDPCL AQPCQHGGTC RGYMGGYMCE CLPGYNGDNC

EDDVDECASQ PCQHGGSCID LVARYLCSCP PGTLGVLCEI

NEDDCGPGPP LDSGPRCLHNGTCVDLVGGF RCTCPPGYTG

LRCEADINEC RSGACHAAHT RDCLQDPGGG FRCLCHAGFS

GPRCQTVLSP CESQPCQHGG QCRPSPGPGG GLTFTCHCAQ

PFWGPRCERV ARSCRELQCPVGVPCQQTPR GPRCACPPGL

SGPSCRSFPG SPPGASNASC AAAPCLHGGS CRPAPLAPFF

RCACAQGWTG PRCEAPAAAP EVSEEPRCPR AACQAKRGDQ

RCDRECNSPG CGWDGGDCSLSVGDPWRQCE ALQCWRLFNN

SRCDPACSSP ACLYDNFDCH AGGRERTCNP VYEKYCADHF

ADGRCDQGCN TEECGWDGLD CASEVPALLA RGVLVLTVLL

PPEELLRSSA DFLQRLSAILR TSLRFRLDAHGQAMVFPYHR

PSPGSEPRARR
```

The amino acid sequence for mouse N3ECD runs from positions 40 to 1572 of the amino acid sequence that is available from accession number Q61982 (SEQ ID NO: 6), and is as follows:

```
                                         (SEQ ID NO: 6)
APPCLDGSPC ANGGRCTHQQ PSLEAACLCL PGWVGERCQL

EDPCHSGPCA GRGVCQSSVVAGTARFSCRC LRGFQGPDCS

QPDPCVSRPC VHGAPCSVGP DGRFACACPP GYQGQSCQSD

IDECRSGTTC RHGGTCLNTP GSFRCQCPLG YTGLLCENPV

VPCAPSPCRN GGTCRQSSDVTYDCACLPGF EGQNCEVNVD

DCPGHRCLNG GTCVDGVNTY NCQCPPEWTG QFCTEDVDEC

QLQPNACHNG GTCFNLLGGH SCVCVNGWTGESCSQNIDDC

ATAVCFHGAT CHDRVASFYC ACPMGKTGLL CHLDDACVSN

PCHEDAICDT NPVSGRAICT CPPGFTGGAC DQDVDECSIG

ANPCEHLGRC VNTQGSFLCQ CGRGYTGPRC ETDVNECLSG

PCRNQATCLD RIGQFTCICMAGFTGTYCEV DIDECQSSPC

VNGGVCKDRV NGFSCTCPSG FSGSMCQLDV DECASTPCRN

GAKCVDQPDG YECRCAEGFE GTLCERNVDD CSPDPCHHGR

CVDGIASFSC ACAPGYTGIRCESQVDECRS QPCRYGGKCL

DLVDKYLCRC PPGTTGVNCE VNIDDCASNP CTFGVCRDGI

NRYDCVCQPG FTGPLCNVEINECASSPCGE GGSCVDGENG

FHCLCPPGSL PPLCLPANHPCAHKPCSHGV CHDAPGGFRC

VCEPGWSGPR CSQSLAPDAC ESQPCQAGGT CTSDGIGFRC

TCAPGFQGHQ CEVLSPCTPS LCEHGGHCES DPDRLTVCSC

PPGWQGPRCQ QDVDECAGASPCGPHGTCTN LPGNFRCICH

RGYTGPFCDQ DIDDCDPNPC LHGGSCQDGV GSFSCSCLDG

FAGPRCARDV DECLSSPCGP GTCTDHVASF TCACPPGYGG

FHCEIDLPDC SPSSCFNGGT CVDGVSSFSC LCRPGYTGTH

CQYEADPCFS RPCLHGGICN PTHPGFECTC REGFTGSQCQ

NPVDWCSQAP CQNGGRCVQT GAYCICPPGW SGRLCDIQSL

PCTEAAAQMG VRLEQLCQEGGKCIDKGRSH YCVCPEGRTG

SHCEHEVDPC TAQPCQHGGT CRGYMGGYVC ECPAGYAGDS

CEDNIDECAS QPCQNGGSCI DLVARYLCSC PPGTLGVLCE

INEDDCDLGP SLDSGVQCLHNGTCVDLVGG FRCNCPPGYT

GLHCEADINE CRPGACHAAH TRDCLQDPGG HFRCVCHPGF

TGPRCQIALS PCESQPCQHG GQCRHSLGRG GGLTFTCHCV

PPFWGLRCER VARSCRELQCPVGIPCQQTA RGPRCACPPG

LSGPSCRVSR ASPSGATNAS CASAPCLHGG SCLPVQSVPF

FRCVCAPGWG GPRCETPSAA PEVPEEPRCP RAACQAKRGD

QNCDRECNTP GCGWDGGDCSLNVDDPWRQC EALQCWRLFN

NSRCDPACSS PACLYDNFDC YSGGRDRTCN PVYEKYCADH

FADGRCDQGC NTEECGWDGL DCASEVPALL ARGVLVLTVL

LPPEELLRSS ADFLQRLSAIL RTSLRFRLDARGQAMVFPYH

RPSPGSESRVRR
```

IGFBP-1

IGFBP-1 is a member of the insulin-like growth factor binding protein (IGFBP) family and encodes a protein with an IGFBP domain and a thyroglobulin type-I domain. The protein binds both insulin-like growth factors (IGFs) I and II and circulates in the plasma. Binding of this protein prolongs the half-life of the IGFs and alters their interaction with cell surface receptors.

An amino acid sequence for human IGFBP-1 is publically available in the UniProt database under accession number P08833 (SEQ ID NO: 7) and is as follows:

```
MSEVPVARVWLVLLLLTVQVGVTAGAPWQCAPCSAEKLALCPPVSASCSE

VTRSAGCGCCPMCALPLGAACGVATARCARGLSCRALPGEQQPLHALTRG

QGACVQESDASAPHAAEAGSPESPESTEITEEELLDNFHLMAPSEEDHSI

LWDAISTYDGSKALHVTNIKKWKEPCRIELYRVVESLAKAQETSGEEISK

FYLPNCNKNGFYHSRQCETSMDGEAGLCWCVYPWNGKRIPGSPEIRGDPN

CQIYFNVQN
```

A nucleotide sequence that encodes human IGFBP-1 is publically available in the GenBank database under accession number NM 000596.2 (SEQ ID NO: 8) and is as follows (the start and stop codons are underlined and bolded):

```
GGTGCACTAGCAAAACAAACTTATTTTGAACACTCAGCTCCTAGCGTGCG

GCGCTGCCAATCATTAACCTCCTGGTGCAAGTGGCGCGGCCTGTGCCCTT
```

-continued

```
TATAAGGTGCGCGCTGTGTCCAGCGAGCATCGGCCACCGCCATCCCATCC

AGCGAGCATCTGCCGCCGCGCCGCCGCCACCCTCCCAGAGAGCACTGGCC

ACCGCTCCACCATCACTTGCCCAGAGTTTGGGCCACCGCCCGCCGCCACC

AGCCCAGAGAGCATCGGCCCCTGTCTGCTGCTCGCGCCTGGAATGTCAG

AGGTCCCCGTTGCTCGCGTCTGGCTGGTACTGCTCCTGCTGACTGTCCAG

GTCGGCGTGACAGCCGGCGCTCCGTGGCAGTGCGCGCCCTGCTCCGCCGA

GAAGCTCGCGCTCTGCCCGCCGGTGTCCGCCTCGTGCTCGGAGGTCACCC

GGTCCGCCGGCTGCGGCTGTTGCCCGATGTGCGCCCTGCCTCTGGGCGCC

GCGTGCGGCGTGGCGACTGCACGCTGCGCCCGGGGACTCAGTTGCCGCGC

GCTGCCGGGGAGCAGCAACCTCTGCACGCCCTCACCCGCGGCCAAGGCG

CCTGCGTGCAGGAGTCTGACGCCTCCGCTCCCCATGCTGCAGAGGCAGGG

AGCCCTGAAAGCCCAGAGAGCACGGAGATAACTGAGGAGGAGCTCCTGGA

TAATTTCCATCTGATGGCCCCTTCTGAAGAGGATCATTCCATCCTTTGGG

ACGCCATCAGTACCTATGATGGCTCGAAGGCTCTCCATGTCACCAACATC

AAAAAATGGAAGGAGCCCTGCCGAATAGAACTCTACAGAGTCGTAGAGAG

TTTAGCCAAGGCACAGGAGACATCAGGAGAAGAAATTTCCAAATTTTACC

TGCCAAACTGCAACAAGAATGGATTTTATCACAGCAGACAGTGTGAGACA

TCCATGGATGGAGAGGCGGGACTCTGCTGGTGCGTCTACCCTTGGAATGG

GAAGAGGATCCCTGGGTCTCCAGAGATCAGGGGAGACCCCAACTGCCAGA

TATATTTTAATGTACAAAACTGAAACCAGATGAAATAATGTTCTGTCACG

TGAAATATTTAAGTATATAGTATATTTATACTCTAGAACATGCACATTTA

TATATATATGTATATGTATATATATATAGTAACTACTTTTTATACTCCAT

ACATAACTTGATATAGAAAGCTGTTTATTTATTCACTGTAAGTTTATTTT

TTCTACACAGTAAAAACTTGTACTATGTTAATAACTTGTCCTATGTCAAT

TTGTATATCATGAAACACTTCTCATCATATTGTATGTAAGTAATTGCATT

TCTGCTCTTCCAAAGCTCCTGCGTCTGTTTTTAAAGAGCATGGAAAAATA

CTGCCTAGAAAATGCAAAATGAAATAAGAGAGTAGTTTTTCAGCTAGT

TTGAAGGAGGACGGTTAACTTGTATATTCCACCATTCACATTTGATGTAC

ATGTGTAGGGAAAGTTAAAAGTGTTGATTACATAATCAAAGCTACCTGTG

GTGATGTTGCCACCTGTTAAAATGTACACTGGATATGTTGTTAAACACGT

GTCTATAATGGAAACATTTACAATAAATATTCTGCATGGAAATACTGTTA

AAAAAAAAAA
```

HTRA1

HTRA1 is a serine protease with a variety of targets, including extracellular matrix proteins such as fibronectin. HTRA1-generated fibronectin fragments further induce synovial cells to up-regulate matrix metalloproteinase-1 (MMP1) and matrix metalloproteinase-3 (MMP3) production. HTRA1 may also degrade proteoglycans, such as aggrecan, decorin and fibromodulin. Through cleavage of proteoglycans, HTRA1 may release soluble fibroblast growth factor (FGF)-glycosaminoglycan complexes that promote the range and intensity of FGF signals in the extracellular space. HTRA1 is also thought to regulate the availability of insulin-like growth factors (IGFs) by cleaving IGF-binding proteins. HTRA1 is further believed to inhibit signaling mediated by transforming growth factor beta (TGF-β) family members. This activity requires the integrity of the catalytic site, although it is unclear whether TGF-β proteins are themselves degraded. By acting on TGF-β signaling, HTRA1 may regulate many physiological processes, including retinal angiogenesis and neuronal survival and maturation during development. Intracellularly, HTRA1 degrades Tuberous Sclerosis Complex 2 (TSC2), leading to the activation of TSC2 downstream targets.

An amino acid sequence for human HTRA1 is publically available in the UniProt database under accession number Q92743 (SEQ ID NO: 9) and is as follows:

```
MQIPRAALLPLLLLLLAAPASAQLSRAGRSAPLAAGCPDRCEPARCPPQP

EHCEGGRARDACGCCEVCGAPEGAACGLQEGPCGEGLQCVVPFGVPASAT

VRRRAQAGLCVCASSEPVCGSDANTYANLCQLRAASRRSERLHRPPVIVL

QRGACGQGQEDPNSLRHKYNFIADVVEKIAPAVVHIELFRKLPFSKREVP

VASGSGFIVSEDGLIVTNAHVVTNKHRVKVELKNGATYEAKIKDVDEKAD

IALIKIDHQGKLPVLLLGRSSELRPGEFVVAIGSPFSLQNTVTTGIVSTT

QRGGKELGLRNSDMDYIQTDAIINYGNSGGPLVNLDGEVIGINTLKVTAG

ISFAIPSDKIKKFLTESHDRQAKGKAITKKKYIGIRMMSLTSSKAKELKD

RHRDFPDVISGAYIIEVIPDTPAEAGGLKENDVIISINGQSVVSANDVSD

VIKRESTLNMVVRRGNEDIMITVIPEEIDP
```

In the sequence shown above, positions 1-22 (SEQ ID NO: 10) correspond to the signal peptide, positions 204-364 (SEQ ID NO: 11) correspond to a serine protease domain.

A nucleotide sequence that encodes human HTRA1 is publically available in the GenBank database under accession number NM 002775.4 (SEQ ID NO: 12) and is as follows (the start and stop codons are underlined and bolded):

```
CAATGGGCTGGGCCGCGCGGCCGCGCGCACTCGCACCCGCTGCCCCCGAG

GCCCTCCTGCACTCTCCCCGGCGCCGCTCTCCGGCCCTCGCCCTGTCCGC

CGCCACCGCCGCCGCCGCCAGAGTCGCCATGCAGATCCCGCGCGCCGCTC

TTCTCCCGCTGCTGCTGCTGCTGCTGGCGGCGCCCGCCTCGGCGCAGCTG

TCCCGGGCCGGCCGCTCGGCGCCTTTGGCCGCCGGGTGCCCAGACCGCTG

CGAGCCGGCGCGCTGCCCGCCGCAGCCGGAGCACTGCGAGGGCGGCCGGG

CCCGGGACGCGTGCGGCTGCTGCGAGGTGTGCGGCGCGCCCGAGGGCGCC

GCGTGCGGCCTGCAGGAGGGCCCGTGCGGCGAGGGGCTGCAGTGCGTGGT

GCCCTTCGGGGTGCCAGCCTCGGCCACGGTGCGGCGGCGCGCGCAGGCCG

GCCTCTGTGTGTGCGCCAGCAGCGAGCCGGTGTGCGGCAGCGACGCCAAC

ACCTACGCCAACCTGTGCCAGCTGCGCGCCGCCAGCCGCCGCTCCGAGAG

GCTGCACCGGCCGCCGGTCATCGTCCTGCAGCGCGGAGCCTGCGGCCAAG

GGCAGGAAGATCCCAACAGTTTGCGCCATAAATATAACTTTATCGCGGAC

GTGGTGGAGAAGATCGCCCCTGCCGTGGTTCATATCGAATTGTTTCGCAA

GCTTCCGTTTTCTAAACGAGAGGTGCCGGTGGCTAGTGGGTCTGGGTTTA

TTGTGTCGGAAGATGGACTGATCGTGACAAATGCCCACGTGGTGACCAAC
```

```
-continued
AAGCACCGGGTCAAAGTTGAGCTGAAGAACGGTGCCACTTACGAAGCCAA

AATCAAGGATGTGGATGAGAAAGCAGACATCGCACTCATCAAAATTGACC

ACCAGGGCAAGCTGCCTGTCCTGCTGCTTGGCCGCTCCTCAGAGCTGCGG

CCGGGAGAGTTCGTGGTCGCCATCGGAAGCCCGTTTTCCCTTCAAAACAC

AGTCACCACCGGGATCGTGAGCACCACCCAGCGAGGCGGCAAAGAGCTGG

GGCTCCGCAACTCAGACATGGACTACATCCAGACCGACGCCATCATCAAC

TATGGAAACTCGGGAGGCCCGTTAGTAAACCTGGACGGTGAAGTGATTGG

AATTAACACTTTGAAAGTGACAGCTGGAATCTCCTTTGCAATCCCATCTG

ATAAGATTAAAAAGTTCCTCACGGAGTCCCATGACCGACAGGCCAAAGGA

AAAGCCATCACCAAGAAGAAGTATATTGGTATCCGAATGATGTCACTCAC

GTCCAGCAAAGCCAAAGAGCTGAAGGACCGGCACCGGGACTTCCCAGACG

TGATCTCAGGAGCGTATATAATTGAAGTAATTCCTGATACCCCAGCAGAA

GCTGGTGGTCTCAAGGAAAACGACGTCATAATCAGCATCAATGGACAGTC

CGTGGTCTCCGCCAATGATGTCAGCGACGTCATTAAAAGGGAAAGCACCC

TGAACATGGTGGTCCGCAGGGGTAATGAAGATATCATGATCACAGTGATT

CCCGAAGAAATTGACCCATAGGCAGAGGCATGAGCTGGACTTCATGTTTC

CCTCAAAGACTCTCCCGTGGATGACGGATGAGGACTCTGGGCTGCTGGAA

TAGGACACTCAAGACTTTTGACTGCCATTTTGTTTGTTCAGTGGAGACTC

CCTGGCCAACAGAATCCTTCTTGATAGTTTGCAGGCAAAACAAATGTAAT

GTTGCAGATCCGCAGGCAGAAGCTCTGCCCTTCTGTATCCTATGTATGCA

GTGTGCTTTTCTTGCCAGCTTGGGCCATTCTTGCTTAGACAGTCAGCAT

TTGTCTCCTCCTTTAACTGAGTCATCATCTTAGTCCAACTAATGCAGTCG

ATACAATGCGTAGATAGAAGAAGCCCCACGGGAGCCAGGATGGGACTGGT

CGTGTTTGTGCTTTCTCCAAGTCAGCACCCAAAGGTCAATGCACAGAGA

CCCCGGGTGGGTGAGCGCTGGCTTCTCAAACGGCCGAAGTTGCCTCTTTT

AGGAATCTCTTTGGAATTGGGAGCACGATGACTCTGAGTTTGAGCTATTA

AAGTACTTCTTACACATTGCAAAAAAAAAAAAAAAAAA
```

Exemplary SVDs and the Treatment Thereof

Aspects of the present subject matter relate to the treatment of SVDs using methods, compositions, systems, and kits described herein. For example, the present disclosure provides methods for monitoring the effectiveness of a treatment over time, as well as processes for determining whether the dose of a therapeutic compound should be increased or decreased.

Cerebral Small Vessel Disease

As used herein, the term "cerebral small vessel disease" or "cerebral SVD" refers to a group of pathological processes with various aetiologies that affect the small arteries, arterioles, venules, and capillaries of the brain. See, e.g., Pantoni (2010) Lancet Neurol, 9(7):689-701, the entire contents of which are incorporated herein by reference. Age-related and hypertension-related SVDs and cerebral amyloid angiopathy are the most common forms. The consequences of small vessel disease on the brain parenchyma are mainly lesions located in the subcortical structures such as lacunar infarcts, white matter lesions, large hemorrhages, and microbleeds. Small vessel disease has an important role in cerebrovascular disease and is a leading cause of cognitive decline and functional loss in the elderly.

Cerebral SVD may lead to vascular dementia (also known as vascular cognitive impairment). In vascular dementia, changes in thinking skills sometimes occur suddenly following strokes that block major brain blood vessels. See, e.g., Alzheimer's Association, Alzheimer's & Dementia, available at www.alz.org/dementia/vascular-dementia-symptoms.asp, the entire contents of which are incorporated herein by reference. Thinking problems also may begin as mild changes that worsen gradually as a result of multiple minor strokes or other conditions that affect smaller blood vessels, leading to cumulative damage. Symptoms can vary widely, depending on the severity of the blood vessel damage and the part of the brain affected. Memory loss may or may not be a significant symptom depending on the specific brain areas where blood flow is reduced. Vascular dementia symptoms may be most obvious when they happen soon after a major stroke. Sudden post-stroke changes in thinking and perception may include, e.g., (i) confusion; (ii) disorientation; (iii) trouble speaking or understanding speech; and/or (iv) vision loss. These changes may happen at the same time as stroke symptoms such as a sudden headache, difficulty walking, or numbness or paralysis on one side of the face or the body.

Multiple small strokes or other conditions that affect blood vessels and nerve fibers deep inside the brain may cause more gradual thinking changes as damage accumulates. Common early signs of widespread small vessel disease include impaired planning and judgment; uncontrolled laughing and crying; declining ability to pay attention; impaired function in social situations; and difficulty finding the right words.

The present subject matter provides diagnostic, prognostic, treatment, and monitoring methods, as well as related compositions, kits, and systems, for each subtype, symptom, and/or complication of cerebral SVD.

HTRA1-Associated Small Vessel Disease

As used herein, an "HTRA1-associated small vessel disease" or HTRA1-associated SVD is a SVD that results from a dominant HTRA1 mutation. In various embodiments, a subject is heterozygous for the mutation. Descriptions of exemplary heterozygous mutations of the HTRA1 gene in patients with familial cerebral small vessel disease are included in Donato et al. 2017 "Heterozygous mutations of HTRA1 gene in patients with familial cerebral small vessel disease" *CNS Neurosci Ther.* 23(9):759-765; and Verdura et al. (2015) "Heterozygous HTRA1 mutations are associated with autosomal dominant cerebral small vessel disease" *Brain* 138; 2347-2358, the entire contents of each of which are incorporated herein by reference.

Cerebral Autosomal Recessive Arteriopathy with Subcortical Infarcts and Leukoencephalopathy Cerebral autosomal recessive arteriopathy with subcortical infarcts and leukoencephalopathy, commonly known as CARASIL, is an inherited condition that causes stroke and other impairments. As its name suggests, this condition is inherited in an autosomal recessive pattern. Autosomal recessive inheritance means both copies of the gene in each cell have mutations. The parents of an individual with an autosomal recessive condition each carry one copy of the mutated gene, but they typically do not show signs and symptoms of the condition. See, e.g., the U.S. National Library of Medicine Genetics Home Reference, CARASIL, available at ghr.nlm.nih.gov/condition/cerebral-autosomal-recessive-arteriopathy-with-subcortical-infarcts-and-leukoencephalopathy#inheritance, the entire contents of which are incorporated herein by reference.

Abnormalities affecting the brain and other parts of the nervous system become apparent in an affected person's twenties or thirties. Often, muscle stiffness (spasticity) in the legs and problems with walking are the first signs of the disorder. About half of affected individuals have a stroke or similar episode before age 40. As the disease progresses, most people with CARASIL also develop mood and personality changes, a decline in thinking ability (dementia), memory loss, and worsening problems with movement.

Other characteristic features of CARASIL include premature hair loss (alopecia) and attacks of low back pain. The hair loss often begins during adolescence and is limited to the scalp. Back pain, which develops in early to mid-adulthood, results from the breakdown (degeneration) of the discs that separate the bones of the spine (vertebrae) from one another.

The signs and symptoms of CARASIL worsen slowly with time. Over the course of several years, affected individuals become less able to control their emotions and communicate with others. They increasingly require help with personal care and other activities of daily living; after a few years, they become unable to care for themselves. Most affected individuals die within a decade after signs and symptoms first appear, although few people with the disease have survived for 20 to 30 years.

CARASIL is caused by mutations in the HTRA1 gene. This gene provides instructions for making an enzyme that is found in many of the body's organs and tissues. One of the major functions of the HTRA1 enzyme is to regulate signaling by proteins in the transforming growth factor-beta (TGF-β) family. TGF-β signaling is essential for many critical cell functions. It also plays an important role in the formation of new blood vessels (angiogenesis).

Without wishing to be bound by any scientific theory, in people with CARASIL, mutations in the HTRA1 gene prevent the effective regulation of TGF-β signaling. HTRA1 mutations leading to SVD have been associated with loss of function of the gene. Abnormally regulated TGF-β signaling may alter the structure of small blood vessels, particularly in the brain. These blood vessel abnormalities (described as arteriopathy) greatly increase the risk of stroke and lead to the death of nerve cells (neurons) in many areas of the brain. Dysregulation of TGF-β signaling may also underlie the hair loss and back pain seen in people with CARASIL, although the relationship between abnormal TGF-β signaling and these features is less clear.

Lacunar Strokes and Hemorrhagic Strokes

As disclosed herein, the consequences of SVD on the brain parenchyma include lesions located in the subcortical structures such as lacunar infarcts (also termed "lacunar strokes"), white matter lesions, large hemorrhages, and microbleeds. Strokes, such as lacunar strokes and hemorrhagic strokes, are signs of (e.g., may result from) a SVD. A lacunar stroke is the most common type of stroke, and results from the occlusion of one or more small penetrating arteries that provide blood to the brain's deep structures. In some embodiments, a lacunar stroke comprises a small infarct (e.g., 2-20 mm in diameter) in the deep cerebral white matter, basal ganglia, or pons. Such events can result from the occlusion of a single small perforating artery supplying the subcortical areas of the brain. Hemorrhagic strokes (bleeds) can result from a weakened vessel that ruptures and bleeds into the surrounding brain tissue.

In some cases, a subject with a SVD has more difficulty recovering from a lacunar stroke compared to, e.g., a subject without a SVD. A subject with a SVD may also have more difficulty recovering from a hemorrhagic stroke. Treatment, as described herein, improves (e.g., the rate or degree of) recovery, e.g., alleviation of symptoms, of a subject with a SVD who has had a lacunar stroke or a hemorrhagic stroke. Such a treatment also reduces the likelihood that a subject who has a SVD will have a lacunar stroke or a hemorrhagic stroke.

The present subject matter provides methods for the treatment of each subtype, symptom, and/or complication of lacunar strokes and hemorrhagic strokes.

It was reported that heterozygous individuals carrying only one copy of the mutant HTRA1 also develop cerebral small vessel disease indicating that HTRA1 is a haploinsufficient gene and that the disease may also be inherited following an autosomal dominant pattern. Heterozygous HTRA1 mutations are associated with autosomal dominant cerebral small vessel disease. See, e.g., Verdura et al. (2015) Brain 138(Pt 8):2347-58.

Various embodiments of the present subject matter relate to the detection of increased levels of HTRA1 (e.g., a HTRA1 protein having an amino acid sequence encoded by either a mutated or wild-type HTRA1 gene) in a biological sample from a subject. It is surprising that an increase in the level of a HTRA1 protein can indicate an increased risk for CADASIL or a symptom or complication thereof, which as discussed below, is a dominant disease caused by NOTCH3.

Surprisingly, an increase in HTRA1 is indicative of (and identifies a subject as having or being at risk of) CADASIL whereas a decrease in HTRA1 levels or HTRA1 activity is indicative of (and identifies a subject as having or being at risk of) CARASIL.

The present subject matter provides diagnostic, prognostic, treatment, and monitoring methods, as well as related compositions, kits, and systems, for each subtype, symptom, and/or complication of CARASIL.

Cerebral Autosomal-Dominant Arteriopathy with Subcortical Infarcts and Leukoencephalopathy Cerebral autosomal dominant arteriopathy with subcortical infarcts and leukoencephalopathy, usually called CADASIL, is an inherited condition that causes stroke and other impairments. This condition affects blood flow in small blood vessels, particularly cerebral vessels within the brain. The muscle cells surrounding these blood vessels (vascular smooth muscle cells) are abnormal and gradually die. In the brain, the resulting blood vessel damage (arteriopathy) can cause migraines, often with visual sensations or auras, or recurrent seizures (epilepsy). See, e.g., the U.S. National Library of Medicine Genetics Home Reference, CADASIL, available at ghr.nlm.nih.gov/condition/cerebral-autosomal-dominant-arteriopathy-with-subcortical-infarcts-and-leukoencephalopathy#genes, the entire contents of which are incorporated herein by reference.

Damaged blood vessels reduce blood flow and can cause areas of tissue death (infarcts) throughout the body. An infarct in the brain can lead to a stroke. In individuals with CADASIL, a stroke can occur at any time from childhood to late adulthood, but typically happens during mid-adulthood. People with CADASIL often have more than one stroke in their lifetime. Recurrent strokes can damage the brain over time. Strokes that occur in the subcortical region of the brain, which is involved in reasoning and memory, can cause progressive loss of intellectual function (dementia) and changes in mood and personality.

Many people with CADASIL also develop leukoencephalopathy, which is a change in a type of brain tissue called white matter that can be seen with magnetic resonance imaging (MRI).

The age at which the signs and symptoms of CADASIL first begin varies greatly among affected individuals, as does the severity of these features.

CADASIL is not associated with the common risk factors for stroke and heart attack, such as high blood pressure and high cholesterol, although some affected individuals might also have these health problems. However, NOTCH3 variants may influence risk of developing Alzheimer's Disease (Sassi, C. et al. *Neurobiology of Aging* Mendelian adult-onset leukodystrophy genes in Alzheimer's disease: critical influence of CSF1R and NOTCH3 online Feb. 2, 2018; 1.e1-1.e13, hereby incorporated by reference).

Mutations in the NOTCH3 gene cause CADASIL. One copy of the altered NOTCH3 gene in each cell is sufficient to cause the disorder. The NOTCH3 gene provides instructions for producing the NOTCH3 receptor protein, which is important for the normal function and survival of vascular smooth muscle cells. When certain molecules attach (bind) to NOTCH3 receptors, the receptors send signals to the nucleus of the cell. These signals then turn on (activate) particular genes within vascular smooth muscle cells.

NOTCH3 gene mutations lead to the production of an abnormal NOTCH3 receptor protein that impairs the function and survival of vascular smooth muscle cells. Disruption of NOTCH3 functioning can lead to the self-destruction (apoptosis) of these cells. In the brain, the loss of vascular smooth muscle cells, and/or mural cells (progenitors of vascular smooth muscle cells and pericytes), results in blood vessel damage that can cause the signs and symptoms of CADASIL.

Various embodiments of the present subject matter relate to the detection of decreased levels of the NOTCH3 extracellular domain (e.g., an extracellular domain having an amino acid sequence of a NOTCH3 extracellular domain encoded by either a mutated or wild-type NOTCH3 gene) in a biological sample from a subject. It is surprising that a decrease in the level of a NOTCH3 extracellular domain can indicate an increased risk for CADASIL or a symptom or complication thereof.

Figure 5A:
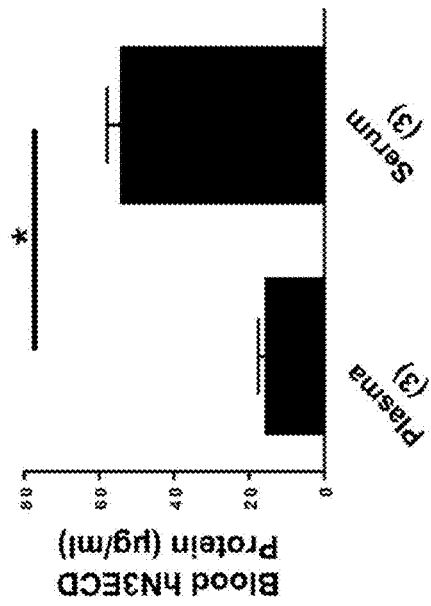
FIGS. 5A-D are graphs showing the detection of circulating human N3ECD using a custom ELISA.
Figure 5C:
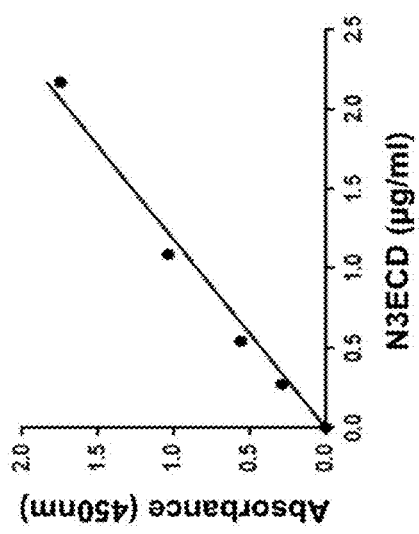
Figure 5B:
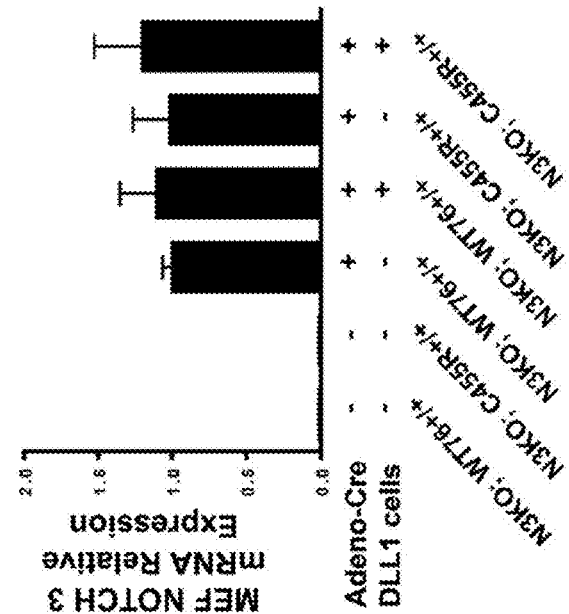
Figure 5D:
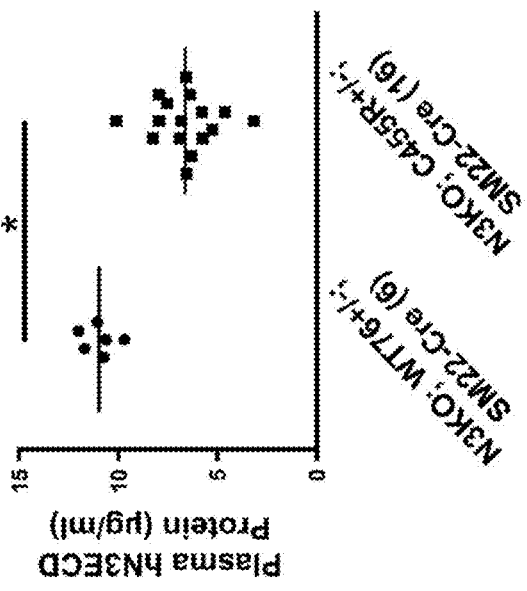

FIG. 5C shows that the levels of N3ECD are significantly reduced in mice carrying the C455R CADASIL mutation in NOTCH3 compared to controls. FIG. 5D shows that this was not explained by differences in the levels of mRNA expression. This mutation has been shown to abrogate NOTCH3 signaling in vivo and in vitro in a previous publication (Arboleda-Velasquez et al., PNAS, 2011). The decreased levels of N3ECD may be related to impaired NOTCH3 signaling as it is known that upon proteolytic cleavage of the NOTCH receptors the NOTCH ectodomain is released from the receptor expressing cell and transendocytosed into the ligand-expressing cell (Klueg and Muskavitch, 1999), a process that may be impaired by deficient signaling.

No specific treatment is available for CADASIL. However, anti-platelet agents such as aspirin, dipyridamole, ticlopidine, and clopidogrel are used to slow down the disease and help prevent strokes. Aspects of the present invention relate to administering an anti-platelet agent to a subject who is diagnosed with or determined to be at risk of developing CADASIL. In some embodiments, the subject receives therapy for primary or secondary prevention of stroke and myocardial infarction. Risk-reduction measures in primary stroke prevention may include the use of antihypertensive medications; platelet antiaggregants; 3-hydroxy-3-methylglutaryl coenzyme A (HMG-CoA) reductase inhibitors (statins); smoking cessation; dietary intervention; weight loss; and exercise. Additionally, and as noted elsewhere herein, a decrease in the level of NOTCH3 is indicative of CADASIL, and subjects with CADASIL should not be administered thrombolytic agents. In various embodiments, a subject is not administered an anticoagulant therapy or a thrombolytic agent if a decreased level of NOTCH3 is detected in the subject. Secondary prevention may include the use of antiaggregants (aspirin, clopidogrel, extended-release dipyridamole, ticlopidine), cholesterol-reducing medications, and/or blood pressure-lowering medications, as well as the cessation of cigarette smoking, improving the diet (e.g., reducing red meat consumption and/or increasing vegetable consumption), and increased exercise. In certain embodiments relating to women who have been taking an oral contraceptive and is diagnosed as having CADASIL or at risk of developing CADASIL is advised or directed to stop taking the oral contraceptive. In various embodiments, a subject diagnosed with CADASIL or identified as having a risk for developing CADASIL is administered treatment for hypercholesterolemia and/or hypertension. In some embodiments, the subject is administered folic acid and/or L-Arginine. Moreover, the efficacy of a therapeutic agent or regimen may be assessed based on its ability to increase the level of NOTCH3 in a subject with CADASIL (with the increase being indicative of efficacy). Thus, methods, compositions, kits, and devices provided herein are useful for evaluating the efficacy of both known and experimental treatments for the primary, secondary, or tertiary prevention or treatment of the disease.

The present subject matter provides diagnostic, prognostic, treatment, and monitoring methods, as well as related compositions, kits, and systems, for each subtype, symptom, and/or complication of CADASIL.

NOTCH3 Loss of Function-Associated Small Vessel Disease

NOTCH3 loss of function mutations cause an SVD phenotype strikingly similar to CADASIL but with key differences including the lack of accumulation of the NOTCH3 extracellular domain and the lack of GOM deposits. Typical mutations include changes leading to NOTCH3 frame shifts, premature stop codons, or splicing defects. Partial or complete gene deletions or promoter or enhancer mutations leading to lower than normal NOTCH3 expression are also included. It has been reported that in some patients, typical CADASIL mutations also lead to NOTCH3 loss of function and in these, NOTCH3 loss of function contributes to SVD pathology. In most cases, patients with NOTCH3 loss of function are heterozygotes although a homozygote patient has been reported with earlier age at onset of SVD. This indicates that NOTCH3 is haploinsufficient in humans because one wild-type copy of the gene is not sufficient to produce a wild type phenotype. Conditions that may indirectly lead to a decrease in NOTCH3 expression or function in the absence of mutations including cardiovascular or metabolic disease or aging or disease or environmental factor are also included.

Age-Related Macular Degeneration

Age-related macular degeneration (AMD) is an eye disease that is a leading cause of vision loss in older people in developed countries. The vision loss usually becomes noticeable in a person's sixties or seventies and tends to worsen over time. See, e.g., the U.S. National Library of Medicine Genetics Home Reference, Age-Related Macular Degeneration, available at ghr.nlm.nih.gov/condition/age-related-macular-degeneration, the entire contents of which are incorporated herein by reference.

AMD mainly affects central vision, which is needed for detailed tasks such as reading, driving, and recognizing faces. The vision loss in this condition results from a gradual deterioration of light-sensing cells in the tissue at the back of the eye that detects light and color (the retina). Specifically, age-related macular degeneration affects a small area near the center of the retina, called the macula, which is responsible for central vision. Side (peripheral) vision and night vision are generally not affected.

There are two major types of AMD, known as the dry form and the wet form. The dry form is much more common, accounting for 85 to 90 percent of all cases of age-related macular degeneration. It is characterized by a buildup of yellowish deposits called drusen beneath the retina and slowly progressive vision loss. The condition typically affects vision in both eyes, although vision loss often occurs in one eye before the other.

The wet form of AMD is associated with severe vision loss that can worsen rapidly. This form of the condition is characterized by the growth of abnormal, fragile blood vessels underneath the macula. These vessels leak blood and fluid, which damages the macula and makes central vision appear blurry and distorted.

AMD results from a combination of genetic and environmental factors. Many of these factors have been identified, but some remain unknown.

Without wishing to be bound by any scientific theory, changes in many genes may be risk factors for age-related macular degeneration. The best-studied of these genes are involved in a part of the body's immune response known as the complement system. This system is a group of proteins that work together to destroy foreign invaders (such as bacteria and viruses), trigger inflammation, and remove debris from cells and tissues. Genetic changes in and around several complement system genes, including the complement factor H (CFH) gene, contribute to a person's risk of developing age-related macular degeneration. It is unclear how these genetic changes are related to the retinal damage and vision loss characteristic of this condition. Changes on the long (q) arm of chromosome 10 in a region known as 10q26 are also associated with an increased risk of age-related macular degeneration. The 10q26 region contains two genes of interest, age-related maculopathy susceptibility 2 (ARMS2) and HTRA1. Changes in both genes have been studied as possible risk factors for the disease. However, because the two genes are so close together, it is difficult to tell which gene is associated with age-related macular degeneration risk, or whether increased risk results from variations in both genes. An estimated 15 to 20 percent of people with age-related macular degeneration have at least one first-degree relative (such as a sibling) with the condition. Other genes that are associated with age-related macular degeneration include genes involved in transporting and processing high-density lipoprotein (HDL) and genes that have been associated with other forms of macular disease.

Nongenetic factors that contribute to the risk of age-related macular degeneration are also known. Age appears to be the most important risk factor; the chance of developing the condition increases significantly as a person gets older. Smoking is another established risk factor for age-related macular degeneration.

Aspects of the present subject matter relate to administering a treatment for AMD to a subject who is diagnosed with or determined to be at risk of developing AMD. In some embodiments, the subject is administered a statin. In some embodiments relating to neovascular AMD, the subject is administered an antiangiogenic steroid such as anecortave acetate or triamcinolone acetonide. In various embodiments relating to wet AMD, the subject can be treated with laser coagulation or a medication that stops and sometimes reverses the growth of blood vessels. In certain embodiments, the subject is treated with bevacizumab, ranibizumab, pegaptanib, or aflibercept. In some embodiments, photodynamic therapy is administered to the subject. For example, the drug verteporfin is administered intravenously and light of a certain wavelength (e.g., 689 nm) is then applied to the abnormal blood vessels, which activates the verteporfin to destroy the vessels.

The present subject matter provides diagnostic, prognostic, treatment, and monitoring methods, as well as related compositions, kits, and systems, for each subtype, symptom, and/or complication of AMD.

Retinopathy

Retinopathy is persistent or acute damage to the retina of the eye. Ongoing inflammation and vascular remodeling may occur over periods of time where the patient is not fully aware of the extent of the disease. Frequently, retinopathy is an ocular manifestation of systemic disease as seen in diabetes or hypertension. Diabetic retinopathy is the leading cause of blindness in working-aged people.

Causes of retinopathy include but are not limited to: (i) diabetes mellitus, which can cause diabetic retinopathy; (ii) arterial hypertension, which can cause hypertensive retinopathy; (iii) retinopathy of prematurity due to prematurity of a newborn (under the 9 months of human pregnancy); (iv) radiation retinopathy due to exposure to ionizing radiation; (v) solar retinopathy due to direct sunlight exposure; (vi) sickle cell disease; (vii) retinal vascular disease such as retinal vein or artery occlusion; (viii) trauma, especially to the head, and several diseases may cause Purtscher's retinopathy; and (ix) hyperviscosity-related retinopathy as seen in disorders which cause paraproteinemia.

Many types of retinopathy are proliferative, most often resulting from neovascularization or blood vessel overgrowth. Angiogenesis is the hallmark precursor that may result in blindness or severe vision loss, particularly if the macula becomes affected. Retinopathy may also be a symptom or complication of a ciliopathic genetic disorder such as Alström syndrome or Bardet-Biedl syndrome.

Aspects of the present subject matter relate to administering a treatment for retinopathy to a subject who is diagnosed with or determined to be at risk of developing retinopathy. Treatment may include laser therapy to the retina and/or the administration of a vascular endothelial growth factor (VEGF) inhibitor.

The present subject matter provides diagnostic, prognostic, treatment, and monitoring methods, as well as related compositions, kits, and systems, for each subtype, symptom, and/or complication of retinopathy.

Microangiopathy

Microangiopathy (or microvascular disease, or small vessel disease) is an angiopathy (i.e. disease of blood vessels) affecting small blood vessels in the body. The condition can occur in any organ of the body. One cause of microangiopathy is long-term diabetes mellitus. In this case, high blood glucose levels cause the endothelial cells lining the blood vessels to take in more glucose than normal (these cells do not depend on insulin). They then form more glycoproteins on their surface than normal, and also cause the basement membrane in the vessel wall to grow abnormally thicker and weaker. Therefore they bleed, leak protein, and slow the flow of blood through the body. As a result, some organs and tissues do not get enough blood (carrying oxygen and nutrients) and are damaged, for example, the retina (diabetic retinopathy) or kidney (diabetic nephropathy). Nerves and neurons, if not sufficiently supplied with blood, are also damaged, which leads to loss of function (diabetic neuropathy, especially peripheral neuropathy). Microangiopathy may also lead to damage or loss of function of vascular smooth muscle cells or and/or mural cells (progenitors of smooth muscle cells and pericytes).

Massive microangiopathy may cause microangiopathic hemolytic anemia (MAHA).

The present subject matter provides diagnostic, prognostic, treatment, and monitoring methods, as well as related compositions, kits, and systems, for each subtype, symptom, and/or complication of microangiopathy.

Nephropathy and Small Vessel Diseases of the Kidney

SVD can occur in the kidneys during or as part of nephropathy. For example, diabetic nephropathy (or diabetic kidney disease) is a progressive kidney disease caused by damage to the capillaries in the kidneys' glomeruli. It is characterized by nephrotic syndrome and diffuse scarring of the glomeruli. It is due to longstanding diabetes mellitus, and is a prime reason for dialysis in many developed countries. It is classified as a small blood vessel complication of diabetes. During its early course, diabetic nephropathy often has no symptoms. Symptoms can take 5 to 10 years to appear after the kidney damage begins. These late symptoms include severe tiredness, headaches, a general feeling of illness, nausea, vomiting, frequent voiding, lack of appetite, itchy skin, and leg swelling.

The present subject matter provides diagnostic, prognostic, treatment, and monitoring methods, as well as related compositions, kits, and systems, for each subtype, symptom, and/or complication of nephropathy.

Proximal 19p13.12 Microdeletion Syndrome

In embodiments, the SVD comprises proximal 19p13.12 microdeletion syndrome. Non-limiting descriptions relating to this syndrome are provided in Huynh et al. (2018) "First prenatal case of proximal 19p13.12 microdeletion syndrome: New insights and new delineation of the syndrome" *Eur J Med Genet*. S1769-7212(17)30466-4, the entire content of which is incorporated herein by reference.

In certain embodiments, proximal 19p13.12 microdeletion syndrome comprises intellectual disability, facial dysmorphism, and/or branchial arch defects. In some embodiments, proximal 19p13.12 microdeletion syndrome comprises hypertrichosis-synophrys-protruding front teeth. In various embodiments, a subject with proximal 19p13.12 microdeletion syndrome comprises a heterozygous interstitial deletion at 19p13.12 chromosome region. In certain embodiments, the deletion is a deletion of about 350 kb to about 750 kb. In some embodiments, the deletion is a deletion of about 745 kb. In various embodiments, the deletion includes at least a portion of the NOTCH3 gene. In certain embodiments, the deletion includes the entire NOTCH3 gene. In some embodiments, the deletion comprises (e.g., in addition to a mutation in part of all of the NOTCH3 gene) a portion of, or the entirety of any one of, any combination of the following genes: SYDE1, AKAP8, AKAP8L, WIZ and BRD4.

The present subject matter provides methods for the treatment of each subtype, symptom, and/or complication of proximal 19p13.12 microdeletion syndrome.

Myocardial Ischemia

NOTCH3 deficiency impairs coronary microvascular maturation and reduces cardiac recovery after myocardial ischemia. See, e.g., Tao et al. (2017) "Notch3 deficiency impairs coronary microvascular maturation and reduces cardiac recovery after myocardial ischemia" *Int J Cardiol*. 2017 Jun. 1; 236:413-422, the entire content of which is incorporated herein by reference. In various embodiments, a subject with myocardial ischemia has myocardial infarction.

In certain embodiments, reduced NOTCH3 results in a reduction of pericytes and small arterioles. In some embodiments, the reduction in pericytes and small arterioles increases the severity of myocardial ischemia, and/or reduces cardiac recovery after myocardial ischemia. In various embodiments, a subject with reduced NOTCH3 function (e.g., due to a mutation) is prone to ischemic injury with larger infarcted size and higher rates of mortality. In certain embodiments, the expression of CXCR-4 and VEGF/Ang-1 is decreased in a subject with reduced NOTCH3 function. In some embodiments, a subject with reduced NOTCH3 function has fewer NG2+/Sca1+ and NG2+/c-kit+ progenitor cells in an ischemic area and exhibits worse cardiac function recovery at 2 weeks after myocardial ischemia compared to a corresponding subject with a normal level of NOTCH3 function. In certain embodiments, a subject with reduced NOTCH3 function has a significant reduction of pericyte/capillary coverage and arteriolar maturation compared to a corresponding subject with a normal level of NOTCH3 function. In various embodiments, a subject with a reduced level of NOTCH3 function and who has had myocardial ischemia has increased intracellular adhesion molecule-2 (ICAM-2) expression and CD11b+ macrophage infiltration into ischemic areas compared to that of a corresponding subject with a normal level of NOTCH3 function. In embodiments, a subject has a NOTCH3 mutation that impairs recovery of cardiac function post-myocardial ischemia by the mechanisms involving the pre-existing coronary microvascular dysfunction conditions, and impairment of pericyte/progenitor cell recruitment and microvascular maturation.

The present subject matter provides methods for the treatment of each subtype, symptom, and/or complication of myocardial ischemia.

Heart Failure

Heart failure is a chronic, progressive condition in which the heart muscle is unable to pump enough blood through to meet the body's needs for blood and oxygen. Loss of NOTCH3 signaling in vascular smooth muscle cells promotes severe heart failure upon hypertension. See, e.g., Ragot et al., (2016) Hypertension. 68(2):392-400; and the American Heart Association, What is Heart Failure? available at www.heartorg/HEARTORG/Conditions/HeartFailure/AboutHeartFailure/About-Heart-Failure_UCM_002044_Article.jsp#.WM16W_7lva8, the entire contents of each of which are incorporated herein by reference.

The heart tries to make up for this by enlarging, developing more muscle mass, and/or pumping faster. When the heart chamber enlarges, it stretches more and can contract more strongly, so it pumps more blood. With an enlarged heart, the body starts to retain fluid, the lungs get congested with fluid and the heart begins to beat irregularly. An increase in muscle mass occurs because the contracting cells of the heart get bigger. This lets the heart pump more strongly, at least initially. Increased heartrate helps to increase the heart's output.

The body also tries to compensate in other ways: (i) The blood vessels narrow to keep blood pressure up, trying to make up for the heart's loss of power; and (ii) The body diverts blood away from less important tissues and organs (like the kidneys), the heart and brain.

These temporary measures mask the problem of heart failure, but they do not solve it. Heart failure continues and worsens until these substitute processes no longer work.

Eventually the subject experiences the fatigue, breathing problems or other symptoms that usually prompt a trip to the doctor.

Heart failure can involve the heart's left side, right side or both sides. However, it usually affects the left side first.

The present subject matter provides diagnostic, prognostic, treatment, and monitoring methods, as well as related compositions, kits, and systems, for each subtype, symptom, and/or complication of heart failure.

Alagille Syndrome and Familial Tetralogy of Fallot

Alagille syndrome is a genetic disorder that can affect the liver, heart, and other parts of the body. See, e.g., the U.S. National Library of Medicine Genetics Home Reference, Alagille syndrome, available at ghr.nlm.nih.gov/condition/alagille-syndrome, the entire contents of which are incorporated herein by reference.

One of the major features of Alagille syndrome is liver damage caused by abnormalities in the bile ducts. These ducts carry bile (which helps to digest fats) from the liver to the gallbladder and small intestine. In Alagille syndrome, the bile ducts may be narrow, malformed, and reduced in number (bile duct paucity). As a result, bile builds up in the liver and causes scarring that prevents the liver from working properly to eliminate wastes from the bloodstream. Signs and symptoms arising from liver damage in Alagille syndrome may include a yellowish tinge in the skin and the whites of the eyes (jaundice), itchy skin, and deposits of cholesterol in the skin (xanthomas).

Alagille syndrome is also associated with several heart problems, including impaired blood flow from the heart into the lungs (pulmonic stenosis). Pulmonic stenosis may occur along with a hole between the two lower chambers of the heart (ventricular septal defect) and other heart abnormalities. This combination of heart defects is called tetralogy of Fallot.

People with Alagille syndrome may have distinctive facial features including a broad, prominent forehead; deep-set eyes; and a small, pointed chin. The disorder may also affect the blood vessels within the brain and spinal cord (central nervous system) and the kidneys. Affected individuals may have an unusual butterfly shape of the bones of the spinal column (vertebrae) that can be seen in an x-ray.

Problems associated with Alagille syndrome generally become evident in infancy or early childhood. The severity of the disorder varies among affected individuals, even within the same family. Symptoms range from so mild as to go unnoticed to severe heart and/or liver disease requiring transplantation.

Some people with Alagille syndrome may have isolated signs of the disorder, such as a heart defect like tetralogy of Fallot, or a characteristic facial appearance. These individuals do not have liver disease or other features typical of the disorder.

In more than 90 percent of cases, mutations in the JAGGED" gene cause Alagille syndrome. Another 7 percent of individuals with Alagille syndrome have small deletions of genetic material on chromosome 20 that include the JAG1 gene, which encodes JAGGED'. A few people with Alagille syndrome have mutations in a different gene, called NOTCH2. The JAG1 and NOTCH2 genes provide instructions for making proteins that fit together to trigger interactions called NOTCH signaling between neighboring cells during embryonic development. This signaling influences how the cells are used to build body structures in the developing embryo. Changes in either the JAG1 gene or NOTCH2 gene probably disrupt the NOTCH signaling pathway. As a result, errors may occur during development, especially affecting the bile ducts, heart, spinal column, and certain facial features.

The present subject matter provides diagnostic, prognostic, treatment, and monitoring methods, as well as related compositions, kits, and systems, for each subtype, symptom, and/or complication of Alagille syndrome and/or familial tetralogy of Fallot.

Patent Ductus Arteriosus

Patent ductus arteriosus (PDA) is a condition wherein the ductus arteriosus fails to close after birth. Early symptoms are uncommon, but in the first year of life include increased work of breathing and poor weight gain. An uncorrected PDA may lead to congestive heart failure with increasing age.

The ductus arteriosus is a fetal blood vessel that closes soon after birth. In a PDA, the vessel does not close and remains "patent" (open), resulting in irregular transmission of blood between the aorta and the pulmonary artery. PDA is common in newborns with persistent respiratory problems such as hypoxia, and has a high occurrence in premature newborns. Premature newborns are more likely to be hypoxic and have PDA due to underdevelopment of the heart and lungs.

A PDA allows a portion of the oxygenated blood from the left heart to flow back to the lungs by flowing from the aorta (which has higher pressure) to the pulmonary artery. If this shunt is substantial, the neonate becomes short of breath: the additional fluid returning to the lungs increases lung pressure, which in turn increases the energy required to inflate the lungs. This uses more calories than normal and often interferes with feeding in infancy. This condition, as a constellation of findings, is called congestive heart failure.

In some congenital heart defects (such as in transposition of the great vessels) a PDA may need to remain open, as it is the only way that oxygenated blood can mix with deoxygenated blood. In these cases, prostaglandins are used to keep the DA open until surgical correction of the heart defect is completed.

PDA is associated with NOTCH3 loss of function. See, e.g., Baeten et al., (2015) Genesis 53(12):738-48, the entire content of which is incorporated herein by reference.

The present subject matter provides diagnostic, prognostic, treatment, and monitoring methods, as well as related compositions, kits, and systems, for each subtype, symptom, and/or complication of PDA.

Cerebral Cavernous Malformations

Cerebral cavernous malformations are collections of small blood vessels (capillaries) in the brain that are enlarged and irregular in structure. These capillaries have abnormally thin walls, and they lack other support tissues, such as elastic fibers, which normally make them stretchy. See, e.g., the U.S. National Library of Medicine Genetics Home Reference, Cerebral Cavernous Malformation, available at ghr.nlm.nih.gov/condition/cerebral-cavernous-malformation, the entire contents of which are incorporated herein by reference. As a result, the blood vessels are prone to leakage, which can cause the health problems related to this condition. Cavernous malformations can occur anywhere in the body, but usually produce serious signs and symptoms only when they occur in the brain and spinal cord (which are described as cerebral).

Approximately 25 percent of individuals with cerebral cavernous malformations never experience any related health problems. Other people with this condition may experience serious signs and symptoms such as headaches, seizures, paralysis, hearing or vision loss, and bleeding in the brain (cerebral hemorrhage). Severe brain hemorrhages can result in death. The location and number of cerebral cavernous malformations determine the severity of this disorder. These malformations can change in size and number over time.

There are two forms of the condition: familial and sporadic. The familial form is passed from parent to child, and affected individuals typically have multiple cerebral cavernous malformations. The sporadic form occurs in people with no family history of the disorder. These individuals typically have only one malformation.

Defective NOTCH3 signaling is associated with cerebral cavernous malformations. See, e.g., Schultz et al. (2015) Stroke 46(5):1337-43, the entire content of which is incorporated herein by reference.

The present subject matter provides diagnostic, prognostic, treatment, and monitoring methods, as well as related compositions, kits, and systems, for each subtype, symptom, and/or complication of cerebral cavernous malformation.

Pulmonary Arterial Hypertension

Pulmonary arterial hypertension is a progressive disorder characterized by abnormally high blood pressure (hypertension) in the pulmonary artery, the blood vessel that carries blood from the heart to the lungs. See, e.g., the U.S. National Library of Medicine Genetics Home Reference, Pulmonary Arterial Hypertension, available at ghr.nlm.nih.gov/condition/pulmonary-arterial-hypertension, the entire contents of which are incorporated herein by reference. Pulmonary arterial hypertension is one form of a broader condition known as pulmonary hypertension. Pulmonary hypertension occurs when most of the very small arteries throughout the lungs narrow in diameter, which increases the resistance to blood flow through the lungs. To overcome the increased resistance, blood pressure increases in the pulmonary artery and in the right ventricle of the heart, which is the chamber that pumps blood into the pulmonary artery. Ultimately, the increased blood pressure can damage the right ventricle of the heart.

Signs and symptoms of pulmonary arterial hypertension occur when increased blood pressure cannot fully overcome the elevated resistance. As a result, the flow of oxygenated blood from the lungs to the rest of the body is insufficient. Shortness of breath (dyspnea) during exertion and fainting spells are the most common symptoms of pulmonary arterial hypertension. People with this disorder may experience additional symptoms, particularly as the condition worsens. Other symptoms include dizziness, swelling (edema) of the ankles or legs, chest pain, and a rapid heart rate.

The present subject matter provides diagnostic, prognostic, treatment, and monitoring methods, as well as related compositions, kits, and systems, for each subtype, symptom, and/or complication of pulmonary arterial hypertension.

Subjects at Risk of Developing a Small Vessel Disease or a Symptom or Complication of a Small Vessel Disease Aspects of the present subject matter relate to inhibiting or preventing a SVD (or a complication or symptom thereof) in a subject who is at risk of developing the SVD (or a symptom or complication thereof). In some embodiments, a subject at risk of developing an SVD or a symptom or complication thereof is administered a therapeutic treatment for the SVD prior to the subject's diagnosis or perception of the SVD or a symptom or complication of the SVD. In certain embodiments, a subject who has not been affirmatively diagnosed with a SVD or a symptom or complication thereof receives, or is advised or directed to receive, additional diagnostic testing or screening for the SVD based on the result of a diagnostic or prognostic method disclosed herein. In various embodiments, a subject is advised or directed to receive treatment for a SVD based on the result of a diagnostic or prognostic method disclosed herein.

Risk factors may vary from SVD to SVD. However, a subject may generally be considered to be at risk of suffering from a SVD or a symptom or complication thereof if the subject has at least 1 or 2 grandparents, parents, or siblings who suffers from the SVD or the symptom or complication thereof. Additional non-limiting examples of risk factors for SVDs are discussed below.

Cerebral SVD has frequently been found on computed tomography (CT) and magnetic resonance imaging (MRI) scans of elderly people. See, e.g., van Norden et al., (2011) BMC Neurology BMC series 11:29, the entire contents of which are incorporated herein by reference. In various embodiments, an elderly subject (e.g., a subject who is at least about 70, 75, 80, 85, 90, or 95 years old) is deemed to be at risk of and treated and/or screened for (e.g., using a diagnostic or prognostic method disclosed herein) cerebral SVD and/or a complication or symptom of cerebral SVD. Symptoms and complications of cerebral SVD are disclosed herein and include, e.g., vascular cognitive impairment, hemorrhages and microbleeds, neuropathy, strokes, dementia, and/or parkinsonism. In various embodiments, a subject at risk of developing cerebral SVD or a complication or symptom thereof is a subject who has suffered from at least one stroke. In certain embodiments, a subject is at risk of developing cerebral SVD or a complication or symptom thereof if the subject has hypertension (e.g., a systolic pressure of at least 140 mmHg or a diastolic pressure of at least 90 mmHg) and/or amyloid deposits in the walls of the blood vessels of the central nervous system. There are also hereditary risk factors for cerebral SVD. See, e.g., Plancher et al. Case Rep Neurol. 2015 May-August; 7(2): 142-147, the entire contents of which are incorporated herein by reference. In some embodiments, the subject has a mutated gene that is associated with cerebral SVD. In certain embodiments, a subject is at risk of developing cerebral SVD if the subject has at least 1 or 2 grandparents, parents, and/or sibling who suffers or has suffered from cerebral SVD or a complication or symptom thereof, and/or who has a gene mutation that is associated with cerebral SVD.

In some embodiments, the subject (or at least 1 or 2 grandparents, parents, and/or siblings thereof) has a mutation in a COL4A1 gene (which encodes the type IV collagen alpha-1 chain). COL4A1-related brain SVD is part of a group of conditions called the COL4A1-related disorders. See, e.g., the U.S. National Library of Medicine Genetics Home Reference, COL4A1-related brain small-vessel disease, available at ghr.nlm.nih.gov/condition/col4a1-related-brain-small-vessel-disease#genes, the entire contents of which are incorporated herein by reference. The conditions in this group have a range of signs and symptoms that involve fragile blood vessels. COL4A1-related brain small-vessel disease is characterized by weakening of the blood vessels in the brain. Stroke is often the first symptom of this condition, typically occurring in mid-adulthood. In affected individuals, stroke is usually caused by bleeding in the brain (hemorrhagic stroke) rather than a lack of blood flow in the brain (ischemic stroke), although either type can occur. Individuals with this condition are at increased risk of having more than one stroke in their lifetime. People with COL4A1-related brain small vessel disease also have leukoencephalopathy, which is a change in a type of brain tissue called white matter that can be seen with MRI. Affected individuals may also experience seizures and migraine headaches accompanied by visual sensations known as auras. In various embodiments, a subject with a COL4A1 mutation is at risk of and treated and/or screened for (e.g., using a diagnostic or prognostic method disclosed herein) for a symptom or complication such as a ischemic stroke, a hemorrhagic stroke, a migraine, a seizure, leukomalacia, nephropathy, hematuria, chronic muscle cramps, and/or a ocular anterior segment disease.

In some embodiments, a subject is at risk of cerebral SVD (e.g., sporadic cerebral SVD). In certain embodiments, the subject (or at least 1 grandparent, parent, aunt, uncle, cousin, and/or sibling thereof) has a mutation in a COL4A2 gene. COL4A2 is associated with lacunar ischemic stroke and deep intracerebral hemorrhage (ICH). See, e.g., Rannikmäe et al. (2017) "COL4A2 is associated with lacunar ischemic stroke and deep ICH: Meta-analyses among 21,500 cases and 40,600 controls" *Neurology* October 24; 89(17):1829-1839.

In embodiments, subjects at risk of ICH (e.g., deep or lobar ICH) and/or ischemic stroke (IS) (e.g., lacunar, cardioembolic, or large vessel disease) include subjects with a mutation in a COL4A1 or COL4A2 gene.

Subjects at risk of developing CARASIL or CADASIL and/or a symptom or complication thereof include subjects with at least 1 or 2 grandparents, parents, or siblings who suffer from CARASIL, or CADASIL, and/or the symptom or complication thereof. Subjects at risk of developing CARASIL also include subjects who carry a mutation in the HTRA1 gene, or who have a grandparent, parent, or sibling who carries such a mutation. Subjects at risk of developing CADASIL also include subjects who carry a mutation in the NOTCH3 gene, or who have a grandparent, parent, or sibling who carries such a mutation.

Subjects at risk of developing AMD (such as wet or dry AMD) and/or a symptom or complication thereof include subjects with high blood pressure, heart disease, a high-fat diet or one that is low in certain nutrients (such as antioxidants and zinc), obesity, repeated and/or prolonged exposure to ultraviolet (UV) rays from sunlight, or who smoke or have smoked for at least about 1, 5, 10, or more years. Subjects at risk of developing AMD and/or a symptom or complication thereof also include subjects with at least 1 or 2 grandparents, parents, or siblings who suffer from AMD, and/or the symptom or complication thereof. In various embodiments, a subject who carries a mutation in a CFH, ARMS2, HTRA1 gene, or a gene involved in transporting or processing HDL.

Subjects at risk of developing retinopathy include subjects with diabetes, arterial hypertension, sickle cell disease, a retinal vascular disease such as retinal vein or artery occlusion, Alström syndrome, or Bardet-Biedl syndrome. Subjects at risk of developing retinopathy also include premature human newborns (infants about 0, 1, 2, 3, 4, 5, 6, 7, 8, 9, 10 or more weeks old who were born after less than about 9, 8, or 7, months of pregnancy), subjects who have been exposed to ionizing radiation, and subjects whose retinas have been exposed to direct sunlight. In some embodiments, the retinopathy is diabetic retinopathy. Subjects at risk of developing diabetic retinopathy include, e.g., subjects with type 1 or type 2 diabetes. In various embodiments, the retinopathy is proliferative (e.g., proliferative diabetic retinopathy).

Subjects at risk of developing heart failure include subjects with high blood pressure, coronary artery disease, diabetes, sleep apnea, a congenital heart defect, valvular heart disease, or irregular heartbeats. Subjects at risk of heart failure also include alcoholics and former alcoholics, subjects who have used tobacco (e.g., who have smoked cigarettes for at least about 5, 10, 15, or 20 years), subjects who are obese, and subjects who have had a heart attack. Subjects who have taken rosiglitazone, pioglitazone, and nonsteroidal anti-inflammatory drugs (NSAIDs) [e.g., regularly (such as 1, 2, 3, 4, 5, 6, or 7 times per week) for at least about 1, 2, 3, 4, or 5 years] are also at risk for heart failure.

Subjects at risk of developing nephropathy (especially diabetic nephropathy) include subjects who have hyperglycemia, hypertension, at least 1 grandparent, parent, aunt, uncle, cousin, or sibling with nephropathy or hypertension. Additional non-limiting examples include subjects who smoke or have smoked for at least about 1, 5, 10, or more years.

Such subjects may be screened and/or treated using the methods, compositions, kits, and systems disclosed herein.

Antibodies for Biomarkers

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, an $F_{ab}$ expression library, single-chain antibody molecules (e.g., scFv), and multispecific antibodies formed from antibody fragments. By "specifically bind" or "immunoreacts with" is meant that the antibody reacts with one or more antigenic determinants of the desired antigen and does not react (i.e., bind) with other polypeptides or binds at much lower affinity ($K_d>10^{-6}$) with other polypeptides.

An "antibody fragment" refers to a molecule other than an intact antibody that comprises a portion of an intact antibody that binds the antigen to which the intact antibody binds.

The terms "full length antibody," "intact antibody," and "whole antibody" are used herein interchangeably to refer to an antibody having a structure substantially similar to a native antibody structure or having heavy chains that contain an Fc region.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ea., 2nd ed. Raven Press, N.Y. (1989)). The variable regions of each light/heavy chain pair form the antibody binding site.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs." Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three hypervariable regions (HVRs) of each variable domain interact to define an antigen binding site on the surface of the VH-VL dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

A "Fab" fragment contains a variable and constant domain of the light chain and a variable domain and the first constant domain (CHI) of the heavy chain. F(ab') 2 antibody fragments comprise a pair of Fab fragments which are generally covalently linked near their carboxy termini by hinge cysteines between them. Other chemical couplings of antibody fragments are also known in the art, "Single-chain Fv" or "scFv" antibody fragments comprise the VH and VL domains of an antibody, wherein these domains are present in a single polypeptide chain. Generally the Fv polypeptide further comprises a polypeptide linker between the VH and L domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-31S (1994).

The term "diabodies" refers to small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites. Diabodies are described more fully in, for example, BP 404,097; WO 93/11161; and Hollinger et al., Proc. Natl. Acad. Sci. USA, 90:6444-6448 (1993).

The expression "linear antibodies" refers to antibodies as described in Zapata et al., Protein Eng., 8 (10): 1057-1062 (1995). Briefly, these antibodies comprise a pair of tandem segments which, together with complementary light chain polypeptides, form a pair of antigen binding regions. Linear antibodies can be bispecific or monospecific.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

As used herein, the term "epitope" includes any protein determinant capable of specific binding to an antibody, an antibody fragment, or a T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM; preferably ≤100 nM and most preferably ≤10 nM.

Antibodies can be produced according to various methods known in the art.

Methods of preparing monoclonal antibodies are known in the art. For example, monoclonal antibodies may be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a full length protein or a fragment thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (see pp. 59-103 in Goding (1986) Monoclonal Antibodies: Principles and Practice Academic Press). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In some examples, the antibodies to an epitope for an interested protein as described herein or a fragment thereof are humanized antibodies. Humanized forms of non-human (e.g., murine) antibodies are chimeric molecules of immunoglobulins, immunoglobulin chains or fragments thereof (such as Fv, $F_{ab}$, $F_{ab'}$, $F_{(ab')2}$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al. 1986. Nature 321:522-525; Riechmann et al. 1988. Nature 332:323-329; Presta. 1992. Curr. Op. Struct. Biol. 2:593-596). Humanization can be essentially performed following methods of Winter and co-workers (see, e.g., Jones et al. 1986. Nature 321:522-525; Riechmann et al. 1988. Nature 332:323-327; and Verhoeyen et al. 1988. Science 239:1534-1536), by substituting rodent CDRs or CDR sequences for the corresponding sequences of a human antibody. Accordingly, such humanized antibodies are chimeric antibodies (e.g., U.S. Pat. No. 4,816,567), wherein substantially less than an intact human variable domain has been substituted by the corresponding sequence from a non-human species.

In various examples the antibodies to an epitope of an interested protein as described herein or a fragment thereof are human antibodies. Human antibodies can also be produced using various techniques known in the art, including phage display libraries (Hoogenboom and Winter. 1991. J. Mol. Biol. 227:381-388; Marks et al. 1991. J. Mol. Biol. 222:581-597) or the preparation of human monoclonal antibodies (e.g., Cole et al. 1985. Monoclonal Antibodies and Cancer Therapy Liss; Boerner et al. 1991. J. Immunol. 147(1):86-95). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in most respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al. 1992. Bio/Technology 10:779-783; Lonberg et al. 1994. Nature 368:856-859; Morrison. 1994. Nature 368: 812-13; Fishwild et al. 1996. Nature Biotechnology 14:845-51; Neuberger. 1996. Nature Biotechnology 14:826; Lonberg and Huszar. 1995. Intern. Rev. Immunol. 13:65-93. U.S. Pat. No. 6,719,971 also provides guidance to methods of generating humanized antibodies.

Exemplary antibodies against endostatin include, but are not limited to, antibodies obtained from Abcam (Cambridge, MA, USA) (e.g., Cat. Nos. ab64569, ab3453, ab202973, ab53702, ab175857, ab119279, ab15685, ab84250, ab114141, ab10604, ab11525, ab106491, ab109611, and ab53381), antibodies obtained from antibodies-online.com (Atlanta, GA, USA) (e.g., Cat. Nos. ABIN2871757, ABIN669951, ABIN108513, ABIN2192047, ABIN2878778, ABIN305768, and ABIN809524), and antibodies obtained from ThermoFisher Scientific (Cambridge, MA, USA) (e.g., Cat. Nos. PA1-601, MA1-40230, MA1-72504, PA1-30191, PAS-24199, and PAS-38894).

Exemplary antibodies against NOTCH3 include, but are not limited to, antibodies obtained from Abcam (Cambridge, MA, USA) (e.g., Cat. Nos. ab23426, ab95775, ab213632, ab192006, ab60087, and ab92758), antibodies obtained from antibodies-online.com (Atlanta, GA, USA) (e.g., Cat. Nos. ABIN2804742, ABIN358709, ABIN784287, ABIN562028, ABIN2663860, ABIN2657987, ABIN2658376, ABIN2663861, ABIN2665307, ABIN966685, and ABIN2665306), and antibodies obtained from ThermoFisher Scientific (Cambridge, MA, USA) (e.g., Cat. Nos. A16683, PAS-22797, PAS-19515, PAS-13203, PAS-28082, A18521, and PAS-47120).

Exemplary antibodies against HTRA1 include, but are not limited to, antibodies obtained from Abcam (Cambridge, MA, USA) (e.g., Cat. Nos. ab38611, ab113927, ab199529, and ab38610), antibodies obtained from antibodies-online.com (Atlanta, GA, USA) (e.g., Cat. Nos. ABIN388128, ABIN388127, ABIN356844, ABIN356843, ABIN970921, ABIN1873114, and ABIN1904101), and antibodies obtained from ThermoFisher Scientific (Cambridge, MA, USA) (e.g., Cat. Nos. PAS-23395, PAS-11413, and PA5-11412).

Exemplary antibodies against IGFBP-1 include, but are not limited to, antibodies obtained from ThermoFisher Scientific (Cambridge, MA, USA) (e.g., Cat. Nos. MA1-24775 and MA5-23727), antibodies obtained from Abcam (Cambridge, MA, USA) (e.g., Cat. Nos. ab10732 and ab181141), and antibodies obtained from R&D Systems (Minneapolis, MN, USA) (e.g., Cat. Nos. MAB675 and AF871).

Amplification-Based Detection Methods

RT-PCR is in particularly broad use as a method for amplifying mRNA sequences of interest. Details regarding the use of RT-PCR, PCR, and other amplification methods can be found in any of a variety of standard texts. One of skill will appreciate that essentially any RNA can be converted into DNA suitable for PCR expansion using a reverse transcriptase and a polymerase.

Prior to amplification and/or detection of a nucleic acid (e.g., an mRNA molecule encoding collagen18α1/endostatin, IGFBP-1, HTRA1, or NOTCH3), the nucleic acid is optionally purified from the a sample. Alternately, a sample can simply be directly subjected to amplification or detection, e.g., following aliquoting and/or dilution.

Suitable primers to be used with the invention can be designed using any suitable method. It is not intended that the invention be limited to any particular primer or primer pair. For example, primers can be designed using any suitable software program, such as LASERGENE®, e.g., taking account of publicly available sequence information. Sequences for mRNA transcripts of collagen18α1/endostatin, IGFBP-1, HTRA1, and/or NOTCH3 proteins are publicly available. Thus, suitable amplification primers can be constructed based on well understood base-pairing rules. The presence of any mRNA or amplicon thereof can be detected, e.g., by hybridization (e.g., array or probe hybridization), amplification (e.g., comprising RT-PCR), sequencing, and the like (as well as combinations of these or other approaches).

In various embodiments, a pair of primers that is complementary to a single transcript is used. In certain embodiments, one or more of the primers used comprises a sequence of nucleic acids that is not complementary to the transcript. For example, a primer may comprise a tag sequence that identifies the primer, and/or that may be used to identify the sample or amplicons derived from the sample after future processing (e.g. when multiple samples are analyzed using a single microarray). In some embodiments, the tag sequence is at least about 4, 5, 6, 7, 8, 9, or 10 nucleotides long and/or less than about 20, 15, 14, 13, 12, 11, 10, 9, 8, 7, 6, 5, or 4 nucleotides long.

In some embodiments, the primers are radiolabeled, or labelled by any suitable means (e.g., using a non-radioactive fluorescent tag), to allow for rapid visualization of differently sized amplicons following an amplification reaction without any additional labelling step or visualization step. In some embodiments, the primers are not labelled, and the amplicons are visualized following their size resolution, e.g., following agarose or acrylamide gel electrophoresis. In some embodiments, ethidium bromide staining of the PCR amplicons following size resolution allows visualization of the different size amplicons.

It is not intended that the primers be limited to generating an amplicon of any particular size. For example, the primers used to amplify the mRNA herein are not limited to amplifying the entire mRNA, or any subregion thereof. The primers can generate an amplicon of any suitable length for detection. In some embodiments, amplification produces an amplicon at least 20 nucleotides in length, or alternatively, at least 50 nucleotides in length, or alternatively, at least 100 nucleotides in length, or alternatively, at least 200 nucleotides in length. Amplicons of any size can be detected using various technologies described herein and known in the art. Differences in base composition or size can be detected by conventional methods such as electrophoresis.

In some embodiments, PCR detection using dual-labelled fluorogenic oligonucleotide probes, commonly referred to as "TaqMan™" probes is used. These probes are composed of short (e.g., 20-25 base) oligodeoxynucleotides that are labelled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TaqMan™ probes are oligonucleotides that have a label and a quencher, where the label is released during amplification by the exonuclease action of the polymerase used in amplification. This provides a real time measure of amplification during synthesis. A variety of TaqMan™ reagents are commercially available, e.g., from Applied Biosystems (Division Headquarters in Foster City, Calif.) as well as from a variety of specialty vendors such as Biosearch Technologies (e.g., black hole quencher probes). Further details regarding dual-label probe strategies can be found, e.g., in PCT International Patent Application Publication No. WO 92/02638.

Other similar methods include e.g. fluorescence resonance energy transfer between two adjacently hybridized probes, e.g., using the "LightCycler®" format described in U.S. Pat. No. 6,174,670, issued Jan. 16, 2001.

Array-Based Detection

Array-based detection can be performed using commercially available arrays, e.g., from Affymetrix (Santa Clara, Calif.) or other manufacturers. Reviews regarding the operation of nucleic acid arrays include Sapolsky et al., 1999 Genet Anal: Biomolec Engin 14: 187-192; Lockhart, 1998 Nature Medicine 4: 1235-1236; Fodor, 1997a FASEB Journal 11:A879; Fodor, 1997b Science 277: 393-395 and Chee et al., 1996 Science 274:610-614. Array based detection is one exemplary method for identification nucleotides (such as mRNA molecules or amplicons thereof) in samples, due to the inherently high-throughput nature of array based detection.

A variety of probe arrays have been described in the literature and can be used to detect mRNA or amplicons thereof (e.g., obtained using RT-PCR). For example, DNA probe array chips or larger DNA probe array wafers (from which individual chips would otherwise be obtained by breaking up the wafer) may be used. DNA probe array wafers may comprise, e.g., glass wafers on which high density arrays of DNA probes (short segments of DNA) have been placed. Each of these wafers can hold, for example, approximately 60 million DNA probes that are used to recognize longer sample DNA sequences (e.g., from individuals or populations). The recognition of a polynucleotide by the set of DNA probes on the glass wafer takes place through DNA hybridization. When a polynucleotide hybridizes with an array of DNA probes, the sample binds to those probes that are complementary to the polynucleotide sequence.

In some implementations, the polynucleotide to be analyzed (e.g., an mRNA encoding collagen18α1/endostatin, IGFBP-1, HTRA1, or NOTCH3) is isolated, amplified and labelled with biotin and/or a fluorescent reporter group. The labelled nucleic acid may then be incubated with the array using a fluidics station and hybridization oven. The array can be washed and or stained or counter-stained, as appropriate to the detection method. After hybridization, washing and staining, the array is inserted into a scanner, where patterns of hybridization are detected. The hybridization data are collected as light emitted from the fluorescent reporter groups already incorporated into the labelled nucleic acid, which is now bound to the probe array. Probes that most clearly match the labelled nucleic acid produce stronger signals than those that have mismatches. Since the sequence and position of each probe on the array are known, by complementarity, the identity of the nucleic acid sample applied to the probe array can be identified.

In one embodiment, two DNA samples may be differentially labelled and hybridized with a single set of the designed genotyping arrays. In this way two sets of data can be obtained from the same physical arrays. Labels that can be used include, but are not limited to, cychrome, fluorescein, or biotin (later stained with phycoerythrin-streptavidin after hybridization). Two-color labelling is described in U.S. Pat. No. 6,342,355, issued Jan. 29, 2002. Each array may be scanned such that the signal from both labels is detected simultaneously, or may be scanned twice to detect each signal separately.

In various embodiments, intensity data is collected by the scanner for all the markers for each of the individuals that are tested for presence or level of the marker. The measured intensities are a measure indicative of the amount of a particular marker present in the sample for a given individual (i.e., the expression level).

In some embodiments, the level of mRNA is measured by RNA sequencing. In various embodiments, the level of a protein is measured by mass spectrometry (MS). In certain embodiments, the protein is measures by gas chromatography-mass spectrometry (GC-MS), liquid chromatography-mass spectrometry (LC-MS), MALDI-TOF (which combines a matrix-assisted laser desorption/ionization source with a time-of-flight mas analyzer).

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "subject," "patient," "individual," and the like as used herein are not intended to be limiting and can be generally interchanged. An individual described as a "subject," "patient," "individual," and the like does not necessarily have a given disease, but may be merely seeking medical advice. The terms "subject," "patient," "individual," and the like as used herein include all members of the animal kingdom that may suffer from the indicated disorder. In some aspects, the subject is a mammal, and in some aspects, the subject is a human.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "treating" encompasses, e.g., inhibition, regression, or stasis of the progression of a disorder. For purposes of this disclosure, beneficial or desired clinical results include, but are not limited to, alleviation or amelioration of any symptom or symptoms, diminishment of extent of disease, stabilized (i.e., not worsening) state of disease, preventing spread of disease, delay or slowing of disease progression, amelioration or palliation of the disease state, and recovery (whether partial or total), whether detectable or undetectable. As used herein, "inhibition" of disease progression or a disease complication in a subject means preventing or reducing the disease progression and/or disease complication in the subject.

As used herein, a "symptom" associated with a disorder includes any clinical or laboratory manifestation associated with the disorder, and is not limited to what the subject can feel or observe.

As used herein, "effective" when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

As used herein, "pharmaceutically acceptable" carrier or excipient refers to a carrier or excipient that is suitable for use with humans and/or animals without undue adverse side effects (such as toxicity, irritation, and allergic response)

commensurate with a reasonable benefit/risk ratio. It can be, e.g., a pharmaceutically acceptable solvent, suspending agent or vehicle, for delivering the instant compounds to the subject.

A "control" sample or value refers to a sample that serves as a reference, usually a known reference, for comparison to a test sample. For example, a test sample can be taken from a test subject, e.g., a subject in need of diagnosis for a small vessel disease, and compared to samples from known conditions, e.g., a subject (or subjects) that does not have the small vessel disease (a negative or normal control), or a subject (or subjects) who does have the small vessel disease (positive control). A control can also represent an average value gathered from a number of tests or results. One of skill in the art will recognize that controls can be designed for assessment of any number of parameters. One of skill in the art will understand which controls are valuable in a given situation and be able to analyze data based on comparisons to control values. Controls are also valuable for determining the significance of data. For example, if values for a given parameter are variable in controls, variation in test samples will not be considered as significant.

The term "diagnosis" refers to a relative probability that a disease is present in the subject. Similarly, the term "prognosis" refers to a relative probability that a certain future outcome may occur in the subject. For example, in the context of the present disclosure, prognosis can refer to the likelihood that an individual will develop a disease, or the likely severity of the disease (e.g., severity of symptoms, rate of functional decline, survival, etc.). The terms are not intended to be absolute, as will be appreciated by any one of skill in the field of medical diagnostics.

The term, "normal amount" with respect to a compound (e.g., a protein or mRNA) refers to a normal amount of the compound in an individual who does not have a SVD or in a healthy or general population. The amount of a compound can be measured in a test sample and compared to the "normal control" level, utilizing techniques such as reference limits, discrimination limits, or risk defining thresholds to define cutoff points and abnormal values (e.g., for a particular SVD or a symptom thereof). The normal control level means the level of one or more compounds or combined compounds typically found in a subject known not suffering from an SVD. Such normal control levels and cutoff points may vary based on whether a compounds is used alone or in a formula combining with other compounds into an index. Alternatively, the normal control level can be a database of compounds patterns from previously tested subjects who did not develop a SVD or a particular symptom thereof (e.g., in the event the SVD develops or a subject already having the SVD is tested) over a clinically relevant time horizon.

The level that is determined may be the same as a control level or a cut off level or a threshold level, or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease (or a symptom thereof) in question or is not at risk for the disease.

Relative to a control level, the level that is determined may an increased level. As used herein, the term "increased" with respect to level (e.g., protein or mRNA level) refers to any % increase above a control level. In various embodiments, the increased level may be at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, at least or about a 95% increase, relative to a control level.

Relative to a control level, the level that is determined may a decreased level. As used herein, the term "decreased" with respect to level (e.g., protein or mRNA level) refers to any % decrease below a control level. In various embodiments, the decreased level may be at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, at least or about a 95% decrease, relative to a control level.

"Risk" in the context of the present disclosure, relates to the probability that an event will occur over a specific time period, as in the development of a SVD or a symptom thereof, and can mean a subject's "absolute" risk or "relative" risk. In various embodiments, a "high risk" subject is a subject who is likely to develop a SVD or symptom within, e.g., about 1, 2, 3, 4, or 5 years. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used [odds are according to the formula p/(1−p) where p is the probability of event and (1−p) is the probability of no event] to no-conversion.

Embodiments and examples are provided below to facilitate a more complete understanding of the invention. The following embodiments and examples illustrate the exemplary modes of making and practicing the invention. However, the scope of the invention is not limited to specific embodiments disclosed in these embodiments and examples, which are for purposes of illustration only, since alternative methods can be utilized to obtain similar results.

EMBODIMENTS

Embodiments include Embodiments P1 to P40 following.

Embodiment P1. A method for diagnosing a small vessel disease (SVD) in a subject in need thereof comprising
(a) providing a test sample from said subject;
(b) assaying the level of endostatin, High-Temperature Requirement A Serine Peptidase 1 (HTRA1), insulin-like growth factor binding protein 1 (IGFBP-1), and/or Neurogenic Locus Notch Homolog Protein 3 (NOTCH3) in the test sample; and (c) diagnosing the subject with the SVD if
  (i) the level of endostatin, IGFBP-1, and/or HTRA1 is elevated in the test sample compared to a normal control, and/or
  (ii) the level of NOTCH3 is reduced in the test sample compared to the normal control.

Embodiment P2. The method of Embodiment P1, wherein said subject is diagnosed with the SVD if (i) the level of endostatin, IGFBP-1, and/or HTRA1 is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in said test sample compared to a normal control; and/or (ii) the level of NOTCH3 reduced by about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% in said test sample compared to a normal control.

Embodiment P3. A method for identifying whether a subject is at risk of developing a SVD comprising
  (a) providing a test sample from said subject;
  (b) assaying the level of endostatin, IGFBP-1, HTRA1, and/or NOTCH3 in the test sample; and
  (c) identifying the subject as at risk of developing the SVD if
    (i) the level of endostatin, IGFBP-1, and/or HTRA1 is elevated in the test sample compared to a normal control, and/or
    (ii) the level of NOTCH3 is reduced in the test sample compared to the normal control.

Embodiment P4. The method of Embodiment P3, wherein said subject is identified as at risk of developing the SVD if (i) the level of endostatin, IGFBP-1, and/or HTRA1 is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in said test sample compared to a normal control; and/or (ii) the level of NOTCH3 reduced by about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% in said test sample compared to a normal control.

Embodiment P5. The method of Embodiment P3 or P4, further comprising directing the subject to obtain (i) additional screening or an additional diagnostic test for the SVD if the subject is identified as at risk of developing the SVD; or (ii) treatment to reduce, delay, or prevent the onset or progression of the SVD.

Embodiment P6. A method for monitoring whether a SVD is progressing in a subject who has been diagnosed with the SVD, comprising periodically determining the level of endostatin, IGFBP-1, HTRA1, and/or NOTCH3 in said subject, and
  (1) identifying the SVD as worsening if (i) the level of endostatin, IGFBP-1, and/or HTRA1 increases over time, and/or (ii) the level of NOTCH3 decreases over time;
  (2) identifying the SVD as improving if (i) the level of endostatin, IGFBP-1, and/or HTRA1 decreases over time, and/or (ii) the level of NOTCH3 increases over time; or
  (3) identifying the SVD as neither worsening nor improving if the level of endostatin, IGFBP-1, HTRA1, and/or NOTCH3 remains the same or about the same over time, wherein determining the level of endostatin, IGFBP-1, HTRA1, and/or NOTCH3 comprises
  (a) providing a test sample from said subject; and
  (b) assaying the level of endostatin, IGFBP-1, HTRA1, and/or NOTCH3 in the test sample.

Embodiment P7. The method of Embodiment P6, wherein the level of endostatin, IGFBP-1, NOTCH3, and/or HTRA1 is determined at least about 1, 2, 3, 4, 5, 6, 7, 8, 9, 10 or more times and/or at least once every 1, 2, 3, or 4 weeks; at least once every 1, 2, 3, 4, 5, or 6 weeks; or at least once every 1, 2, 3, 4, or 5 years.

Embodiment P8. A method for identifying a prognosis for a subject who has been diagnosed with a SVD comprising
  (a) providing a test sample from said subject;
  (b) assaying the level of endostatin, IGFBP-1, HTRA1, and/or NOTCH3 in the test sample; and
  (c) comparing the level of endostatin, IGFBP-1, HTRA1, and/or NOTCH3 determined in (b) to a value in a database to identify the subject's risk of suffering from a symptom of SVD.

Embodiment P9. The method of Embodiment P8, wherein said database contains (i) endostatin, IGFBP-1, HTRA1, and/or NOTCH3 level values from subjects who have suffered from said symptom of SVD; or (ii) absolute or relative risk values calculated based on endostatin, IGFBP-1, HTRA1, and/or NOTCH3 level values from subjects who have suffered from said symptom of SVD.

Embodiment P10. The method of Embodiment P9, wherein said absolute or relative risk values comprise mean or median level values calculated using endostatin, IGFBP-1, HTRA1, and/or NOTCH3 level values from subjects who have suffered from said symptom of SVD.

Embodiment P11. A method of prophylaxis for a SVD, comprising identifying whether a subject is at risk of suffering from SVD according to the method of Embodiment 3, and administering to the subject a compound that is used to treat the SVD if the subject is identified as at risk of suffering from SVD.

Embodiment P12. The method of Embodiment P11, wherein said compound comprises a an anti-angiogenic compound, an anti-vascular endothelial growth factor (VEGF) compound, an anti-platelet compound, an antihypertensive compound, a platelet antiaggregant, a cholesterol-lowering compound, a 3-hydroxy-3-methylglutaryl coenzyme A (HMG-CoA) reductase inhibitor, nimodipine, propentofylline, posatirelin, bevacizumab, ranibizumab, pegaptanib, aflibercept, nicardipine, verteporfin, anecortave acetate, triamcinolone acetonide, aspirin, dipyridamole, ticlopidine, a thrombolytic agent, an anticoagulant, or clopidogrel.

Embodiment P13. A method for adjusting the dose of a compound that is administered to a subject during a treatment regimen for a SVD, comprising periodically determining the level of endostatin, IGFBP-1, HTRA1, and/or NOTCH3 in the subject, and
  (1) increasing the dose of the compound if (i) the level of endostatin, IGFBP-1, and/or HTRA1 increases over time, and/or (ii) the level of NOTCH3 decreases over time;
  (2) maintaining or decreasing the dose of the compound if (i) the level of endostatin, IGFBP-1, and/or HTRA1 decreases over time, and/or (ii) the level of NOTCH3 increases over time; or
  (3) maintaining or increasing the dose of the compound if the level of endostatin, IGFBP-1, HTRA1, and/or NOTCH3 remains the same or about the same over time, wherein determining the level of endostatin, IGFBP-1, HTRA1, and/or NOTCH3 comprises
  (a) providing a test sample from said subject; and
  (b) assaying the level of endostatin, IGFBP-1, HTRA1, and/or NOTCH3 in the test sample.

Embodiment P14. A method for identifying whether a therapy has reduced or ameliorated a SVD in a subject comprising
  (a) providing a pre-therapy test sample from said subject;
  (b) assaying the pre-therapy level of endostatin, IGFBP-1, HTRA1, and/or NOTCH3 in the pre-therapy test sample;
  (c) administering the therapy to the subject;
  (d) providing a post-therapy test sample from said subject;
  (e) assaying the post-therapy level of endostatin, IGFBP-1, HTRA1, and/or NOTCH3 in the post-therapy test sample; and
  (f) identifying the therapy as having reduced or ameliorated said SVD if (i) the level of endostatin, IGFBP-1, and/or HTRA1 in the post-therapy test sample is lower than the level of endostatin, IGFBP-1, and/or HTRA1 in the pre-therapy test sample, and/or (ii) the level of NOTCH3 in the post-therapy test sample is higher than the level of NOTCH3 in the pre-therapy test sample.

Embodiment P15. The method of any one of Embodiments P1-P14, wherein the SVD comprises Age-Related Macular Degeneration (AMD).

Embodiment P16. The method of any one of Embodiments P1-P15, wherein the level of endostatin, IGFBP-1, HTRA1, and/or NOTCH3 is the level of endostatin and HTRA1.

Embodiment P17. The method of any one of Embodiments P1-P15, which does not comprise assaying and/or detecting the HTRA1.

Embodiment P18. The method of any one of Embodiments P1-P17, wherein NOTCH3 is an extracellular portion of NOTCH3.

Embodiment P19. The method of any one of Embodiments P1-P18, wherein the extracellular portion of NOTCH3 is the NOTCH3 extracellular domain (N3ECD).

Embodiment P20. The method of any one of Embodiments P1-P19, wherein said test sample comprises a bodily fluid from said subject.

Embodiment P21. The method of Embodiment P20, wherein said bodily fluid comprises whole blood, a component of whole blood, plasma, serum, saliva, tears, vitreous, cerebrospinal fluid, sweat, cerebrospinal fluid, or urine.

Embodiment P22. The method of any one of Embodiments P1-P21, wherein said test sample is other than a tissue biopsy.

Embodiment P23. The method of any one of Embodiments P1-P22, wherein the subject does not contain a mutated HTRA1 gene.

Embodiment P24. The method of any one of Embodiments P1-P23, which does not comprise assaying and/or detecting the level of Fas ligand (FasL).

Embodiment P25. The method of any one of Embodiments P1-P14 or P16-P24, wherein said SVD comprises cerebral SVD.

Embodiment P26. The method of any one of Embodiments P1-P14 or P16-P25, wherein said SVD comprises a stroke, vascular cognitive impairment, dementia, nephropathy, retinopathy, or neuropathy.

Embodiment P27. The method of any one of Embodiments P1-P14 or P16-P26, wherein said SVD comprises cerebral autosomal recessive arteriopathy with subcortical infarcts and leukoencephalopathy (CARASIL), age-related macular degeneration (AMD), cerebral autosomal-dominant arteriopathy with subcortical infarcts and leukoencephalopathy (CADASIL), NOTCH3 loss of function-associated SVD, nephropathy, microangiopathy, heart failure, Alagille syndrome, familial tetralogy of Fallot, patent ductus arteriosus, a cerebral cavernous malformation, pulmonary arterial hypertension, or diabetic retinopathy.

Embodiment P28. The method of any one of Embodiments P1-P25, wherein said SVD comprises AMD and said AMD is dry AMD or wet AMD.

Embodiment P29. The method of any one of Embodiments P1-P28, wherein said subject has diabetes.

Embodiment P30. The method of any one of Embodiments P1-P29, wherein assaying the level of endostatin, IGFBP-1, HTRA1, and/or NOTCH3 comprises contacting said endostatin, IGFBP-1, HTRA1, and/or NOTCH3 with an endostatin-specific, IGFBP specific HTRA1-specific and/or NOTCH3-specific binding agent.

Embodiment P31. The method of Embodiment P30, wherein said binding agent comprises an antibody or a fragment thereof, a polypeptide or a fragment thereof, or a nucleic acid.

Embodiment P32. The method of Embodiment P31, wherein said binding agent comprises an antibody or a fragment thereof.

Embodiment P33. The method of Embodiment P32, wherein said antibody comprises an anti-endostatin antibody, an anti-IGFBP-1 antibody, an anti-HTRA1 antibody or an anti-NOTCH3 antibody.

Embodiment P34. The method of Embodiment P32 or P33, wherein said antibody or fragment thereof is attached to a solid support.

Embodiment P35. The method of any one of Embodiments P1-P34, wherein said assaying comprises an enzyme immunoassay (EIA).

Embodiment P36. The method of any one of Embodiments P1-P35, wherein said assaying comprises an enzyme-linked immunosorbent assay (ELISA), a Western blot, a mass spectrometry assay, a radioimmunoassay, or a fluoro-immunoassay.

Embodiment P37. The method of Embodiment 31, wherein said nucleic acid comprises a probe or a primer that is complementary to mRNA that encodes collagen18α1/endostatin, IGFBP-1, HTRA1, and/or NOTCH3.

Embodiment P38. The method of any one of Embodiments P1-P31 or 37, wherein said assaying comprises a polymerase chain reaction (PCR).

Embodiment P39. A kit comprising
  (a) at least two agents selected from the group consisting of (i) an agent for detecting the level of endostatin; (ii) an agent for detecting the level of NOTCH3; (iii) an agent for detecting the level of IGFBP-1; and (iv) an agent for detecting the level of HTRA1, and
  (b) instructions for using the agent for diagnosing a SVD, for identifying whether a subject is at risk of developing the SVD, for determining the prognosis of the SVD, for determining the progression of SVD, for assessing the efficacy of a treatment for the SVD, and/or for adjusting the dose of a compound during the treatment of SVD.

Embodiment P40. A diagnostic system comprising
  (a) an assortment, collection, or compilation of test results data representing the level of endostatin, IGFBP-1, HTRA1, and/or NOTCH3 in a plurality of test samples;
  (b) a means for computing an index value using said level, wherein the index value comprises a diagnostic, prognostic, progression, or treatment score; and (c) a means for reporting the index value.

Additional embodiments include Embodiments 1 to 69 following:

Embodiment 1. A method for diagnosing a small vessel disease (SVD) in a subject comprising
- (a) assaying the level of (i) Neurogenic Locus Notch Homolog Protein 3 (NOTCH3), collagen18α1/endostatin, High-Temperature Requirement A Serine Peptidase 1 (HTRA1), and/or insulin-like growth factor binding protein 1 (IGFBP-1), (ii) a protein-protein complex comprising NOTCH3 bound to collagen18α1/endostatin, HTRA1, IGFBP-1, and/or NOTCH3, in a test sample from said subject; and
- (b) diagnosing the subject with the SVD if
    - (i) the level of collagen18α1/endostatin, IGFBP-1, and/or HTRA1 is elevated in the test sample compared to a normal control, and/or
    - (ii) the level of collagen18α1/endostatin or NOTCH3 is reduced in the test sample compared to the normal control, and/or
    - (iii) the protein-protein complex comprising NOTCH3 bound to collagen18α1/endostatin, HTRA1, IGFBP-1, and/or NOTCH3 is detected in the test sample.

Embodiment 2. The method of Embodiment 1, wherein NOTCH3 is a NOTCH3 extracellular domain (N3ECD) protein comprising the amino acid sequence of SEQ ID NO: 5, and wherein assaying the level of NOTCH3 comprises contacting the N3ECD protein with an anti-N3ECD antibody.

Embodiment 3. The method of Embodiment 1, wherein (i) assaying the level of NOTCH3 comprises detecting the level of a NOTCH3 protein comprising the amino acid sequence of SEQ ID NO: 3 or 5; (ii) assaying the level of collagen18α1/endostatin comprises detecting the level of a collagen18α1/endostatin protein comprising the amino acid sequence of SEQ ID NO: 1; (iii) assaying the level of HTRA1 comprises detecting the level of a HTRA1 protein having the amino acid sequence of SEQ ID NO: 9; and/or (iv) assaying the level of IGFBP-1 comprises detecting the level of an IGFBP-1 protein comprising the amino acid sequence of SEQ ID NO: 7.

Embodiment 4. The method of any one of Embodiments 1-3 wherein (i) assaying the level of collagen18α1/endostatin comprises contacting the collagen18α1/endostatin protein with an anti-collagen18α1/endostatin antibody; (ii) assaying the level of IGFBP-1 comprises contacting the IGFBP-1 potein with an anti-IGFBP-1 antibody; (iii) assaying the level of HTRA1 comprises contacting the HTRA1 protein with an anti-HTRA1 antibody; and/or (iv) assaying the level of NOTCH3 comprises contacting the NOTCH3 protein with an anti-NOTCH3 antibody.

Embodiment 5. The method of Embodiment 1, wherein (i) assaying the level of collagen18α1/endostatin comprises detecting the level of collagen18α1/endostatin mRNA; (ii) assaying the level of HTRA1 comprises detecting the level of HTRA1 mRNA; (iii) assaying the level of IGFBP-1 comprises detecting the level of IGFBP-1 mRNA; and/or (iv) assaying the level of NOTCH3 comprises detecting the level of NOTCH3 mRNA.

Embodiment 6. The method of any one of Embodiments 1-5, wherein (i) detecting the level of collagen18α1/endostatin mRNA comprises contacting the collagen18α1/endostatin mRNA with a probe or a primer that is complementary to SEQ ID NO: 2; (ii) detecting the level of HTRA1 mRNA comprises contacting the HTRA1 mRNA with a probe or a primer that is complementary to SEQ ID NO: 10; (iii) detecting the level of IGFBP-1 mRNA comprises contacting the IGFBP-1 mRNA with a probe or a primer that is complementary to SEQ ID NO: 8; and/or (iv) detecting the level of NOTCH3 mRNA comprises contacting the NOTCH3 mRNA with a probe or a primer that is complementary to SEQ ID NO: 4.

Embodiment 7. The method of Embodiment 1, wherein said subject is diagnosed with the SVD if (i) the level of collagen18α1/endostatin, IGFBP-1, and/or HTRA1 is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in said test sample compared to a normal control; and/or (ii) the level of collagen18α1/endostatin or NOTCH3 reduced by about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% in said test sample compared to a normal control.

Embodiment 8. A method for identifying whether a subject is at risk of developing a SVD comprising
- (a) assaying the level of (i) collagen18α1/endostatin, IGFBP-1, HTRA1, and/or NOTCH3, and/or (ii) a protein-protein complex comprising NOTCH3 bound to collagen18α1/endostatin, HTRA1, IGFBP-1, and/or NOTCH3 in a test sample from said subject; and
- (b) identifying the subject as at risk of developing the SVD if
    - (i) the level of collagen18α1/endostatin, IGFBP-1, and/or HTRA1 is elevated in the test sample compared to a normal control, and/or
    - (ii) the level of collagen18α1/endostatin or NOTCH3 is reduced in the test sample compared to the normal control, and/or
    - (iii) the protein-protein complex comprising NOTCH3 bound to collagen18α1/endostatin, HTRA1, IGFBP-1, and/or NOTCH3 is detected in the test sample.

Embodiment 9. The method of Embodiment 8, wherein said subject is identified as at risk of developing the SVD if (i) the level of collagen18α1/endostatin, IGFBP-1, and/or HTRA1 is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in said test sample compared to a normal control; and/or (ii) the level of collagen18α1/endostatin or NOTCH3 reduced by about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100%, in said test sample compared to a normal control.

Embodiment 10. The method of Embodiment 8, further comprising directing the subject to obtain (i) additional screening or an additional diagnostic test for the SVD if the subject is identified as at risk of developing the SVD; or (ii) treatment to reduce, delay, or prevent the onset or progression of the SVD.

Embodiment 11. A method for monitoring whether a SVD is progressing in a subject who has been diagnosed with the SVD, comprising periodically determining the level of collagen18α1/endostatin, IGFBP-1, HTRA1, NOTCH3, and/or a protein-protein complex comprising NOTCH3 bound to collagen18α1/endostatin, HTRA1, IGFBP-1, and/or NOTCH3 in said subject, and
- (1) identifying the SVD as worsening if (i) the level of collagen18α1/endostatin, IGFBP-1, HTRA1, and/or the complex increases over time, and/or (ii) the level of collagen18α1/endostatin or NOTCH3 decreases over time;

(2) identifying the SVD as improving if (i) the level of collagen18α1/endostatin, IGFBP-1, HTRA1, and/or the complex decreases over time, and/or (ii) the level of collagen18α1/endostatin or NOTCH3 increases over time; or (3) identifying the SVD as neither worsening nor improving if the level of collagen18α1/endostatin, IGFBP-1, HTRA1, NOTCH3, and/or the complex remains the same or about the same over time, wherein determining the level of collagen18α1/endostatin, IGFBP-1, HTRA1, and/or NOTCH3 comprises assaying the level of collagen18α1/endostatin, IGFBP-1, HTRA1, NOTCH3, and/or the complex in a test sample from the subject.

Embodiment 12. The method of Embodiment 11, wherein the level of collagen18α1/endostatin, IGFBP-1, NOTCH3, HTRA1, and/or the complex is determined at least about 1, 2, 3, 4, 5, 6, 7, 8, 9, 10 or more times and/or at least once every 1, 2, 3, or 4 weeks; at least once every 1, 2, 3, 4, 5, or 6 weeks; or at least once every 1, 2, 3, 4, or 5 years.

Embodiment 13. A method for identifying a prognosis for a subject who has been diagnosed with a SVD comprising
(a) assaying the level of collagen18α1/endostatin, IGFBP-1, HTRA1, NOTCH3, and/or a protein-protein complex comprising NOTCH3 bound to collagen18α1/endostatin, HTRA1, IGFBP-1, and/or NOTCH3 in a test sample from the subject; and
(b) comparing the level of collagen18α1/endostatin, IGFBP-1, HTRA1, NOTCH3, and/or the complex determined in (a) to a value in a database to identify the subject's risk of suffering from a symptom of SVD.

Embodiment 14. The method of Embodiment 13, wherein said database contains (i) collagen18α1/endostatin, IGFBP-1, HTRA1, NOTCH3, and/or complex level values from subjects who have suffered from said symptom of SVD; or (ii) absolute or relative risk values calculated based on collagen18α1/endostatin, IGFBP-1, HTRA1, NOTCH3, and/or complex level values from subjects who have suffered from said symptom of SVD.

Embodiment 15. The method of Embodiment 14, wherein said absolute or relative risk values comprise mean or median level values calculated using collagen18α1/endostatin, IGFBP-1, HTRA1, NOTCH3, complex level values from subjects who have suffered from said symptom of SVD.

Embodiment 16. A method of prophylaxis for a SVD, and administering to a subject a compound that is used to treat the SVD if the subject has been identified as at risk of suffering from SVD according to the method of Embodiment 3.

Embodiment 17. The method of Embodiment 16, wherein said compound comprises a an anti-angiogenic compound, an anti-vascular endothelial growth factor (VEGF) compound, an anti-platelet compound, an antihypertensive compound, a platelet antiaggregant, a cholesterol-lowering compound, a 3-hydroxy-3-methylglutaryl coenzyme A (HMG-CoA) reductase inhibitor, nimodipine, propentofylline, posatirelin, bevacizumab, ranibizumab, pegaptanib, aflibercept, nicardipine, verteporfin, anecortave acetate, triamcinolone acetonide, aspirin, dipyridamole, ticlopidine, a thrombolytic agent, an anticoagulant, or clopidogrel.

Embodiment 18. The method of Embodiment 17, wherein the SVD is cerebral autosomal-dominant arteriopathy with subcortical infarcts and leukoencephalopathy (CADASIL) and the compound is not a thrombolytic agent.

Embodiment 19. A method for adjusting the dose of a compound that is administered to a subject during a treatment regimen for a SVD, comprising periodically determining the level of collagen18α1/endostatin, IGFBP-1, HTRA1, NOTCH3, and/or a protein-protein complex comprising NOTCH3 bound to collagen18α1/endostatin, HTRA1, IGFBP-1, and/or NOTCH3 in the subject, and (1) increasing the dose of the compound if (i) the level of collagen18α1/endostatin, IGFBP-1, HTRA1, and/or the complex increases over time, and/or (ii) the level of collagen18α1/endostatin or NOTCH3 decreases over time;

(2) maintaining or decreasing the dose of the compound if (i) the level of collagen18α1/endostatin, IGFBP-1, HTRA1, and/or the complex decreases over time, and/or (ii) the level of collagen18α1/endostatin or NOTCH3 increases over time; or (3) maintaining or increasing the dose of the compound if the level of collagen18α1/endostatin, IGFBP-1, HTRA1, NOTCH3, and/or the complex remains the same or about the same over time, wherein determining the level of collagen18α1/endostatin, IGFBP-1, HTRA1, and/or NOTCH3 comprises assaying the level of collagen18α1/endostatin, IGFBP-1, HTRA1, NOTCH3, and/or the complex in a test sample from the subject.

Embodiment 20. A method for identifying whether a therapy has reduced or ameliorated a SVD in a subject comprising
(a) assaying the pre-therapy level of collagen18α1/endostatin, IGFBP-1, HTRA1, NOTCH3, and/or a protein-protein complex comprising NOTCH3 bound to collagen18α1/endostatin, HTRA1, IGFBP-1, and/or NOTCH3 in a pre-therapy test sample from the subject;
(b) administering the therapy to the subject;
(c) assaying the post-therapy level of collagen18α1/endostatin, IGFBP-1, HTRA1, NOTCH3, and/or the complex in a post-therapy test sample from the subject; and
(d) identifying the therapy as having reduced or ameliorated said SVD if (i) the level of collagen18α1/endostatin, IGFBP-1, HTRA1, and/or the complex in the post-therapy test sample is lower than the level of collagen18α1/endostatin, IGFBP-1, HTRA1, and/or the complex in the pre-therapy test sample, and/or (ii) the level of collagen18α1/endostatin pr NOTCH3 in the post-therapy test sample is higher than the level of collagen18α1/endostatin or NOTCH3 in the pre-therapy test sample.

Embodiment 21. The method of any one of Embodiments 1-20, wherein the SVD comprises Age-Related Macular Degeneration (AMD).

Embodiment 22. The method of any one of Embodiments 1-21, wherein the level of collagen18α1/endostatin, IGFBP-1, HTRA1, and/or NOTCH3 is the level of collagen18α1/endostatin and HTRA1.

Embodiment 23. The method of any one of Embodiments 1-22, which does not comprise assaying and/or detecting the HTRA1.

Embodiment 24. The method of any one of Embodiments 1-23, wherein NOTCH3 is an extracellular portion of NOTCH3.

Embodiment 25. The method of any one of Embodiments 1-24, wherein the extracellular portion of NOTCH3 is the NOTCH3 extracellular domain (N3ECD).

Embodiment 26. The method of any one of Embodiments 1-25, wherein said test sample comprises a bodily fluid from said subject.

Embodiment 27. The method of any one of Embodiments 1-26, wherein said bodily fluid comprises whole blood, a component of whole blood, plasma, serum, saliva, tears, vitreous, cerebrospinal fluid, sweat, cerebrospinal fluid, or urine.

Embodiment 28. The method of any one of Embodiments 1-27, wherein said test sample is other than a tissue biopsy.

Embodiment 29. The method of any one of Embodiments 1-28, wherein the subject does not contain a mutated HTRA1 gene.

Embodiment 30. The method of any one of Embodiments 1-29, which does not comprise assaying and/or detecting the level of Fas ligand (FasL).

Embodiment 31. The method of any one of Embodiments 1-30, wherein said SVD comprises cerebral SVD.

Embodiment 32. The method of any one of Embodiments 1-31, wherein said SVD comprises a stroke, vascular cognitive impairment, dementia, nephropathy, retinopathy, or neuropathy.

Embodiment 33. The method of any one of Embodiments 1-32, wherein said SVD comprises cerebral autosomal recessive arteriopathy with subcortical infarcts and leukoencephalopathy (CARASIL), age-related macular degeneration (AMD), CADASIL, NOTCH3 loss of function-associated SVD, nephropathy, microangiopathy, heart failure, Alagille syndrome, familial tetralogy of Fallot, patent ductus arteriosus, a cerebral cavernous malformation, pulmonary arterial hypertension, or diabetic retinopathy.

Embodiment 34. The method of any one of Embodiments 1-33, wherein said SVD comprises AMD and said AMD is dry AMD or wet AMD.

Embodiment 35. The method of any one of Embodiments 1-34, wherein said subject has diabetes.

Embodiment 36. The method of any one of Embodiments 1-35, wherein assaying the level of collagen18α1/endostatin, IGFBP-1, HTRA1, and/or NOTCH3 comprises contacting said collagen18α1/endostatin, IGFBP-1, HTRA1, and/or NOTCH3 with an collagen18α1/endostatin-specific, IGFBP-1-specific HTRA1-specific and/or NOTCH3-specific binding agent.

Embodiment 37. The method of Embodiment 36, wherein said binding agent comprises an antibody or a fragment thereof, a polypeptide or a fragment thereof, or a nucleic acid.

Embodiment 38. The method of Embodiment 37, wherein said binding agent comprises an antibody or a fragment thereof.

Embodiment 39. The method of Embodiment 38, wherein said antibody comprises an anti-collagen18α1/endostatin antibody, an anti-IGFBP-1 antibody, an anti-HTRA1 antibody or an anti-NOTCH3 antibody.

Embodiment 40. The method of Embodiment 38, wherein said antibody or fragment thereof is attached to a solid support.

Embodiment 41. The method of any one of Embodiments 1-40 wherein said assaying comprises an enzyme immunoassay (EIA).

Embodiment 42. The method of any one of Embodiments 1-41, wherein said assaying comprises an enzyme-linked immunosorbent assay (ELISA), a Western blot, a mass spectrometry assay, a radioimmunoassay, or a fluoroimmunoassay.

Embodiment 43. The method of any one of Embodiments 1-42, wherein said assaying comprises high-performance liquid chromatography (HPLC), liquid chromatography-mass spectrometry (LC/MS), protein immunoprecipitation, immunoelectrophoresis, or protein immunostaining.

Embodiment 44. The method of any one of Embodiments 1-43, wherein said nucleic acid comprises a probe or a primer that is complementary to mRNA that encodes collagen18α1/endostatin, IGFBP-1, HTRA1, and/or NOTCH3.

Embodiment 45. The method of any one of Embodiments 1-44, wherein said assaying comprises a polymerase chain reaction (PCR).

Embodiment 46. The method of any one of Embodiments 1-45, wherein said assaying comprises quantitative reverse transcription PCR, microarray analysis, RNA sequencing, Northern analysis, a Nuclease Protection Assay, or in situ hybridization.

Embodiment 47. A kit comprising
(a) at least two agents selected from the group consisting of (i) an agent for detecting the level of collagen18α1/endostatin; (ii) an agent for detecting the level of NOTCH3; (iii) an agent for detecting the level of IGFBP-1; and (iv) an agent for detecting the level of HTRA1, and
(b) instructions for using the agent for diagnosing a SVD, for identifying whether a subject is at risk of developing the SVD, for determining the prognosis of the SVD, for determining the progression of SVD, for assessing the efficacy of a treatment for the SVD, and/or for adjusting the dose of a compound during the treatment of SVD.

Embodiment 48. A diagnostic system comprising
(a) an assortment, collection, or compilation of test results data representing the level of collagen18α1/endostatin, IGFBP-1, HTRA1, and/or NOTCH3 in a plurality of test samples;
(b) a means for computing an index value using said level, wherein the index value comprises a diagnostic, prognostic, progression, or treatment score; and
(c) a means for reporting the index value.

Embodiment 49. A method for detecting collagen18α1/endostatin, IGFBP-1, HTRA1, NOTCH3, and/or a protein-protein complex comprising NOTCH3 bound to collagen18α1/endostatin, HTRA1, IGFBP-1, and/or NOTCH3 in a subject, the method comprising assaying the level of collagen18α1/endostatin, IGFBP-1, HTRA1, NOTCH3, and/or the complex in a test sample from the subject, wherein the subject has an SVD.

Embodiment 50. The method of Embodiment 49, wherein the level of collagen18α1/endostatin, IGFBP-1, HTRA1, and/or NOTCH3 is the level of collagen18α1/endostatin protein, IGFBP-1 protein, HTRA1 protein, and/or NOTCH3 protein.

Embodiment 51. The method of Embodiment 50, wherein detecting the level of a protein comprises immunoprecipitating the protein and then measuring the level of the protein by mass spectrometry.

Embodiment 52. The method of Embodiment 50, wherein assaying the level of collagen18α1/endostatin protein, IGFBP-1 protein, HTRA1 protein, and/or NOTCH3 protein comprises contacting the sample with an anti-collagen18α1/endostatin antibody, an anti-IGFBP-1 antibody, an anti-HTRA1 antibody, and/or an anti-NOTCH3 antibody, and detecting binding between collagen18α1/endostatin and the anti-collagen18α1/endostatin antibody, IGFBP-1 and the anti-IGFBP-1 antibody, HTRA1 and the anti-HTRA1 antibody, and/or NOTCH3 and the anti-NOTCH3 antibody.

Embodiment 53. The method of Embodiment 49, which does not comprise assaying the level of HTRA1.

Embodiment 54. The method of c Embodiment laim 49, which does not comprise assaying the level of Fas ligand (FasL).

Embodiment 55. The method of Embodiment 49, wherein NOTCH3 is an extracellular portion of NOTCH3.

Embodiment 56. The method of Embodiment 55, wherein the extracellular portion of NOTCH3 is the NOTCH3 extracellular domain (N3ECD).

Embodiment 57. The method of Embodiment 49, wherein said test sample comprises a bodily fluid from said subject.

Embodiment 58. The method of Embodiment 49, wherein said bodily fluid comprises whole blood, a component of whole blood, plasma, serum, saliva, tears, vitreous, cerebrospinal fluid, sweat, cerebrospinal fluid, or urine.

Embodiment 59. The method of Embodiment 49, wherein said test sample is other than a tissue biopsy.

Embodiment 60. The method of Embodiment 49, wherein assaying does not comprise a microarray.

Embodiment 61. The method of Embodiment 49, wherein no more than 1000 proteins or mRNA molecules is assayed.

Embodiment 62. The method of Embodiment 49, comprising assaying the level of NOTCH3.

Embodiment 63. The method of Embodiment 62, comprising assaying the level of collagen18α1/endostatin.

Embodiment 64. The method of Embodiment 62, comprising assaying the level of IGFBP-1.

Embodiment 65. The method of Embodiment 62, comprising assaying the level of HTRA1.

Embodiment 66. The method of Embodiment 49, comprising assaying the level of the complex.

Embodiment 67. The method of Embodiment 49, wherein herein said SVD comprises cerebral autosomal recessive arteriopathy with subcortical infarcts and leukoencephalopathy (CARASIL), age-related macular degeneration (AMD), cerebral autosomal-dominant arteriopathy with subcortical infarcts and leukoencephalopathy (CADASIL), NOTCH3 loss of function-associated SVD, nephropathy or another SVD of the kidney, proximal 19p13.12 microdeletion syndrome, myocardial ischemia, microangiopathy, heart failure, Alagille syndrome, familial tetralogy of Fallot, patent ductus arteriosus, a cerebral cavernous malformation, a HTRA1-associated small vessel disease, pulmonary arterial hypertension, retinopathy, or diabetic retinopathy.

Embodiment 68. A method of treating or preventing a SVD in a subject who has been diagnosed as having a SVD according to Embodiment 1, comprising administering to a subject a compound that is used to treat the SVD.

Embodiment 69. The method of Embodiment 68, wherein said compound comprises a an anti-angiogenic compound, an anti-vascular endothelial growth factor (VEGF) compound, an anti-platelet compound, an antihypertensive compound, a platelet antiaggregant, a cholesterol-lowering compound, a 3-hydroxy-3-methylglutaryl coenzyme A (HMG-CoA) reductase inhibitor, nimodipine, propentofylline, posatirelin, bevacizumab, ranibizumab, pegaptanib, aflibercept, nicardipine, verteporfin, anecortave acetate, triamcinolone acetonide, aspirin, dipyridamole, ticlopidine, a thrombolytic agent, an anticoagulant, or clopidogrel.

Example 1: Blood Biomarkers in a Mouse Model of CADASIL

Mutations in NOTCH3 are the cause of cerebral autosomal dominant arteriopathy with subcortical infarcts and leukoencephalopathy (CADASIL), a neurological disorder characterized by stroke, and vascular cognitive impairment and dementia. Loss of vascular smooth muscle cells (VSMC) and accumulation of granular osmiophilic material (GOM) deposits are hallmarks of CADASIL. There are no therapies for CADASIL and experimental endpoints to examine the preclinical efficacy of potential drugs are lacking. In this Example a mouse carrying the C455R mutation in NOTCH3 was used to identify biomarkers associated with CADASIL. Mass spectrometry and antibody arrays were used to explore the aorta and blood proteomes of CADASIL mice, ELISA assays were utilized for biomarker validation, a ligand-dependent assay was applied to examine the relationship between NOTCH signaling and biomarker expression, and retinal histology was performed for quantification of VSMC loss in arteries. Two-hundred day-old mice with the C455R CADASIL mutation in NOTCH3 mice display robust VSMC loss in retinal arteries and had increased plasma levels of collagen18α1/endostatin (col18α1) and high-temperature requirement A serine peptidase 1 (HTRA1) and reduced levels of NOTCH3 extracellular domain (N3ECD), compared to control wild type mice. Measurements of plasma endostatin, HTRA1 and N3ECD, along with VSMC quantification in retinal arteries, may serve as surrogate endpoints for assessing efficacy in preclinical therapeutic studies of CADASIL using mice.

Ischemic cerebral small-vessel disease is a prevalent cause of stroke and a strong contributor to vascular cognitive impairment and dementia (Snyder et al., 2015, Alzheimers Dement. 11, 710-7). Multiple clinical studies show strong an association among ischemic cerebral small-vessel disease, aging, and cardiovascular risk factors (Kalaria, 2012, Stroke; a journal of cerebral circulation. 43, 2526-34; Thompson and Hakim, 2009, Stroke: J. Cereb. Circ. 40, e322-e330; Vermeer et al., 2007, The Lancet. Neurology. 6, 611-9). Little is known about the cellular and molecular mechanisms underlying the development of ischemic cerebral small-vessel disease and therapies are lacking. Mendelian conditions resembling key aspects of ischemic cerebral small-vessel disease, in the absence of cardiovascular risk factors, have been described in adult patients (Gould et al., 2006, The New England Journal of Medicine. 354, 1489-96; Hara et al., 2009; Joutel and Faraci, 2014). The study of these inherited ischemic cerebral small-vessel diseases may reveal key pathophysiological mechanisms, uncover biomarkers with diagnostic or prognostic potential, and define molecular targets for rational therapeutics. One such ischemic cerebral small-vessel disease is cerebral autosomal dominant arteriopathy with subcortical infarcts and leukoencephalopathy, (CADASIL), the most common form of inherited SVD (Chabriat et al., 2009, The Lancet. Neurology. 8, 643-53).

Patients with CADASIL often suffer from migraines in childhood, have recurrent ischemic strokes in the third and fourth decade of life, and experience progressive cognitive impairment (Dichgans et al., 1998, Annals of neurology. 44, 731-9). CADASIL is caused by mutations in the NOTCH3 gene, which encodes for one of four NOTCH receptor paralogues in mammals (Joutel et al., 1996, Nature. 383, 707-10). Most CADASIL mutations in NOTCH3 affect cysteine residues located within the epidermal growth factor-like repeats in the extracellular domain (Brass et al., 2009, The New England Journal of Medicine. 360, 1656-65; Dichgans et al., 2000, European journal of human genetics: EJHG. 8, 280-5; Joutel et al., 1997, Lancet. 350, 1511-5; Louvi et al., 2006, Developmental neuroscience. 28, 5-12). Postmortem studies of tissue from CADASIL patients reveal a non-amyloid, non-atherosclerotic, arteriopathy. The characteristics of this arteriopathy include VSMC death and the accumulation of deposits, detected by electron microscopy, known as granular osmiophilic material (GOM) (Baudrimont et al., 1993, Stroke: J. Cereb. Circ. 24, 122-5; Ruchoux et al., 1995, Acta neuropathologica. 89, 500-12; Ruchoux and Maurage, 1997, Journal of Neuropathology and Experimental Neurology. 56, 947-64; Tikka et al., 2009, Brain: J. Neurol. 132, 933-9). GOM deposits are specific to CADASIL and their identification in skin biopsies or brain autopsies is diagnostic (Tikka et al., 2009, Brain: J. Neurol., 132, 933-9). Biochemical studies of vessels of postmortem CADASIL cases and mouse models identified collagen 18 alpha 1(Col18α1)/endostatin, clusterin (Arboleda-Velasquez et al., 2011, Proc Natl Acad Sci USA. 108, E128-35), NOTCH3 ectodomain (N3ECD), and tissue inhibitor of metalloproteinases 3 (TIMP3) as GOM components (Ishiko et al., 2006, Acta Neuropathologica. 112, 333-9; Monet-Lepretre et. al., 2013, Brain. 136, 1830-45).

In this Example, published CADASIL mouse models carrying either the C455R or R1031C mutations in NOTCH3 were used. The C455R CADASIL mutation was described in a Colombian family in whom stroke occurs earlier and MRI abnormalities are more extensive than in patients carrying the R1031C, also described in a Colombian pedigree (Arboleda-Velasquez et al., 2002, Neurology. 59, 277-9). Previous work showed that the C455R (located in the ligand-binding domain of the NOTCH3 receptor) and the R1031C (located outside this region) mutations define different hypomorphic activity states of the NOTCH3 receptor and that mice carrying these mutations develop GOM and other age-dependent phenotypes that resemble the human condition (Arboleda-Velasquez et al., 2011, Proc Natl Acad Sci USA. 108, E128-35).

The availability of multiple CADASIL animal models, including those used in this work, allow for preclinical testing of experimental drugs (Arboleda-Velasquez et al., 2011, Proc Natl Acad Sci USA. 108, E128-35; Joutel and Faraci, 2014, Stroke: J. Cereb. Circ.). Such studies, as well as clinical diagnostic and treatment processes, would be greatly facilitated by the identification of specific markers of disease progression that are measurable, sensitive, and robust. The data below identifies blood biomarkers associated with CADASIL in a mouse model carrying non-synonymous mutations in NOTCH3. Blood plasma from knock-in mice models carrying NOTCH3 mutations identical to those found in Colombian families (Arboleda-Velasquez et al., 2008, 2011) was used for biomarker discovery and validation.

Screening of CADASIL Biomarkers in Mouse Plasma

Figure 2:
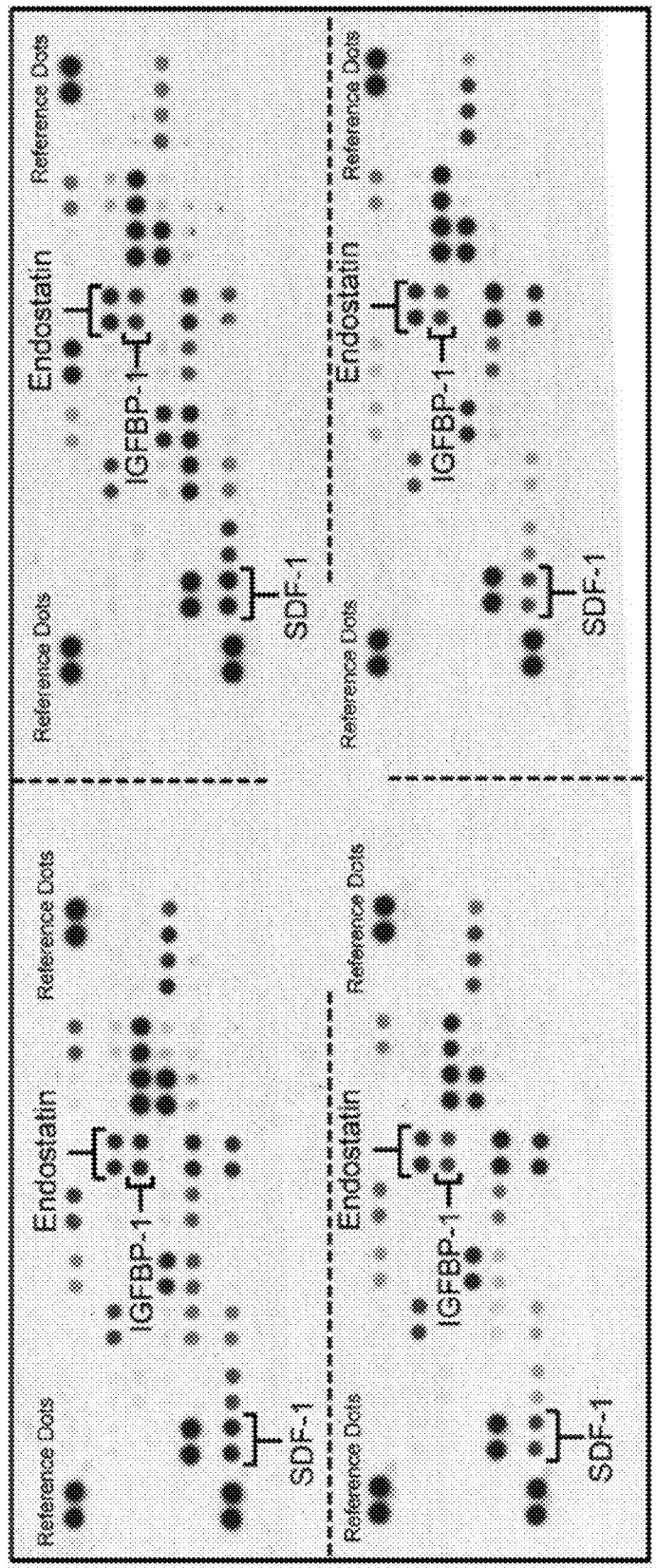
FIG. 2 is an image of a dot blot relating to a proteomic screen in N3KO mice. Dot blots show levels of specific proteins found in plasma from two male NOTCH3 knockout (N3KO) mice (200 d) or two rescued/control (N3KO; WT76+/−; SM22-Cre) in which a wild type human NOTCH3 is expressed in VSMC. Col18α1/endostatin was found to be differentially expressed, as established by a variance analysis.

Previous analyses of mice and humans carrying CADASIL mutations in NOTCH3 identified col18a1/endostatin, a potent and pleiotropic anti-angiogenic factor, as a protein accumulating in CADASIL vessels and a GOM component (Arboleda-Velasquez et al., 2011, Proc Natl Acad Sci USA. 108, E128-35; O'Reilly et al., 1997, Cell. 88, 277-85). Surprisingly, increased levels of endostatin were found in the blood of mice carrying CADASIL mutations. An antibody array capable of detecting 53 angiogenesis-related proteins was to determine whether endostatin, and/or other angiogenesis-related proteins, could be detected in plasma samples from our transgenic mice. The plasma of knock-in mice expressing the human WT NOTCH3 protein (N3KO; WT76+/−; SM22-Cre) to that of mice expressing the C455R CADASIL mutant receptor (N3KO; C455R+/−; SM22-Cre) at 100 and 200 days old, all in a mouse endogenous NOTCH3 knockout background (N3KO) (FIG. 1 and FIG. 7A). Furthermore, to examine whether any angiogenic-related protein candidates were regulated by NOTCH3 function, their expression was also compared in plasma from 200-day old mice lacking NOTCH3, N3KO, and N3KO mice in which NOTCH3 expression was restored in vessels using a conditional transgenic approach, N3KO; WT76+/−; SM22-Cre mice (FIG. 2 and FIG. 7A).

Figure 3B:
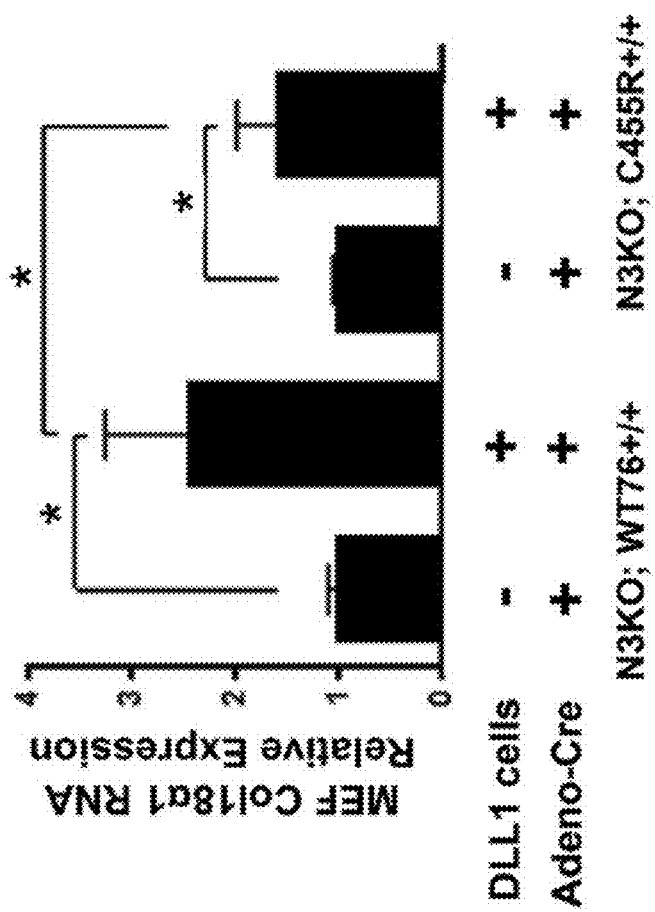
FIG. 3B: Primary cultures of MEFs from Cre-inducible CADASIL (N3KO; C455R+/+) or control mice (N3KO; WT76+/+) were placed in monocultures or cocultures with cells expressing DLL1 (ROSA26$^{DLL1+/+}$, a NOTCH ligand. Monocultures had no significant change in col18α1 mRNA expression, whereas cocultures with DLL1 significantly increased col18α1 mRNA expression. Expression was significantly more robust, however, in N3KO; WT76+/+ cocultures compared to N3KO; C455R+/+ cocultures. Asterisks (*) indicate P-value<0.05 (unpaired t-test).
Figure 3A:
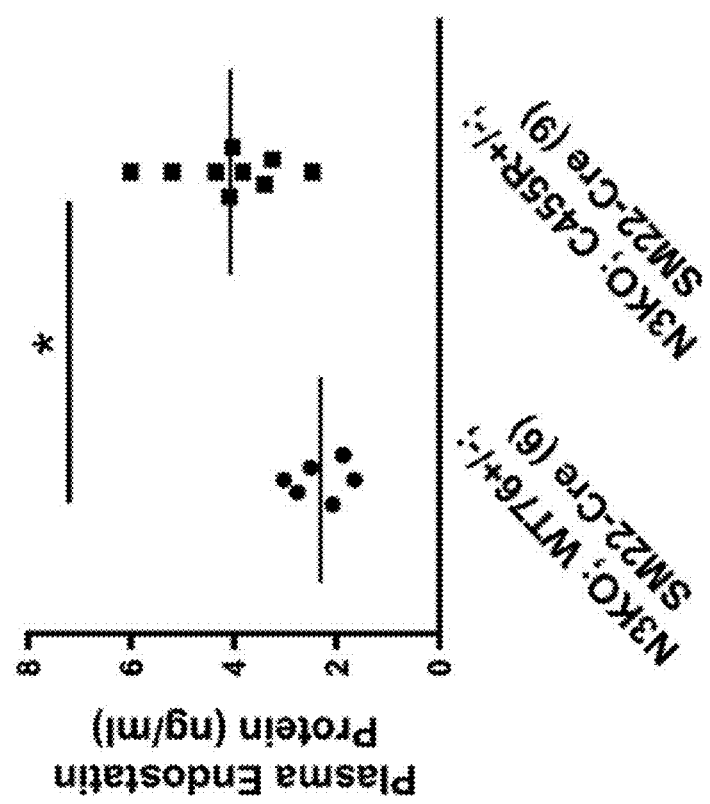
FIGS. 3A and B are graphs showing that endostatin is misregulated in CADASIL.

Insulin-like growth factor-binding protein-1 (IGFBP-1), stromal cell-derived factor-1 (SDF-1), and col18α1/endostatin were identified as potential biomarkers based on a variance analysis (see Methods). IGFBP-1 was increased in both 100- and 200-day old N3KO; C455R+/−; SM22-Cre mice (FIG. 1 and FIG. 7A), with a fold change of 2.029 and 4.562, respectively). SDF-1 was more abundant in 100-day old N3KO; C455R+/−SM22-Cre mice (1.752-fold-change) and less abundant in the 200-day old N3KO; C455R+/−; SM22-Cre mice (0.344-fold change, FIG. 1 and FIG. 7A). Col18α1/endostatin, was significantly less abundant (0.800 fold change) in the 100-day-old N3KO; C455R+/−; SM22-Cre mice, but, remained unchanged (1.025-fold change) in the 200-day old mice (FIG. 1 and FIG. 7A). Because protein-protein interactions within complex samples have been reported when using antibody arrays (Kodadek, 2001, Chem Biol. 8, 105-15). ELISA was utilized to validate the results. Analysis in 200-day old N3KO; C455R+/−; SM22-Cre mouse plasma using ELISA showed a significant increase in plasma circulating col18α1/endostatin (FIG. 3A, 1.76-fold change, P<0.01).

IGFBP-1 and SDF-1 levels were not changed in the plasma of mice from functional rescue comparison (N3KO vs. N3KO; WT76+/−; SM22-Cre), whereas col18α1/endostatin was more abundant in the N3KO; WT76+/−; SM22-Cre mouse when compared to the N3KO mouse, suggesting that col18α1/endostatin expression may be regulated by NOTCH3 signaling (FIG. 2 and FIG. 7A). Using a ligand-dependent NOTCH signaling assay (Arboleda-Velasquez et al., 2011) coculture of MEFs was found to express either the WT or C455R mutant NOTCH3 with DLL1-expressing cells led to the expression of col18α1 mRNA, (FIG. 3B), though induction was significantly less pronounced in the MEFs expressing the C455R mutant NOTCH3 receptor, compared to the WT (FIG. 3B). These data are in line with the hypomorphic nature of the C455R allele (Arboleda-Velasquez et al., 2011) and suggests that col18α1 expression is dependent on NOTCH3 functionality.

Biomarkers in Degenerating Vessels

Figure 4:
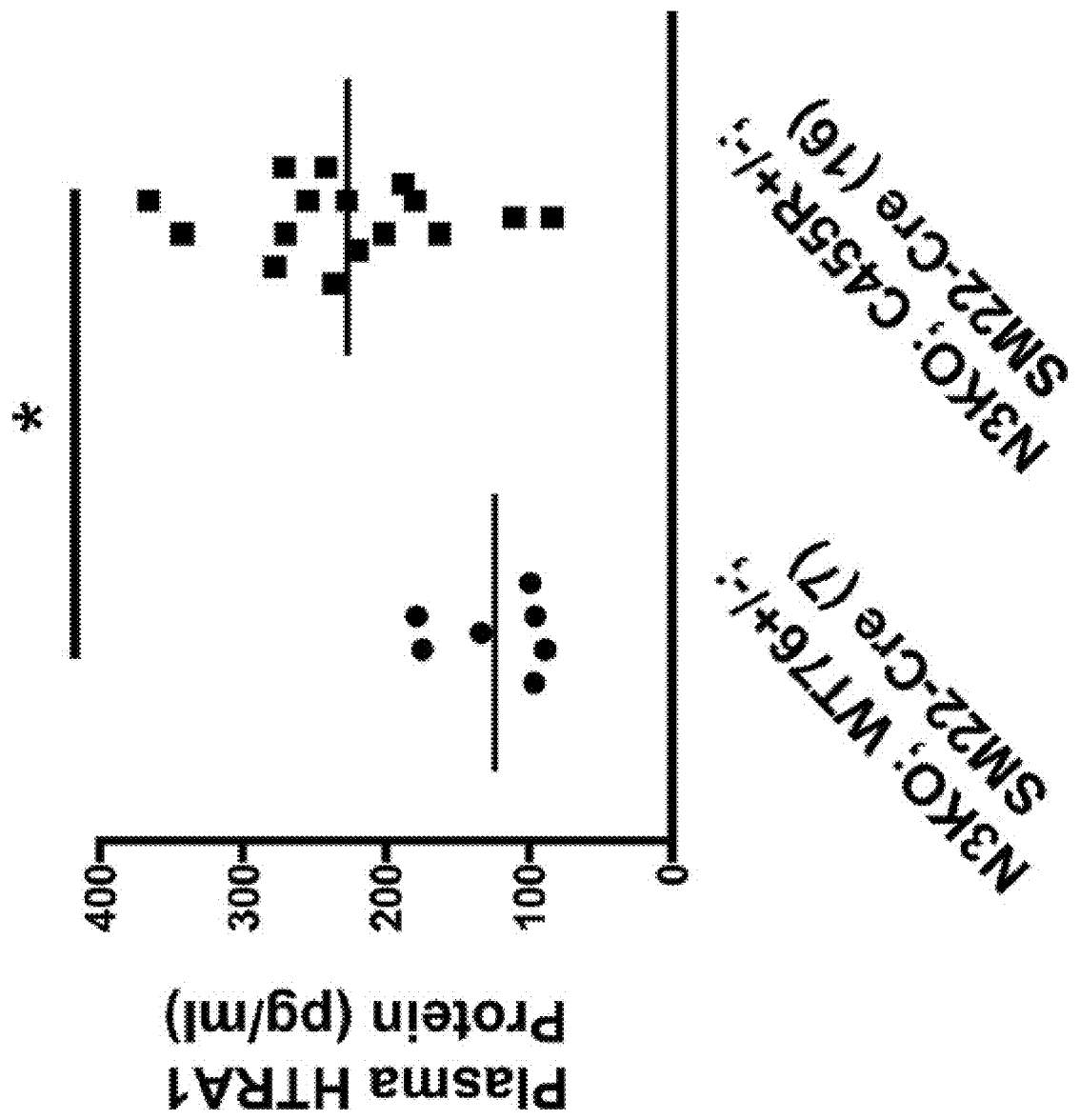
FIG. 4 is a graph showing that the HTRA1 protein is more abundant in the plasma of CADASIL mice. ELISA detection of HTRA1 in the plasma of mice (200 d) expressing the human NOTCH3 CADASIL mutation (N3KO; C455R+/−; SM22-Cre), or control (N3KO; WT76+/−; SM22-Cre) showing that there is significantly more HTRA1 protein circulating in the blood of CADASIL mice. Number of biological replicates is indicated in parenthesis. Asterisks (*) indicate P-value<0.05 (unpaired t-test).

Expression of the R1031C CADASIL mutant NOTCH3 receptor has been shown to trigger mural cell degeneration in the aortas of one-year old mice (Arboleda-Velasquez et al., 2011, Proc Natl Acad Sci USA. 108, E128-35). To search for candidate biomarkers, the proteomes of aortae of R1031C+/−; SM22-Cre mice were compared with that of mice expressing the human WT NOTCH3 protein (WT76+/−; SM22-Cre). Using quantitative MS (See Methods), 10 proteins that were more abundant were identified and 32 proteins that were less abundant were identified in aortas from R1031C+/−; SM22-Cre mice compared to control WT76+/−; SM22-Cre mice (FIG. 7B). From this list, focus was directed at high-temperature requirement A serine protease (HTRA1), which was upregulated by about 2-fold in CADASIL aortas, because mutations in HTRA1 have previously been identified as the cause of a similar SVD called cerebral autosomal recessive with subcortical infarcts and leukoencephalopathy (CARASIL) (Hara et al., 2009). To further support the notion that HTRA1 is misregulated in NOTCH3 mutant mice, ELISA was used to measure the plasma levels of HTRA1 in the C455R model (the model used in the antibody arrays above). ELISA analysis of plasma from the CADASIL N3KO; C455R+/−; SM22-Cre mice showed a significant increase in HTRA1, compared to N3KO; WT76+/−; SM22-Cre controls (FIG. 4, fold-change of 1.83, P<0.05).

NOTCH3 Ectodomain as a CADASIL Biomarker

Experiments were performed to investigate whether N3ECD could be detected in plasma and whether its levels were changed in the presence of NOTCH3 mutations. As a commercial ELISA is not available, a custom assay was designed (see Methods). No signal above background in WT C57BL/6 mice or in the NOTCH3 knockout mice (N3KO; WT76+/−) whereas signal was copious in mice expressing the human NOTCH3 protein (N3KO; WT76+/−; SM22-Cre), indicating that the N3ECD ELISA was specific for the human N3ECD (Data not shown and FIG. 5). The maximum linear range of the ELISA was 2 µg/ml (FIG. 5A). This assay was also capable of detecting N3ECD in both human plasma and serum samples, with higher levels found in the serum (FIG. 5B, 14 ng/ul versus 51 ng/ul, P<0.01). There was a significant decrease in circulating N3ECD in the plasma of CADASIL N3KO; C455R+/−; SM22-Cre mice when compared to N3KO; WT76+/−; SM22-Cre controls (FIG. 5C, 0.6-fold change, P<0.01). RNA transgene expression was similar for CADASIL and control mice (FIG. 5D).

CADASIL Mice have a Robust Vascular Smooth Muscle Cell Loss Phenotype

Figure 6A:
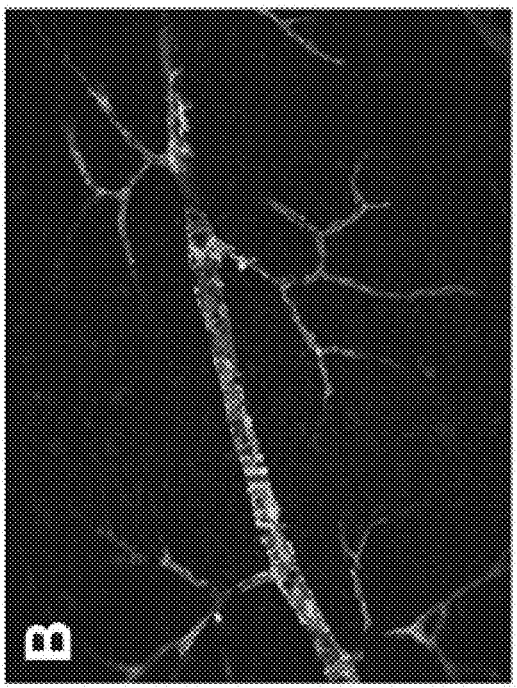
FIGS. 6A-D are images.
Figure 6B:
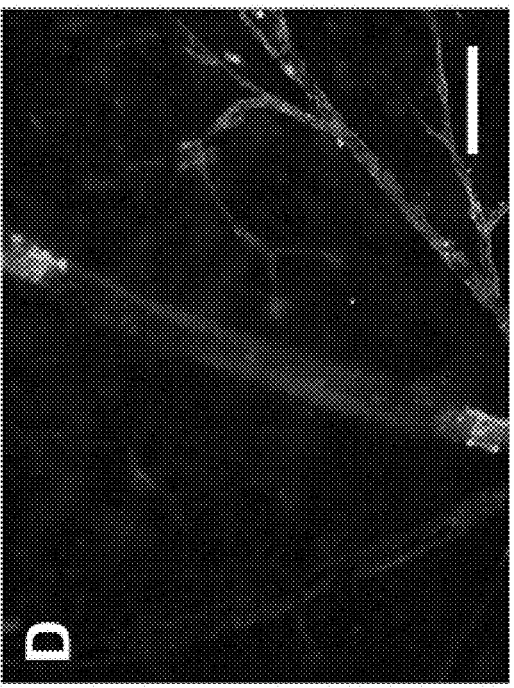
Figure 6C:
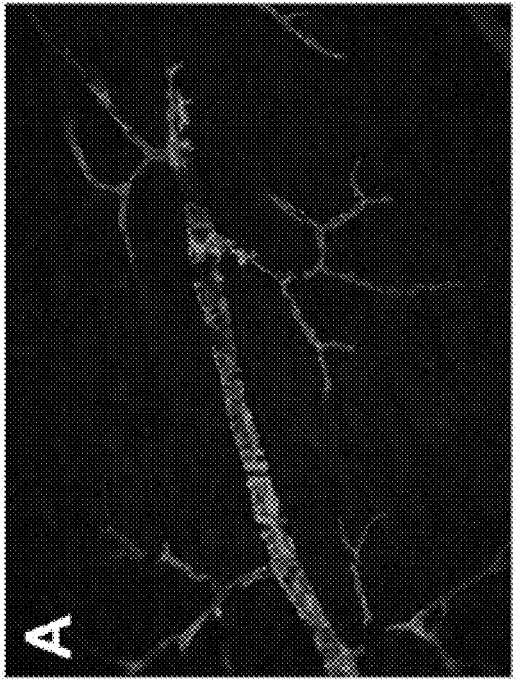
Figure 6D:
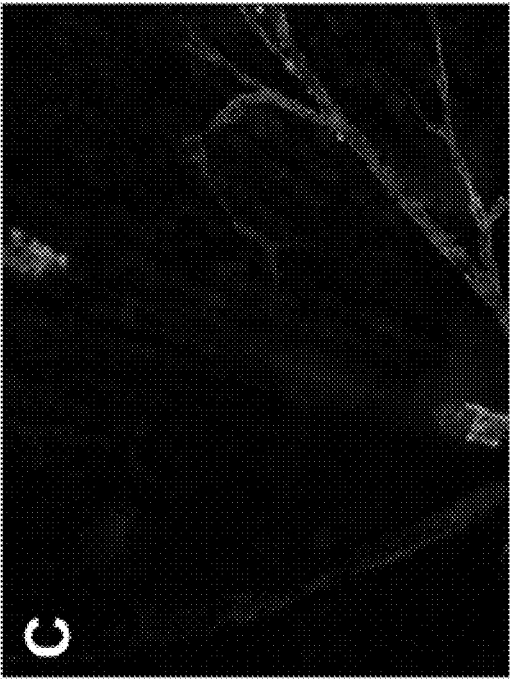
Figure 6E:
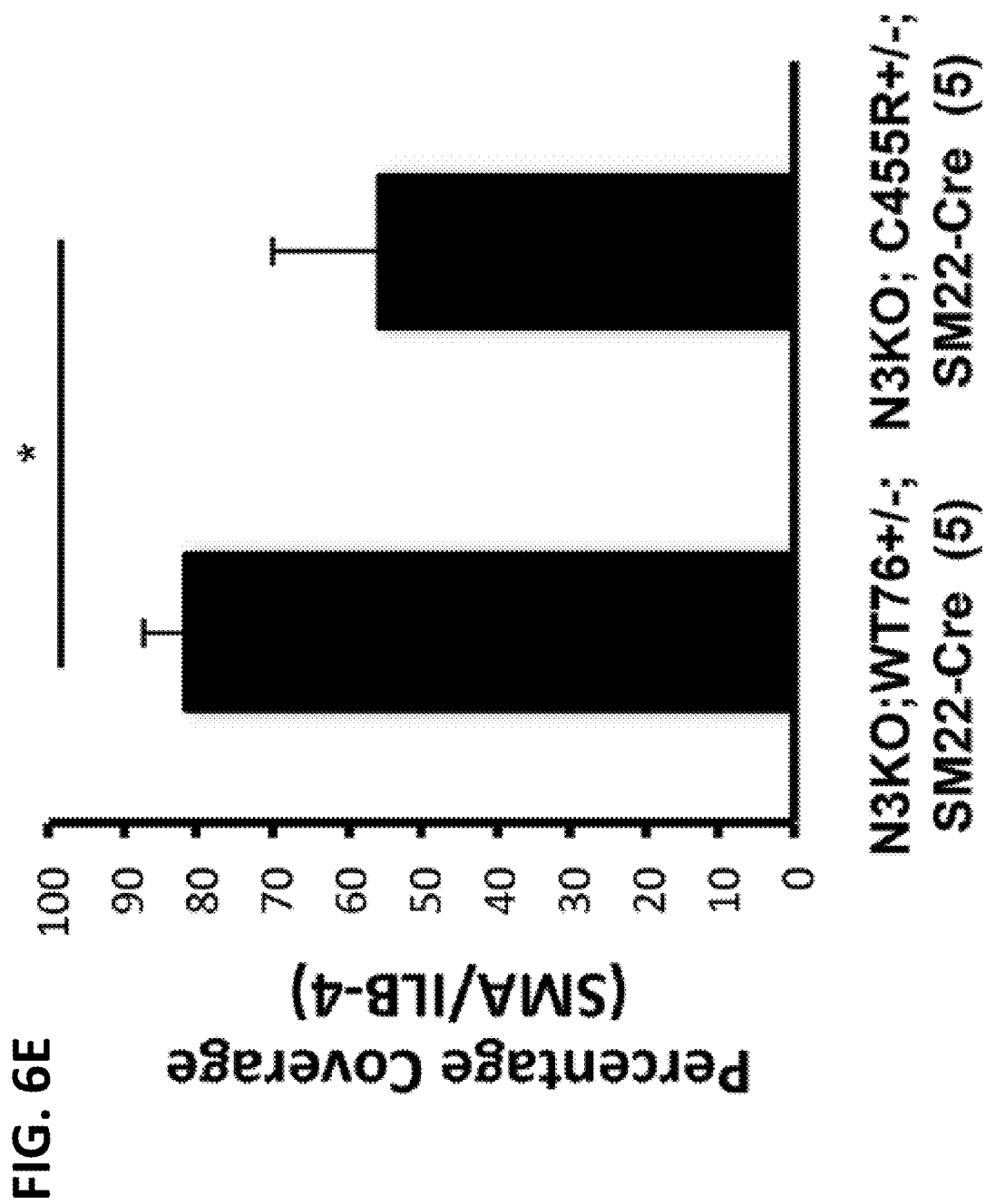
FIG. 6E is a graph, showing the loss of VSMC in the retina of CADASIL mice.

These analyses indicate that CADASIL mutations are associated with changes in plasma levels of endostatin, HTRA1 and N3ECD in mice. The level of VSMC degeneration was examined in the retina of CADASIL N3KO; C455R+/−; SM22-Cre mice. The retina was focused on because it is part of the central nervous system, has a blood barrier similar to that of the brain, and it has a highly stereotypic vascular bed allowing for systematic quantification of VSMC loss. Using smooth muscle actin (SMA), a marker for VSMC, mice carrying the C455R mutation were observed to have large gaps in VSMC (FIG. 6). This loss appeared to occur uniformly throughout the vasculature with about a 25% percent decrease in total coverage in CADASIL mice 200-days of age compared to mice carrying the WT transgene; this is the same time point at which the biomarker analyses were performed, (FIG. 6E and FIG. 8).

Figure 9:
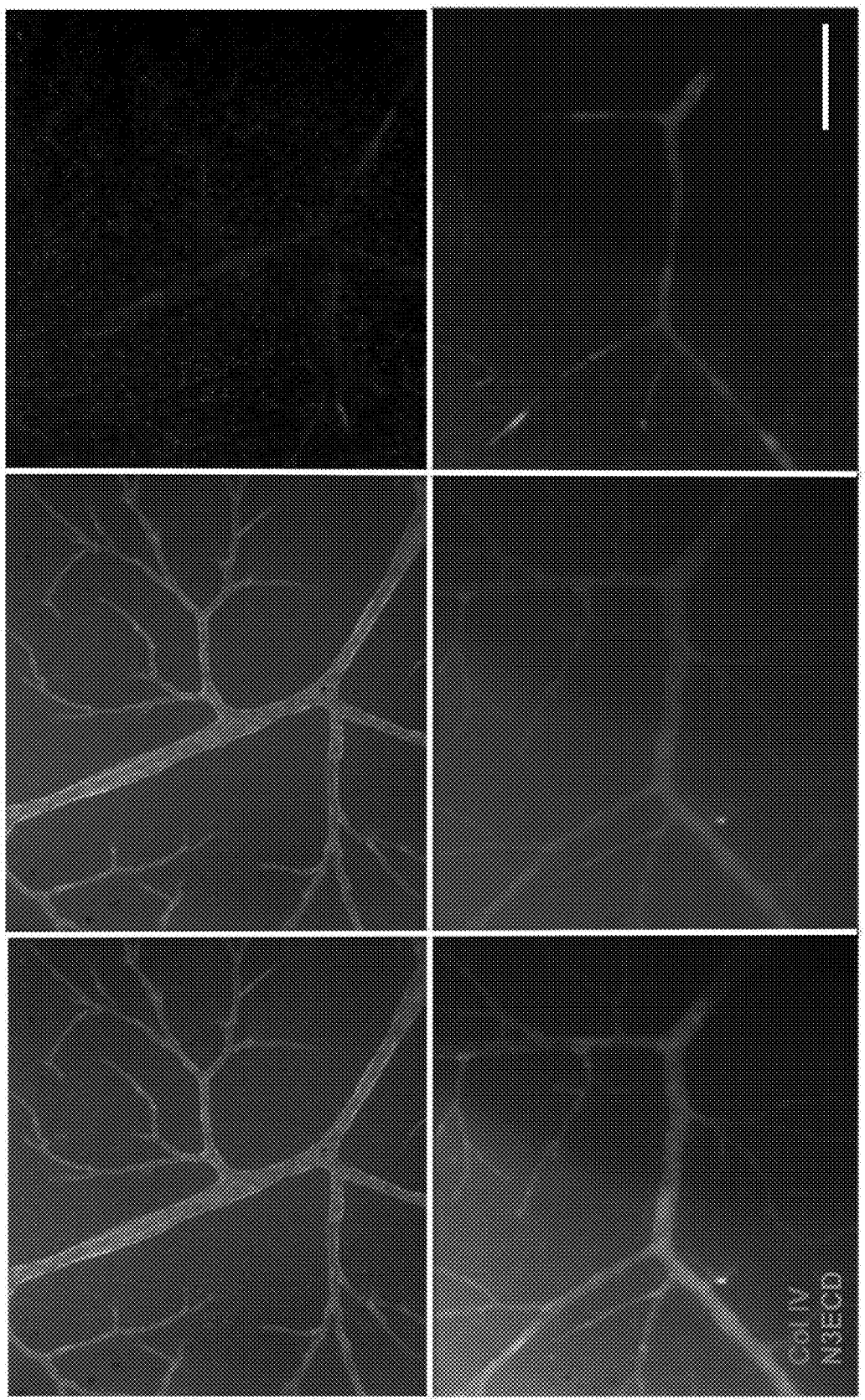
FIG. 9 is a series of images showing N3ECD expression in the retinal vasculature using retinal flat mounts. NOTCH3 receptor protein was localized in humanized transgenic mice within the superficial retinal vasculature using an antibody that targets the extracellular domain of the human NOTCH3 protein (N3ECD). Vessels were detected using collagen IV antibodies (Col IV). Scale bar is 100 µm.
Figure 10:
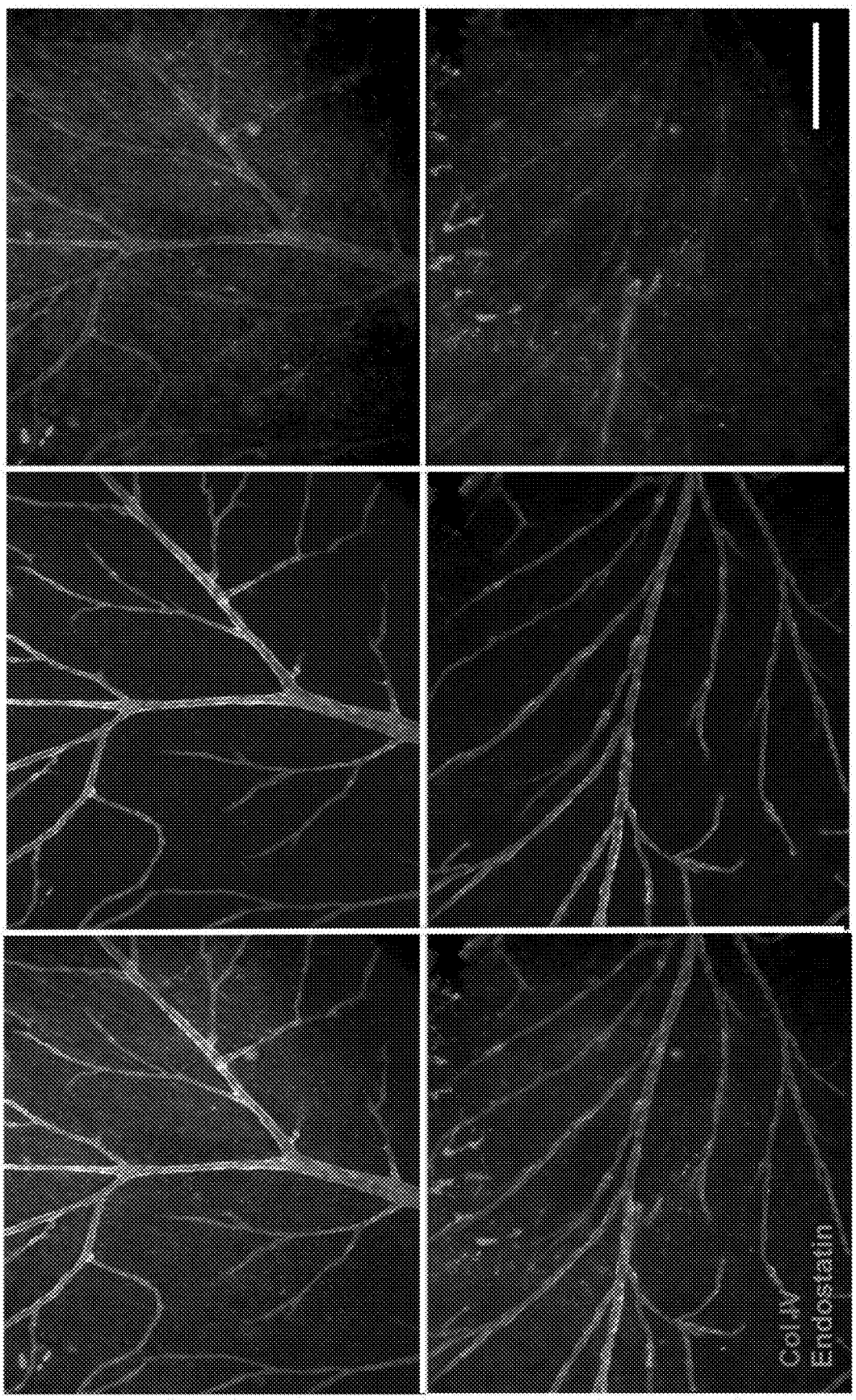
FIG. 10 is a series of images showing endostatin expression in the retinal vasculature using retinal flat mounts. Col18α1/endostatin protein was detected in the superficial retinal vasculature in N3KO; C455R+/−:SM22Cre+ mice and N3KO; WT76+/−; SM22Cre+ mice. Scale bar is 100 µm.
Figure 11:
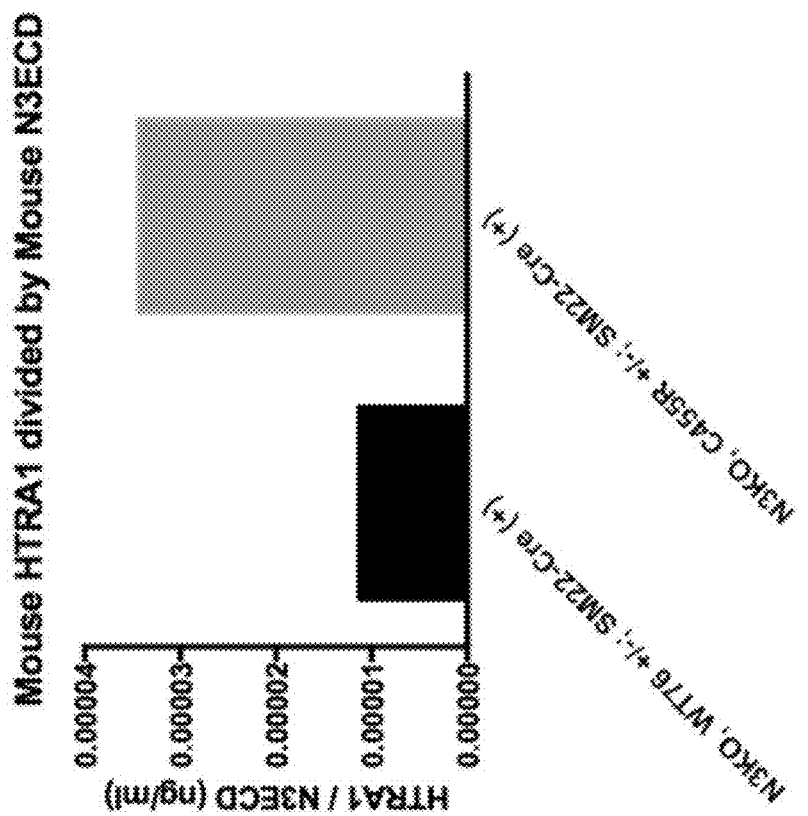
FIG. 11 is a graph comparing the ratio of the HTRA1 to NOTCH3 (i.e., N3ECD) in mice with a CADASIL mutation compared to mice without the mutation.

Immunofluorescence localization revealed strong N3ECD staining throughout the retinal vasculature of the CADASIL mice, N3KO; C455R+/−; SM22-Cre, most prominently in large caliber arteries, whereas expression in the control N3KO; WT76+/−; SM22-Cre mice was less robust (FIG. 9). Col18α1/endostatin staining was also localized to retinal vessels (FIG. 10), but in contrast to the N3ECD staining was detected predominantly in capillaries at the periphery of the retina in CADASIL N3KO; C455R+/−; SM22-Cre mice.

Blood Biomarkers and Diagnostic Methods for SVDs

In the present Example, mouse models of CADASIL, carrying either the C455R or the R1031C mutations in NOTCH3, were used to identify increased plasma levels of col18α1/endostatin and HTRA1, decreased levels of N3ECD, and loss of VSMC in retinal vessels as candidate biomarkers associated with CADASIL mutations in mice. Mice expressing the C455R mutant NOTCH3 receptor displayed robust VSMC loss in the retinal vasculature by six-months of age. The cerebrovasculature of these mice carrying the C455R mutation in NOTCH3 is being characterized, however, analyses of the retina offer significant advantages including clear visualization of coverage along the length of individual vessels and their branches in a tissue containing a blood barrier similar to that of the brain. Previous analyses of the retinal vasculature in NOTCH3 mutant mouse models have also been helpful in identifying pericytes loss further validating the use of the retinal vasculature as informative for CADASIL phenotypes (Henshall et al., 2015, Arterioscler Thromb Vasc Biol. 35, 409-20; Kofler et al., 2015, Sci Rep. 5, 16449).

Antibody arrays for angiogenesis-related proteins were used to determine whether proteins in this category could be dysregulated in CADASIL mice. Antibody arrays are not without limitations because the results could be affected by protein-protein interactions within the sample mixture (Kodadek, 2001, Chem Biol. 8, 105-15), which may explain the discrepancy in the results for endostatin between antibody arrays and ELISA. Notwithstanding these limitations, the endostatin finding may be functionally relevant to the pathobiology of CADASIL as identified possible differences in the vascular distribution of col18α1/endostatin in the retina were identified and differences in circulating levels of endostatin have been shown to be prognostic for ischemic stroke (Navarro-Sobrino et al., 2011, Atherosclerosis. 216, 205-11). Furthermore, the analyses in this Example indicated that the increased plasma levels of col18α1/endostatin in mice carrying the C455R mutation was not directly related to the effects of the CADASIL mutation on NOTCH3 signaling; col18α1/endostatin mRNA expression levels were increased in cells expressing WT human NOTCH3 and reduced in cells expressing the C455R mutant.

Using aortas from mice carrying the R1031C mutation, MS analysis identified HTRA1 as a misregulated protein. In humans, CADASIL affects primarily small caliber vessels in the brain (Louvi et al., 2006, Developmental Neuroscience. 28, 5-12), although possible effects in large vessels have not been systematically analyzed. In CADASIL mice, however, the phenotype reported was overt, with aortas losing about half their width by one year of age (Arboleda-Velasquez et al., 2011, Proc Natl Acad Sci USA. 108, E128-35), providing a rationale for using this tissue in this Example. The finding of HTRA1 changes in affected vessels from a CADASIL mouse model is of particular interest because mutations in this protein are associated with a similar SVD known as CARASIL (Hara et al., 2009, The New England journal of medicine. 360, 1729-39). The similarities between CADASIL and CARASIL have been reviewed in detail (Tikka et al., 2014, Brain: J. Neurol. 132, 933-939), however, notable similarities include cerebral small vessel disease associated with a loss of VSMC coverage, stroke and cognitive impairment. It is unclear how the NOTCH3 CADASIL mutations lead to HTRA1 accumulation in vessels and in plasma and whether HTRA1 may contribute to CADASIL pathobiology. Mutations in CARASIL have been proposed to cause a loss of function in HTRA1 activity and, by effect, a gain of function in TGF-β signaling as the mutant HTRA1 fails to repress TGF-β signaling (Hara et al., 2009, The New England journal of medicine. 360, 1729-39). However, another hypothesis postulates that CARASIL pathobiology is associated with diminished TGF-β signaling caused by defective HTRA1-mediated cleavage of latent TGF-β binding protein 1 (LTBP-1), a known TGF-β facilitator protein (Beaufort et al., 2014, Proc Natl Acad Sci USA. 111, 16496-501).

The C455R CADASIL mouse model had less detectable N3ECD in plasma when compared to controls and this difference was not explained by differences in levels of mRNA expression. The decreased levels of N3ECD may be related to impaired NOTCH3 signaling as it is known that upon proteolytic cleavage of the NOTCH receptors the NOTCH ectodomain is released from the receptor expressing cell and transendocytosed into the ligand-expressing cell (Klueg and Muskavitch, 1999, J Cell Sci. 112 (Pt 19), 3289-97), a process that may be impaired by deficient signaling. Alternatively, it is possible that mutant N3ECD accumulates in vessels as GOMs, as it has been suggested occurs in humans and mouse models (Monet-Lepretre et al., 2013, Brain. 136, 1830-45; Joutel et al., 2010, J Clin Invest. 120, 433-45), resulting in less detectable N3ECD in plasma of the CADASIL mice (FIG. 5C). In support of this concept, N3ECD staining was found to be more prominent in vessels from CADASIL (C455R) mice compared to controls. The notion that the extracellular domain of the NOTCH3 receptor circulates in blood and that its levels may change in CADASIL is novel and it remains to be established if they are functional in this compartment. The use of N3ECD as a plasma biomarker may have some practical advantages over the recently reported "Notch3 score", which represents a measure for the NOTCH3 accumulation based upon immunohistochemistry analysis of postmortem brain tissue from mice (Rutten et al., 2015), as plasma N3ECD could be measured over time from live animals allowing prospective analyses.

Monitoring the level of these biomarkers at the beginning and end of a trial may offer a means to quantify the efficacy of a treatment that is both inexpensive and technically feasible. Possible therapies include modulation of NOTCH3 signaling to test the NOTCH3 signaling defect hypothesis in CADASIL (Arboleda-Velasquez et al., 2011, Proc Natl Acad Sci USA. 108, E128-35). Other approaches include therapeutic NOTCH3 cysteine correction in CADASIL using exon skipping or allele specific regulation of NOTCH3 expression, which will constitute a direct test of the NOTCH3 (ECD) toxic accumulation cascade hypothesis (Rutten et al., 2016, Brain 139 (Pt 4):1123-35).

The present subject matter provides three circulating protein biomarkers SVD: endostatin, HTRA1, and NOTCH3. Those these biomarkers were identified in in a C445R mouse model of CADASIL, they are useful for diagnostic, prognostic, and therapeutic methods disclosed herein. Changes in these proteins occurred in mice by 200-days of age, coincident with a significant loss of VSMC in the retina. Quantification of these three proteins, along with analyses of VSMC coverage in the retina, may be used as a surrogate endpoints in future preclinical trials of CADASIL and other SVDs, as well as in clinical settings, such as during the treatment and/or diagnostic and/or prognostic evaluation of subjects.

Experimental Procedures
Animal Models

All mouse models used in this study were previously described (Arboleda-Velasquez et al., 2008, Proc Natl Acad Sci USA 105, 4856-61; Arboleda-Velasquez et al., 2011, Proc Natl Acad Sci USA, 108, E128-35). Briefly, mice express either a wild type human NOTCH3 transgene (WT76) or a mutated human NOTCH3 transgene (C455R or R1031C), or a NOTCH ligand (DLL1); transgenes are inserted into the ROSA26 locus (Soriano, 1999, Nat Genet. 21, 70-1) and expression occurs through Cre-mediated recombination.

Both male and female animals were included in the study.
Plasma Collection

Plasma was collected from mice with the following genotypes: a mouse endogenous NOTCH3 knockout (N3KO), and a N3KO mouse heterozygous for the WT (WT76) human or mutant (C455R) human NOTCH3 transgene, both driven by SM22-Cre (N3KO; WT76+/−; SM22-Cre and N3KO; C455R+/−; SM22-Cre, respectively). Mice were anesthetized using a mixture of ketamine (120 mg/kg) and xylazine (20 mg/kg) using a 0.5", 27 G needle via intraperitoneal injection. Under anesthesia, the anterior chest wall was removed and the left ventricle was pierced with a 0.5", 20 G needle. Blood was aspirated and dispensed, into a BD Vacutainer K2 EDTA, lavender top, blood collection tube (BD 367841). This tube was inverted several times to ensure the blood made contact with the entire surface of the EDTA-coated tube. The tube was then placed on ice and immediately processed for plasma following the manufacture's protocol. Plasma was aliquoted into 100 µl volumes in Eppendorf LoBind Protein Microcentrifuge Tubes (Eppendorf, 022431102) then stored at −80° C. until use.

Human Plasma Collection

Plasma was prepared from blood obtained through venipuncture using BD Vacutainer K2 EDTA tubes then stored at −80° C. until use.

Candidate Biomarker Screening Using an Angiogenesis Antibody Array Plasma (200 µl) from control mice (N3KO; WT76+/−; SM22-Cre), CADASIL mutant mice (N3KO; C455R+/−; SM22-Cre), and endogenous NOTCH3 knockout mice (N3KO) was processed on the Proteome Profiler Angiogenesis Array Kit (R&D Systems, ARY015), according to the manufacture's protocol. For all antibody arrays, two control and two experimental mice were used. Dot blot analysis was performed via Image J by measuring integrated density. Background was accounted for by subtracting the integrated density of the dot's surrounding area. A variance analysis was conducted on each array (FIGS. 1 and 2) to identify potential candidate proteins, as previously described (Arboleda-Velasquez et al., 2011). Proteins of interest were considered to be differentially abundant in plasma if the absolute value of the difference between the two control (N3KO; WT76+/−; SM22-Cre) and two experimental (N3KO; C455R+/−; SM22-Cre) mice exceeded 1.5 times the variation (equation below).

$$Var = \sqrt{\frac{(Control1 - Control2)^2 + (Experimental1 - Experimental2)^2}{2}}$$

Candidate proteins that were differentially abundant in at least two of the three arrays were selected for validation via ELISA.

Candidate Biomarker Identification Utilizing a MS Proteomic Screen

The material used for MS was obtained from a cohort of previously published mice and analyzed for different parameters (Arboleda-Velasquez et al., 2011, Proc Natl Acad Sci USA, 108, E128-35). The genotypes of the mice, all wild type for the endogenous mouse NOTCH3, were heterozygous for the WT (WT76) human or mutant (R1031C) human NOTCH3 transgene, driven by SM22-Cre (WT76+/−; SM22-Cre and R1031C+/−; SM22-Cre), respectively.

Aortas were isolated from one-year old mice and homogenized in 8 M urea and 50 mmol/L Tris-HCl (pH 8). Protein from each sample was reduced, alkylated and digested using 1 µg of Lys-C at 37° C. overnight. Peptides from proteolytic digestion were desalted and labeled using reductive dimethylation (Boersema et al., 2008, Proteomics. 8, 4624-32; Hsu et al., 2003, Anal Chem. 75, 6843-52). Samples were labeled with light (CH2O—NaBH3CN) and heavy (CD2O-NaBD3CN) reagents, respectively. The samples were washed with 0.1% formic acid and eluted from the column using 80% ACN and 0.5% acetic acid. Samples were then dried down using a vacuum centrifuge. Peptides from light or heavy aorta samples were separated by strong cation-exchange chromatography into 20 fractions. Each fraction was dried down by vacuum centrifugation and desalted using self-packed C18 STAGE-tips (Rappsilber et al., 2003, Anal Chem. 75, 663-70). All liquid chromatography-tandem mass spectrometry (LC-MS/MS) data were obtained using an LTQ-Orbitrap Discovery hybrid mass spectrometer (Thermo Fisher, San Jose, CA). Each sample was loaded onto a reverse phase column and separated using 95 min LC gradient of 5-27% buffer B at a flow of 0.5-1 µl/min. MS analysis was performed using a top 10 method where the MS1 scan was acquired in the Orbitrap, followed by 10 data depended MS/MS scans on the 10 most intense ions in the LTQ with CID for fragmentation. MS/MS spectra assignments were made with the Sequest algorithm (Eng et al., 1994, J Am Soc Mass Spectrom. 5, 976-89) using the entire mouse IPI database (version 3.6).

Sequest searches were performed using a target-decoy strategy (Elias and Gygi, 2010, Methods Mol Biol. 604, 55-71) with the mouse IPI database in correct orientation (forward database) and the same database but with all sequences in reverse orientation (reverse database). Sequest searching was performed with a precursor ion tolerance of 50 ppm with LysC specificity. For dimethyl labels, a static modification of 28.0313 Da was used on the N-terminus and lysine residues. In addition, a differential modification of 8.044336 Da was used for heavy proteins, respectively, on the N-terminus and lysine residues. A protein level false discovery rate of 1% was used as a threshold for protein identifications using the target decoy strategy. Quantification of each protein was determined using the peak heights for light and heavy forms for that protein. The criterion for protein quantification was a signal-to-noise ratio of 5 for at least one of the protein species (light or heavy). Quantification of protein level was performed by calculating the median value of the ratios of light to heavy. Using this method of quantification, the contribution of single peptide protein species in the data set was low (5%), presumably reflecting the high accuracy and sensitivity of the MS methods and the high signal-to-noise cutoff used. Z scores were given to the proteins of the R1031C mice based on the standard deviation of the control mice. A median score of plus or minus two was used as a cut off to generate a list of candidate proteins (FIG. 7B). Proteins identified as candidates passed this cut off criteria in two independent MS experiments, each utilizing one aorta per genotype.

Candidate Validation Using ELISA

Endostatin and HTRA1 were measured using commercially available ELISA kits (MyBiosource, MBS266186 and MBS90656, respectively), according to the provider's protocol. The genotype of the samples tested was masked to the investigator conducting the assays and samples were randomized in the plates to prevent position effects. No samples were excluded from the analyses on the basis of being outliers.

NOTCH3 Extracellular Domain ELISA

The N3ECD sandwich enzyme-linked immunosorbent assay was designed using commercially available antibodies. A monoclonal capture antibody (R&D systems MAB 1559) was coated on a high affinity binding ELISA plate (Fisher Scientific 3590) at 625 ng/ml in 100 µl of PBS, overnight, on a rotator, at 4° C. The plate was then blocked using 300 µl of a 10% BSA solution in PBS at room temperature on a rotator for 2-3 h and washed three times with wash buffer diluted in distilled water from a 25× stock (R&D systems WA126). Recombinant human NOTCH3 extracellular domain region (N3ECD), which was originally used to raise the antibodies (R&D systems 1559-NT-050), was used as a positive control and standard. Recombinant N3ECD serially diluted from 2 ng/ml to 0.125 ng/ml, along with experimental serum or plasma samples diluted 1:10 in PBS, were applied to the plate and left to incubate on a shaker overnight at 4° C.

Biotinylated polyclonal antibody raised against the N3ECD (R&D Systems BAF1559) was used for detection. This antibody was diluted in solution of PBS containing 2.5% BSA (Sigma) to a final concentration of 0.001 mg/ml. One hundred µl was applied to each well and left at room temperature on a rotator for 2 h. The plate was washed three times and a Horse Radish Peroxidase-streptavidin (HRP-Strep) complex was added (R&D Systems DY998). The HRP-Strep complex was diluted using Reagent Calibrator Diluent 2 (R&D Systems DY008) at a 1× concentration. For each well 5 µl of HRP-Strep was added to 95 µl of the 1× calibrator diluent. One hundred µl of the diluted HRP-Strep complex was applied to the plate and left on a rotator at room temperature for 40 min. The plate was then washed five times to ensure complete removal of the HRP-Strep. After this, 100 µl of tetramethylbenzedine (TMB) (R&D Systems DY008) was added to the plate, initiating the detection phase of the reaction. Termination of this reaction took place after 20 min using 50 µl of warm (37° C.) sulfuric acid. The plate was then read using a SPECTRAmax plus 384 from Molecular Devices using a 450 nm wavelength.

To test the ability of the ELISA to detect circulating N3ECD in human samples, serially diluted plasma and serum samples, from patients with no CADASIL mutations, were used.

Ligand-Dependent NOTCH Signaling Assay

Ligand-dependent NOTCH signaling assay was performed as described previously (Arboleda-Velasquez et al., 2011). Briefly, mouse embryonic fibroblasts (MEFs) were isolated from N3KO; WT76+/+ or N3KO; C455R+/+ embryos for signal-receiving cells, and from ROSA26$^{DLL1+/+}$ embryos for signal-sending cells. Induction of the different transgenes at the ROSA26 locus was achieved by in vitro infection with an adenovirus encoding the Cre recombinase (adeno-Cre, 12.5 d.p.c.). This inducible transgene system was chosen to avoid creating an early selection pressure in the generation of the MEFs used in these experiments. MEFs were first generated in non-induced cells and then induction was performed prior to coculture.

Signal-sending and signal-receiving cells were plated together at a ratio of 2:1 respectively to ensure every signal-receiving cell was exposed to the DLL1 ligand, cultured together for 48 h, before signal-receiving cells were sorted by FACS based upon their eGFP expression (the transgene is bicistronic including the NOTCH3-IRES-eGFP) and directly lysed into RLT lysis buffer for RNA extraction with the RNeasy kit (Qiagen). Following retro-transcription of 600 ng total RNA (High Capacity Archive RNA-to-cDNA Kit, Applied Biosystems), col18α1/endostatin cDNA levels were assessed by TaqMan qPCR (Gene Expression Assay Mm00487131_m1) following manufacturer's guidelines (Applied Biosystems). Differential expression was calculated using the $2^{-\partial Ct}$ method with mouse Tbp (Mm00446973_m1) used to normalize cDNA input. Relative expression was calculated by normalizing on control samples where signal-receiving cells were cocultured with ROSA26$^{DLL1+/+}$ cells that were not induced with Cre and therefore did not over-express the DLL1 ligand.

Quantification of Smooth Muscle Cell Loss in the Vasculature

VSMC loss in the retinal vasculature was quantified in 10 animals: five control N3KO; WT76+/−; SM22-Cre mice and five CADASIL N3KO; C455R+/−; SM22-Cre mice. Animals were sacrificed and whole eyes were removed and immediately fixed overnight in 4% paraformaldehyde at 4° C. Following dissection and removal of the fixed retina from the eyecup, retina was washed three times in 2 ml of phosphate buffered saline (PBS) at room temperature for three minutes. Blocking buffer was then applied for a minimum of 5 h at room temperature. Blocking buffer consists of 1 μmol/L CaCl$_2$, 1 μmol/L MgCl$_2$, 1 μmol/L MnCl$_2$, 3.9 mmol/L sodium citrate, 1% Triton, and 0.3% goat serum, all diluted in PBS.

The retinas were then incubated with 5 mg/ml of Alexa 488-conjugated isolectin B4 glycoprotein (IB4) [1 in 200] (Invitrogen 121411) and 10 mg/ml of Cy3-conjugated smooth muscle actin antibody (SMA) [1 in 100] (Sigma C6198), in a final volume of 300 μl of blocking buffer overnight at 4° C. on a rotator before the retina was then washed with PBS and then mounted for imaging. Whole retina images were taken under 5× (×1.25) using the Zeiss Axioskope 2 mot plus microscope, using the red and green channels. The SMA coverage was quantified using ImageJ macros as follows. The program utilizes the signal of the IB4 positive staining to "outline" the area of the vessels to obtain a measurement of the total vascular area. Then the red channel is assessed for positive signal and the area for the regions of positive signal are recorded. The macro then produces an analyzed image, outlining the vascularized area in blue and the SMA positive area in red, and a table of results of vascular area and SMA positive area to be utilized for calculating percent coverage from the ratio of SMA positive area to total vascularized area.

NOTCH3 and Endostatin Retina Staining

Staining was performed in retinas of 6-month old N3KO; C455R+/−; SM22-Cre, and N3KO; WT76+/−; SM22-Cre mice with antibodies against either NOTCH3 extracellular domain (1 in 200) (EMD Millipore MABC594) or endostatin (1 in 120) (R&D Systems BAF570) with Col IV, a vessel marker, [1:200] (Abcam ab6586) in a total volume of 300 μl per retina. Retinas were prepared as described above and then placed in 300 μl of blocking solution with one of the two pairs of antibodies and imaged as described above.

Statistical Analysis

An unpaired students t-test function assuming a two tailed distribution and equal variance as statistical comparison of the ELISA results and VSMC loss quantification. P values<0.05 were considered significant and are indicated with an asterisk (*).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method comprising:
providing a test sample from a subject comprising whole blood, plasma, or serum;
assaying the sample to determine a level of: (i) Neurogenic Locus Notch Homolog Protein 3 (NOTCH3) extracellular domain (N3ECD), (ii) collagen18α1/endostatin and (iii), High-Temperature Requirement A Serine Peptidase 1 (HTRA1) in the test sample.

2. The method of claim 1, wherein the subject is suspected of having CADASIL.

3. The method of claim 1, wherein
(i) assaying the level of N3ECD comprises detecting the level of a N3ECD protein comprising the amino acid sequence of SEQ ID NO: 5;
(ii) assaying the level of collagen18α1/endostatin comprises detecting the level of a collagen18α1/endostatin protein comprising the amino acid sequence of SEQ ID NO: 1; and/or
(iii) assaying the level of HTRA1 comprises detecting the level of a HTRA1 protein having the amino acid sequence of SEQ ID NO: 9.

4. The method of claim 1, wherein
(i) assaying the level of collagen18α1/endostatin comprises contacting the collagen18α1/endostatin protein with an anti-collagen18α1/endostatin antibody;
(ii) assaying the level of HTRA1 comprises contacting the HTRA1 protein with an anti-HTRA1 antibody; and/or
(iii) assaying the level of N3ECD comprises contacting the N3ECD protein with an anti-N3ECD antibody.

5. The method of claim 1, wherein
(i) assaying the level of collagen18α1/endostatin comprises detecting the level of collagen18α1/endostatin mRNA;
(ii) assaying the level of HTRA1 comprises detecting the level of HTRA1 mRNA; and/or
(iii) assaying the level of N3ECD comprises detecting the level of N3ECD mRNA.

6. The method of claim 5, wherein
(i) detecting the level of collagen18α1/endostatin mRNA comprises contacting the collagen18α1/endostatin mRNA with a probe or a primer that is complementary to SEQ ID NO: 2;
(ii) detecting the level of HTRA1 mRNA comprises contacting the HTRA1 mRNA with a probe or a primer that is complementary to SEQ ID NO: 12; and/or
(iv) detecting the level of N3ECD mRNA comprises contacting the N3ECD mRNA with a probe or a primer that is complementary to a nucleic acid sequence encoding the amino acid sequence of SEQ ID NO: 5.

7. The method of claim 1, wherein the subject does not contain a mutated HTRA1 gene.

8. The method of claim 1, which does not comprise assaying and/or detecting the level of Fas ligand (FasL).

9. The method of claim 1, wherein said subject has diabetes.

10. The method of claim 1, wherein assaying the level of collagen18α1/endostatin, HTRA1, and N3ECD comprises contacting said collagen18α1/endostatin, HTRA1, and/or N3ECD with a collagen18α1/endostatin-specific, HTRA1-specific and/or N3ECD-specific binding agent.

11. The method of claim 10, wherein said binding agent comprises an antibody or a fragment thereof, a polypeptide or a fragment thereof, or a nucleic acid.

12. The method of claim 11, wherein said binding agent comprises an antibody or a fragment thereof.

13. The method of claim 12, wherein said antibody comprises an anti-collagen18α1/endostatin antibody, an anti-HTRA1 antibody, or an anti-N3ECD antibody.

14. The method of claim 12, wherein said antibody or fragment thereof is attached to a solid support.

15. The method of claim 11, wherein said nucleic acid comprises a probe or a primer that is complementary to mRNA that encodes collagen18α1/endostatin, HTRA1, and/or N3ECD.

16. The method of claim 1, wherein said assaying comprises an enzyme immunoassay (EIA).

17. The method of claim 1, wherein said assaying comprises an enzyme-linked immunosorbent assay (ELISA), a Western blot, a mass spectrometry assay, a radioimmunoassay, or a fluoroimmunoassay.

18. The method of claim 1, wherein said assaying comprises high-performance liquid chromatography (HPLC), liquid chromatography-mass spectrometry (LC/MS), protein immunoprecipitation, immunoelectrophoresis, or protein immunostaining.

19. The method of claim 1, wherein said assaying comprises a polymerase chain reaction (PCR).

20. The method of claim 1, wherein said assaying comprises quantitative reverse transcription PCR, microarray analysis, RNA sequencing, Northern analysis, a Nuclease Protection Assay, or in situ hybridization.

* * * * *